(12) United States Patent
Wang et al.

(10) Patent No.: US 10,544,090 B2
(45) Date of Patent: Jan. 28, 2020

(54) ANTHRAQUINONE ANALOGS AND METHODS OF MAKING AND USING THEREOF

(71) Applicants: Georgia State University Research Foundation, Inc., Atlanta, GA (US); Emory University, Atlanta, GA (US); Children's Healthcare of Atlanta, Atlanta, GA (US)

(72) Inventors: Binghe Wang, Marietta, GA (US); Chaofeng Dai, Atlanta, GA (US); Alexander Draganov, Atlanta, GA (US); Xiaochuan Yang, Baltimore, MD (US); Guojing Sun, Atlanta, GA (US); Chunhao Yang, Shanghai (CN); Weixuan Chen, Atlanta, GA (US); Nanting Ni, Goleta, CA (US); Muxiang Zhou, Tucker, GA (US); Lubing Gu, Tucker, GA (US)

(73) Assignees: Georgia State University Research Foundation, Inc., Atlanta, GA (US); Emory University, Atlanta, GA (US); Children's Healthcare of Atlanta, Inc., Atlanta, GA (US)

( * ) Notice: Subject to any disclaimer, the term of this patent is extended or adjusted under 35 U.S.C. 154(b) by 294 days.

(21) Appl. No.: 14/413,137

(22) PCT Filed: Jul. 10, 2013

(86) PCT No.: PCT/US2013/049898
§ 371 (c)(1),
(2) Date: Jan. 6, 2015

(87) PCT Pub. No.: WO2014/011753
PCT Pub. Date: Jan. 16, 2014

(65) Prior Publication Data
US 2015/0203442 A1    Jul. 23, 2015

Related U.S. Application Data

(60) Provisional application No. 61/669,927, filed on Jul. 10, 2012.

(51) Int. Cl.
C07C 233/33    (2006.01)
C07C 311/08    (2006.01)
(Continued)

(52) U.S. Cl.
CPC ............ *C07C 233/33* (2013.01); *C07C 66/02* (2013.01); *C07C 69/95* (2013.01); *C07C 225/36* (2013.01);
(Continued)

(58) Field of Classification Search
CPC . C07C 2103/24; C07C 225/36; C07C 233/31; C07C 233/33; C07C 235/16;
(Continued)

(56) References Cited

U.S. PATENT DOCUMENTS 4,244,986 A * 1/1981 Paruso .............. H01M 10/3927
423/600
5,053,431 A   10/1991 Watanabe
(Continued)

FOREIGN PATENT DOCUMENTS

CN    101475484    7/2009
CN    101613271    12/2009
(Continued)

OTHER PUBLICATIONS

Brooks and Gu. "p53 ubiquitination:Mdm2 and beyond", Mole Cell, 21:307-15 (2006).
(Continued)

*Primary Examiner* — Sabiha N Qazi
(74) *Attorney, Agent, or Firm* — Pabst Patent Group LLP

(57) ABSTRACT

Rhein analogues that exhibit anti-proliferative activity, particular against cancer cells, are described herein. In some embodiments, the compounds contain a flat or planar ring system. Such rings system by facilitate non-covalent binding of the compounds to the DNA complex, such as by inter-
(Continued)

| New Name | Record | Name | Structure | Data |
|---|---|---|---|---|
| | MG1 | BW-MDM-1 | [structure] | MW=331.02g/mol; Mass= 2.101mg |
| | MG2 | BW-MDM-2 | [structure] | MW=374.97g/mol; Mass= 2.219mg |
| | MG3 | BW-MDM-3 | [structure] | MW=422.96g/mol; Mass= 2.853mg |
| | MG4 | BW-MDM-7 | [structure] | MW=430.09g/mol; Mass= 2.020mg |
| | MG5 | BW-MDM-8 | [structure] | MW=474.04g/mol; Mass= 2.362mg | calation. In some embodiment, the compounds contain a flat or planar ring system as described above and one or more substituents which are alkylating moieties, electrophilic groups or Michael acceptors or groups which contain one or more alkylating moieties, electrophilic groups and/or Michael acceptors. The compounds described herein can also contain one more functional groups to improve the solubility of the compounds.

25 Claims, 18 Drawing Sheets

(51) Int. Cl.
| | |
|---|---|
| C07C 235/84 | (2006.01) |
| C07C 69/95 | (2006.01) |
| C07D 213/61 | (2006.01) |
| C07C 66/02 | (2006.01) |
| C07D 261/08 | (2006.01) |
| C07C 247/10 | (2006.01) |
| C07D 213/70 | (2006.01) |
| C07C 247/04 | (2006.01) |
| C07C 233/31 | (2006.01) |
| C07C 237/04 | (2006.01) |
| C07D 213/56 | (2006.01) |
| C07C 323/60 | (2006.01) |
| C07C 247/12 | (2006.01) |
| C07C 235/16 | (2006.01) |
| C07C 255/19 | (2006.01) |
| C07D 307/54 | (2006.01) |
| C07D 295/15 | (2006.01) |
| C07D 333/24 | (2006.01) |
| C07C 225/36 | (2006.01) |
| C07D 267/12 | (2006.01) |

(52) U.S. Cl.
CPC .......... *C07C 233/31* (2013.01); *C07C 235/16* (2013.01); *C07C 235/84* (2013.01); *C07C 237/04* (2013.01); *C07C 247/04* (2013.01); *C07C 247/10* (2013.01); *C07C 247/12* (2013.01); *C07C 255/19* (2013.01); *C07C 311/08* (2013.01); *C07C 323/60* (2013.01); *C07D 213/56* (2013.01); *C07D 213/61* (2013.01); *C07D 213/70* (2013.01); *C07D 261/08* (2013.01); *C07D 267/12* (2013.01); *C07D 295/15* (2013.01); *C07D 307/54* (2013.01); *C07D 333/24* (2013.01); *C07C 2603/24* (2017.05)

(58) Field of Classification Search
CPC ... C07C 235/84; C07C 237/04; C07C 247/04; C07C 247/10; C07C 247/12; C07C 255/19; C07C 311/08; C07C 323/60; C07C 66/02; C07C 69/95; C07D 13/56; C07D 213/61; C07D 213/70; C07D 261/08; C07D 295/15; C07D 307/54; C07D 333/24
USPC ........ 514/626, 605, 627, 628, 630; 552/240, 552/241
See application file for complete search history.

(56) References Cited

U.S. PATENT DOCUMENTS

| | | | | | |
|---|---|---|---|---|---|
| 5,480,873 | A * | 1/1996 | Brunavs | ........... | C07C 66/02 514/33 |
| 5,652,265 | A * | 7/1997 | Vittori | ........... | A61K 31/122 514/548 |
| 5,986,129 | A * | 11/1999 | Di Napoli | ........... | C07C 66/02 560/254 |
| 6,624,192 | B1 * | 9/2003 | Carcasona | ........... | C07C 67/08 514/510 |
| 6,797,727 | B2 * | 9/2004 | Cruz | ........... | A61K 31/222 514/510 |
| 7,132,403 | B2 * | 11/2006 | Cichewicz | ........... | A61K 31/21 514/33 |
| 8,895,725 | B2 * | 11/2014 | Wang | ........... | A61K 31/122 536/124 |

FOREIGN PATENT DOCUMENTS

| | | | |
|---|---|---|---|
| CN | 101735271 | | 6/2010 |
| CN | 102225896 | | 10/2011 |
| CN | 102241598 | | 11/2011 |
| EP | 0570091 | | 11/1993 |
| WO | 2008090078 | | 7/2008 |
| WO | 2014/011753 | * | 1/2014 |

OTHER PUBLICATIONS

Chavez-Reyes. et al., "Switching mechanisms of cell death in mdm2- and mdm4-null mice by deletion of p53 downstream targets", Cancer Res., 63:8664-9 (2003).
Cordon-Cardo, et al., "Molecular abnormalities of mdm2 and p53 genes in adult soft tissue sarcomas", Cancer Res., 52:794-9 (1984).
Cui, et al., "Preparations of anthraquinoe and napthoquinone derivaties and their cytoxic effects", Chem Pharm Bull., 59(3):302-14 (2011).
Danovi, et al., "Amplification of Mdmx (or Mdm4) directly contributes to tumor formation by inhibiting p53 tumor suppressor activity", Mole Cell Biol., 24(13):5835-433 (2004).
Fakharzadeh, et al., "Tumorigenic potential associated with enhanced expression of a gene that is amplified in a mouse tumor cell line", EMBO J., 10(6):1565-9 (1991).
Galluzzi et al., "TP53 and MTOR crosstalk to regulate cellular senescence", Aging, 2(9):535-7 (2010).
Grier, et at., "Tissue-specific differences of p53 inhibition by Mdm2 and Mdm4", Mole Cell Biol., 26(1):192-8 (2006).
Gu, et al., "Mutual dependence of MDM2 and MDMX in their functional inactivation of p53", J Biomed Chem., 277(22):19251-4 (2002).
Honda, et al., "Oncoprotein MDM2 is a ubiquitin ligase E3 for tumor suppressor p53", FEBS Lttr., 420:25-7 (1997).
Huang, et al., "The p53 inhibitors MDM2/MDMX complex is required for control of p53 activity in vivo", PNAS, 108(29):12001-6 (2011).
IP, et al., "The role of Ca+2 on rhein-induced apoptosis in human cervical cancer Ca Ski cells", Anticancer Res., 27:379-90 (2007).
Leach, et al., "p53 mutation and MDM2 amplification in human soft tissue sarcomes", Cancer Res., 53:2231-4 (1993).
Lu, et al., "The p53 tumor suppressor protein is a critical regulator of hematopoietic stem cell behavior", Cell Cycle, http://www.tandfonline.com/Loi/c=kccy20, retrieved from internet Jul. 15, 2015.
Lu, et al., "Synthesis and cytotoxicity of emodin derivatives", Chinese J Org Chem., 25:944-9 (2005) Eng Abstract.
Owton, "Synthesis of 8-Flourohein", J Chem Soc Perkin Trans., 2131-5 (1994).
Pant, et al., "Heterodimerization of Mdm2 and Mdm4 is critical for regulating p53 activity during embryogensis but dispensable for p53 and Mdm2 stability", PNAS, 108(29):11995-12000 (2011).
Priest, et al., "Deconstructing nucleotide binding activity of the Mdm2 RING domain", Nuc Acids Res., 38(21):7587-98 (2010).
Riemenschneider, et al., "Amplification and overexpression of MDM4 (MDNX) gene from 1q32 in a subset of malignant gliomas without TP53 mutation of MDM2 amplification", Cancer Res., 59:6091-6 (1990).
Sharp, et al., "Stabilization of MDM2 oncoprotein by interaction with the structually related MDMX protein", J Biol Chem., 274(53):38189-96 (1999).
Stad, et al., "Hdmx stabilizes Mdm2 and p53", Am Soc Biochem Mole Biol., pp. 1-22 published May 25, 2000.

(56) References Cited

OTHER PUBLICATIONS

Sun, et al., "Inhibition of human telomerase by a g-quadruplex-interactive compound", J Med. Chem., 40:2113-6 (1997).

Tatyana, et al., "Inhibition of HIV-1 ribonuclease H activity by novel frangula-emodine derivatives", Medicinal Chem., 5:398-410 (2009).

Van Gorkom, et al., "Cytotoxicity of rhein, the active metabolite of sennoside laxatives is reduced by multidrug resistance-associated protein", British J Cancer, 86:1494-1500 (2002).

Vousden and Prives, "Blinded by the light: the growing complexity of p53", Cell, 137:413-31 (2009).

Wang, et al., "MdmX protein is essential for Mdm2 protein-mediated p53 polyubiquitination", J Biol Chem., 286(27):23725-34 (2011).

Wang, "p53 regulation: teamwork between RING domains of Mdm2 and MdmX", Cell Cycle, 10(24):4225-9 (2011b).

Wang and Jiang, "Mdm2 and MdmX partner to regulate p53", Febs Lttrs, 586:1390-6 (2012).

Zhang and Lu, "Signaling to p53: ribosomal proteins find their way", Cancer Cell, 16:369-377 (2009).

Zhu, et al., "Microwave-assisted synthesis and antibacterial activity of 6-alkoxxy rheins", Chinese J Org Chem., 30(9):1335-41 (2010) Eng Abstract.

Ayyaangar, et al., "Anthraquinone and anthrone series-XXIII", Tetrahedron, 6(4):331-7 (1959).

Gavit, et al.: "Synthesis of 4, 5-dihydroxy-9, 10-dioxoanthracene-2-benzylCarboxylate ester from rhein", J Pharmacognosy Phytochem., http://search.proquest.com/docview/1354829123, accessed Aug. 30, 2008.

Grandmaison, et al. "Reactions of ketene acetals. 10. Total syntheses of the anthraquinones rubrocomatulin pentamethyl ether, 2-acetylemodin, 2-acetyl-5-Hydroxyemodin tetramethyl ether, and xanthorin", J Org Chem., 43(7):1435-8 (1978).

Peters, et al. "Brominated Diamino Dihydroxyanthraquinones. Blue Dyes for Synthetic-polymer Fibres", J Soc Dyers Colourists, 93:378-86 (1977).

Popov, et al. "Bromination of 1 ,5-Dinitroanthraquinone", Russ.J Org Chem., 29 (4.2):666-72 (1993).

Wannalerse, et al.: "Synthesis, optical and electrochemical properties of newReceptors and sensors containing anthraquinone and benzimidazole units", Tetrahedron, 64(46):10619-24 (2008).

Yang, et al. "Novel Rhein Analogues as Potential Anticancer Agents", Chemmedchem, 6(12):2294-301 (2011).

International Search Report for PCT/US2013/04989 dated Mar. 3, 2014.

* cited by examiner

Doxorubicin

Rhein

→ Analogues

Mitoxantrone

| New Name | Record | Name | Structure | Data |
|---|---|---|---|---|
| | MG1 | BW-MDM-1 | (anthraquinone with OH, OH, O, OH groups and -NH-C(O)-CH2-Cl substituent) | MW=331.02g/mol; Mass= 2.101mg |
| | MG2 | BW-MDM-2 | (anthraquinone with OH, OH, O, OH groups and -NH-C(O)-CH2-Br substituent) | MW=374.97g/mol; Mass= 2.219mg |
| | MG3 | BW-MDM-3 | (anthraquinone with OH, OH, O, OH groups and -NH-C(O)-CH2-I substituent) | MW=422.96g/mol; Mass= 2.853mg |
| | MG4 | BW-MDM-7 | (anthraquinone with OH, OH, O, OH groups and extended amide linker ending in -C(O)-CH2-Cl) | MW=430.09g/mol; Mass= 2.020mg |
| | MG5 | BW-MDM-8 | (anthraquinone with OH, OH, O, OH groups and extended amide linker ending in -C(O)-CH2-Br) | MW=474.04g/mol; Mass= 2.362mg |

FIG. 1b

| | | | |
|---|---|---|---|
| MG6 | BW-MDM-9 | | MW=562.17g/mol; Mass= 0.335mg |
| MG7 | BW-MDM-10 | | MW=606.12g/mol; Mass= 3.386mg |
| MG8 | BW-MDM-12 | | MW=486.51g/mol; Mass= 2.203mg |
| MG9 | BW-MDM-13 | | MW=454.47g/mol; Mass= 2.125mg |
| MG10 | BW-MDM-14 | | MW=255.23g/mol; Mass= 3.130mg |
| MG11 | BW-MDM-15 | | MW=354.36g/mol; Mass= 1.215mg |

FIG. 1c

Cytotoxicity of Rhein analogues tested by WST assay

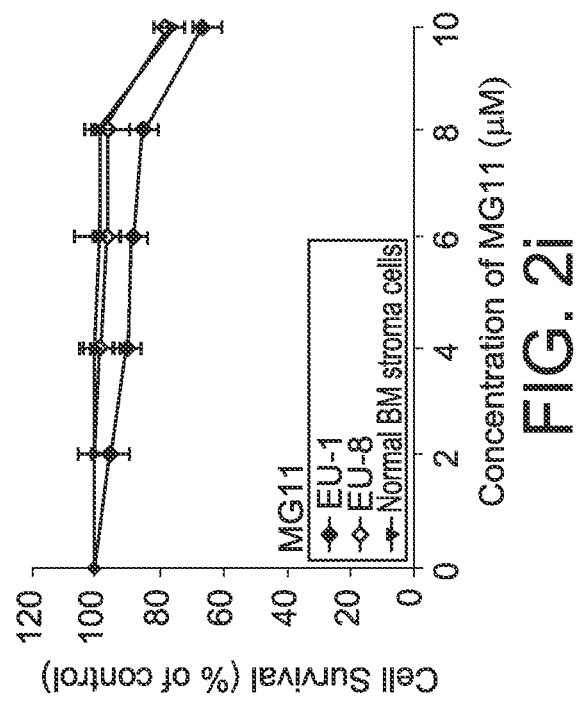

| | Treatment dose | MTD |
|---|---|---|
| Doxorubicin | 2-8 mg/kg/day | 15 mg/kg/one injection, mice died after 7 day due to severe cardiac disease |
| MG1 | 2-10 mg/kg/day (estimated according to *in vitro* test) | 100 mg/kg/day X 3 day, mice are alive after 9 days, followed by 400mg/kg/one injection, mice are still alive. |

ANTHRAQUINONE ANALOGS AND METHODS OF MAKING AND USING THEREOF

FIELD OF THE INVENTION

This invention is in the field of rhein analogs that exhibit anti-proliferative activity, particular C3 rhein analogs, and methods of making and using thereof.

BACKGROUND OF THE INVENTION

Rhein is a natural product having an anthraquinone scaffold. It is isolated from the ground plant Rhubarb, which belongs to the Rheum family. A number of anthraquinone compounds isolated form Rheum, such as emodin, have been investigated.

Rhein, and derivatives thereof, are believed to be non-covalent DNA binding drugs. In general, DNA intercalators have common structural features, such as a planar polycyclic aromatic system with different side chains that can vary from simple amines to different sugars. Intercalators can bind within the minor or the major grove of the DNA duplex. Upon binding they may induce conformational changes or even rupture the DNA helix, which can cause cell apoptosis. Another possible mechanism of action is the inhibition of enzymes that bind to the DNA, which may disrupt DNA replication, transcription, etc.

Compounds have an anthraquinone core, similar to rhein, such as doxorubicin and mitoxanthrone, have been marketed as anticancer drugs. These compounds exhibit anticancer activity; however, they have shown serious cardiotoxicity side effects. Studies have shown that rhein is well tolerated by the human body when used as a laxative, and it has anticancer activities against some tumor cells. However, the anticancer activity of rhein against number of cancer cells has been found to be relatively low with $IC_{50}$ in the range of 12-120 µM.

Therefore, there exists a need for novel compounds having similar or greater activity than doxorubicin, but with fewer side effects, such as cardiovascular side effects.

Therefore, it is an object of the invention to provide rhein analogs having similar or greater activity than doxorubicin, but with fewer side effects, such as cardiovascular side effects, and methods of making and using thereof.

SUMMARY OF THE INVENTION

Rhein analogues that exhibit anti-proliferative activity, particular against cancer cells, are described herein. In some embodiments, the compounds contain a flat or planar ring system. Such rings system by facilitate non-covalent binding of the compounds to the DNA complex, such as by intercalation. In some embodiment, the compounds contain a flat or planar ring system as described above and one or more substituents which are alkylating moieties, electrophilic groups or Michael acceptors or groups which contain one or more alkylating moieties, electrophilic groups and/or Michael acceptors. In particular embodiments, the alkylating moiety or moieties are found at the 3-position of the anthraquinone core. However, these moieties can be found at other locations including $R_1$ and $R_8$ and/or on one or more positions on the cyclic core.

The compounds described herein can also contain one more functional groups to improve the solubility of the compounds. For example, an oligo- or polyethylene glycol moiety can incorporated into one or more side chains on the cyclic core to improve solubility. Other functional groups which can improve solubility include groups that are charged or become charged under physiological conditions, such as amines, sulfates, sulfonates, sulfonates, phosphates, phosphinates, phosphonates, carboxylic acid groups, etc. In some embodiments, the one or more functional groups to improve solubility are moieties in $R_3$. In other embodiments, the functional groups to improve solubility are moieties in other positions in the molecule, such as $R_1$ and $R_8$ and/or on positions on the cyclic core.

In some embodiments, the compounds have the formula:

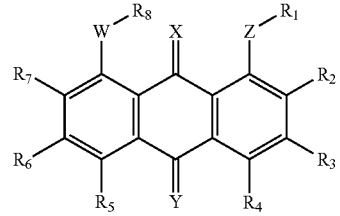

wherein
X and Y are independently O or S;
W and Z are independently absent or O, S, or substituted or unsubstituted alkylene;
$R_1$ and $R_8$ are independently hydrogen; hydroxy (—OH), thiol (—SH), substituted or unsubstituted alkyl, substituted or unsubstituted oligo- or polyether, substituted or unsubstituted primary amine, substituted or unsubstituted secondary amine, substituted or unsubstituted tertiary amine, —C(O)R or —C(O)OR, where R is hydrogen, halogen, substituted or unsubstituted alkyl or heteroalkyl, substituted or unsubstituted cycloalkyl or heterocycloalkyl, substituted or unsubstituted aryl or heteroaryl, or halogen; substituted or unsubstituted primary amide, substituted or unsubstituted secondary amide, substituted or unsubstituted tertiary amide, substituted or unsubstituted secondary carbamate, substituted or unsubstituted tertiary carbamate, substituted or unsubstituted urea, sulfinyl group, sulfonyl group, sulfino group, halogen, nitrile, $CF_3$, substituted or unsubstituted alkyl, substituted or unsubstituted cycloalkyl, substituted or unsubstituted heterocycloalkyl, substituted or unsubstituted alkylaryl, substituted or unsubstituted alkenyl, substituted or unsubstituted alkynyl, substituted or unsubstituted aryl, or substituted or unsubstituted heteroaryl group;
$R_3$ is halogen, substituted or unsubstituted alky or cycloalkyl, substituted or unsubstituted aryl; substituted or unsubstituted heteroaryl; M-Ar or M-hetAr, where Ar is substituted or unsubstituted aryl, hetAr is substituted or unsubstituted heteroaryl, and M is O, S, or $NR_9$; $N(R_9)_2$, CO—$NR_9(CH_2)_n(CH_2CH_2O)_mR_{10}$, $NR_9$—CO—$(CH_2)_n(CH_2CH_2O)_mR_{10}$, $NR_9$—CO—$(CH_2)_nR_{10}$, —$(CR_{12}R_{13})_n$COR$_{10}$, $NR_9$—$SO_2$—$(CH_2)_mR_{10}$, C≡C—$(CH_2)_nNR_9$—CO—$(CH_2)_oR_{10}$, $(CH_2)_nR_{10}$, or COR$_{10}$; wherein n, m, and o are independently an integer from 0-10, preferably 0-6, more preferably from 1-6, each occurrence of $R_9$ is independently hydrogen, alkyl, or aryl, and $R_{10}$ is hydrogen, substituted or unsubstituted alkyl or cycloalkyl, substituted or unsubstituted alkenyl or alkynyl, substituted or unsubstituted aryl or heteroaryl, or a leaving group, electrophilic group, reactive functional group, or Michael acceptor or a moiety containing a leaving group, electrophilic group, reactive functional group, or Michael acceptor;
$R_2$ and $R_4$-$R_7$ are independently hydrogen; hydroxy (—OH), thiol (—SH), ether, thioether, primary amine, secondary amine, tertiary amine, aldehyde, ketone, ester, carboxylic acid, primary amide, secondary amide, tertiary amide, secondary carbamate, tertiary carbamate, urea, sulfinyl group, sulfonyl group, sulfino group, phosphate, phosphinate, phosphonate, nitro, halogen, nitrile, $CF_3$, or substituted or unsubstituted alkyl, heteroalkyl, cycloalkyl, heterocycloalkyl, alkenyl, alkynyl, aryl or heteroaryl, or alkylaryl or alkylheteroaryl group.

In other embodiments, the compound has the formula:

[Chemical structure diagram showing a polycyclic structure with substituents $R_1$ through $R_{11}$, W, Y, Z, X]

wherein
X is independently O or S;
W and Z is independently absent or O, S, or substituted or unsubstituted alkylene;
Y is O, S, or NR;
the dotted line represents an optional double bond if valence permits;
$R_1$ is independently hydrogen; hydroxy (—OH), thiol (—SH), substituted or unsubstituted alkyl, substituted or unsubstituted alkene, substituted or unsubstituted oligo- or polyether, substituted or unsubstituted primary amine, substituted or unsubstituted secondary amine, substituted or unsubstituted tertiary amine, —C(O)R or —C(O)OR, where R is hydrogen, halogen, substituted or unsubstituted alkyl or heteroalkyl, substituted or unsubstituted cycloalkyl or heterocycloalkyl, substituted or unsubstituted aryl or heteroaryl, or halogen; substituted or unsubstituted primary amide, substituted or unsubstituted secondary amide, substituted or unsubstituted tertiary amide, substituted or unsubstituted secondary carbamate, substituted or unsubstituted tertiary carbamate, substituted or unsubstituted urea, sulfinyl group, sulfonyl group, sulfino group, halogen, nitrile, $CF_3$, substituted or unsubstituted alkyl, substituted or unsubstituted cycloalkyl, substituted or unsubstituted heterocycloalkyl, substituted or unsubstituted alkylaryl, substituted or unsubstituted alkenyl, substituted or unsubstituted alkynyl, substituted or unsubstituted aryl, or substituted or unsubstituted heteroaryl group;

$R_2$ is selected from $NR_{12}$—CO—$(CH_2)_nR_{13}$, $NR_{12}$—$SO_2$—$(CH_2)_nR_{13}$, $COR_{13}$, $(CH_2)_nR_{13}$, C≡C—$(CH_2)_nNR_{12}$—CO—$(CH_2)_oR_{13}$, CO—$NR_{12}(CH_2)_n(CH_2CH_2O)_mR_{13}$, $NR_{12}$—CO—$(CH_2)_n(CH_2CH_2O)_mR_{13}$, and —$(CR_{14}R_{15})_nCOR_{13}$, wherein n and m are integers from 0-10, preferably 0-6, such as 0, 1, 2, or 3, R is hydrogen, halogen, hydroxy, —OR, nitro, cyano, alkyl, or aryl, $R_{12}$ is hydrogen, alkyl, or aryl, and $R_{13}$ is hydrogen or a leaving group, a reactive functional group, an electrophilic group, a Michael acceptor, or a moiety containing the same; and $R_3$-$R_{11}$ are independently hydrogen; hydroxy (—OH), thiol (—SH), ether, thioether, primary amine, secondary amine, tertiary amine, aldehyde, ketone, ester, carboxylic acid, primary amide, secondary amide, tertiary amide, secondary carbamate, tertiary carbamate, urea, sulfinyl group, sulfonyl group, sulfino group, phosphate, phosphinate, phosphonate, nitro, halogen, nitrile, $CF_3$, or substituted or unsubstituted alkyl, heteroalkyl, cycloalkyl, heterocycloalkyl, alkenyl, alkynyl, aryl or heteroaryl, or alkylaryl or alkylheteroaryl group.

In some embodiments, X, W, and Z are O and Y is N.
In some embodiments, X and Z are O, Z is N, and W is absent.
In some embodiments, X, W, Z, and Y are as defined above and $R_1$ is hydrogen, substituted or unsubstituted alkyl (e.g., methyl, ethyl, propyl, isopropyl, isobutyl, $(CH_2)_3N_3$, etc.), substituted or unsubstituted alkenyl (e.g., propenyl), substituted or unsubstituted aryl or alkyl aryl (e.g., benzyl).

In some embodiments, X, Y, W, Z, and $R_1$-$R_{11}$ are as defined above, n is 0-3, m is 1, and $R_{13}$ is selected from hydrogen or a reactive functional group, a leaving group, or a Michael acceptor, such as halogen (e.g., chlorine, bromine, iodine, and fluorine), azide, cyano, alkoxy or aroxy (e.g., methoxy, benzyloxy), trifluoromethyl, vinyl groups or vinyl-containing groups, hydroxy, amino, or primary, secondary, or tertiary amine.

In some embodiments, X, Y, W, Z, $R_1$-$R_{11}$, and n are as defined above m is 2, and $R_{13}$ is as defined above. In some embodiments, U is halogen (e.g., chlorine, bromine, iodine, and fluorine).

The compounds can be formulated with one or more pharmaceutically acceptable excipients to prepare pharmaceutical compositions. The compositions contain an effective amount of the compound or compounds to inhibit cell proliferation, particularly cancer cell proliferation, and/or to cause cell death, particularly cancer cell death.

BRIEF DESCRIPTION OF THE DRAWINGS

FIGS. 2a-2i are graphs showing the cytotoxicity of various Rhein analogues. Acute lymphoblastic leukemia (ALL) cell lines EU-1 (p53 normal) and EU-8 (p53 null) as well as normal human BM stroma cells were incubated with different concentrations of Rhein analogues as indicated for 24 h. Viability of cells was detected by Water soluble Tetrazolium (WST) dye assay. Data represent the mean percentage ±SD of the surviving cells (as compared to untreated controls) from three independent experiments.

FIG. 5A is a comparison of colony numbers, *p<0.01.

FIG. 6 is a table showing the estimated treatment doses and maximum tolerated dose (MTD) of MG1 in mice as compared with doxorubicin.

DETAILED DESCRIPTION OF THE INVENTION

I. Definitions

Figure 1A:
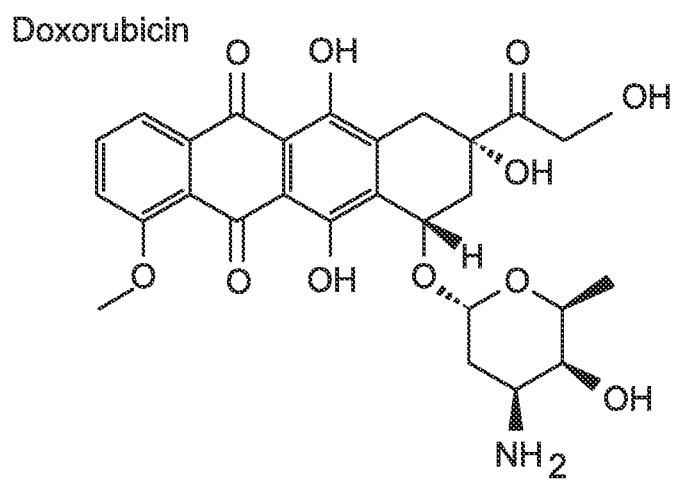
FIG. 1 is a table showing a variety of Rhein analogs and their molecular weights.

An "effective amount", e.g., of the compounds described herein, refers to an amount of the compound in a composition or formulation which, when applied as part of a desired dosage regimen brings about, e.g., a change in the rate of cell proliferation and/or the state of differentiation of a cell and/or rate of survival of a cell according to clinically acceptable standards for the disorder to be treated.

The "growth state" of a cell refers to the rate of proliferation of the cell and/or the state of differentiation of the cell. An "altered growth state" is a growth state characterized by an abnormal rate of proliferation, e.g., a cell exhibiting an increased or decreased rate of proliferation relative to a normal cell.

As used herein, "proliferating" and "proliferation" refer to cells undergoing mitosis.

The term "patient" or "subject" to be treated refers to either a human or non-human animal.

"Half maximal inhibitory concentration, $IC_{50}$", as used herein, refers to a measure of the effectiveness of a compound in inhibiting biological or biochemical function. This quantitative measure indicates how much of a particular drug or other substance (inhibitor) is needed to inhibit a given biological process (or component of a process, i.e. an enzyme, cell, cell receptor or microorganism) by half. According to the FDA, $IC_{50}$ represents the concentration of a drug that is required for 50% inhibition in vitro. The $IC_{50}$ can be determined using a variety of assays known in the art.

"Analog" and "Derivative", are used herein interchangeably, and refer to a compound that possesses the same tricyclic core as the parent compound Rhein, but differs from the parent compound in bond order, in the absence or presence of one or more atoms and/or groups of atoms, and combinations thereof. The derivative can differ from the parent compound, for example, in one or more substituents present on the tricyclic core, which may include one or more atoms, functional groups, or substructures. The derivative can also differ from the parent compound in the bond order between atoms within the tricyclic core. In general, a derivative can be imagined to be formed, at least theoretically, from the parent compound via chemical and/or physical processes.

"Alkylating group" or "alkylating moiety" are used interchangeably and refer to one or more functional groups or moieties that react with DNA, particularly DNA in cancer cells, to alkylate the DNA. Alkylating groups or moieties are typically classified as nucleophilic alkylating groups or moieties (wherein the alkyl group is transferred as a carbanion) and electrophilic alkylating groups or moieties (wherein the alkyl group is transferred as carbocation or as a partial positive group). In some embodiments, the alkylating group or moiety is electrophilic.

"Electrophilic group" or "electrophilic moiety" are used interchangeably and refer to one or more functional groups or moieties that have an affinity for or attract electrons.

"Michael Acceptor", as used herein, is species of electrophilic groups or moieties that participates in nucleophilic addition reactions. The Michael acceptor can be or can contain an α,β-unsaturated carbonyl-containing group or moiety, such as a ketone. Other acceptors include pi bonds, such as double or triple bonds conjugated to other pi bond-containing electron withdrawing groups, such as nitro groups, nitrile groups, and carboxylic acid groups.

"Reactive functional group", as used herein, refers to a functional group is itself is reactive or can be converted into a reactive group. For example, hydroxy groups are not considered good leaving groups. However, hydroxyl groups can be esterified or otherwise modified (e.g., triflate) to form a better leaving group.

"Co-administration", as used herein, includes simultaneous and sequential administration. An appropriate time course for sequential administration may be chosen by the physician, according to such factors as the nature of a patient's illness, and the patient's condition.

"Pharmaceutically acceptable", as used herein, refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

"Prodrug", as used herein, refers to a pharmacological substance (drug) that is administered to a subject in an inactive (or significantly less active) form. Once administered, the prodrug is metabolized in the body (in vivo) into a compound having the desired pharmacological activity. Examples include, but are not limited to, esters (generated from hydroxy and carboxylic acid groups), sulfates and phosphates (generated from hydroxy groups on the drug), amides, imines, and carbonates (generated from amino groups on the drug), and imines, oximes, acetals, enol esters, oxazolidines, and thiazolidines (generated from aldehydes and ketones on the drug).

"Alkyl", as used herein, refers to the radical of saturated or unsaturated aliphatic groups, including straight-chain alkyl, alkenyl, or alkynyl groups, branched-chain alkyl, alkenyl, or alkynyl groups, cycloalkyl, cycloalkenyl, or cycloalkynyl (alicyclic) groups, alkyl substituted cycloalkyl, cycloalkenyl, or cycloalkynyl groups, and cycloalkyl substituted alkyl, alkenyl, or alkynyl groups. Unless otherwise indicated, a straight chain or branched chain alkyl has 30 or fewer carbon atoms in its backbone (e.g., $C_1$-$C_{30}$ for straight chain, $C_3$-$C_{30}$ for branched chain), more preferably 20 or fewer carbon atoms, more preferably 12 or fewer carbon atoms, and most preferably 8 or fewer carbon atoms. In some embodiments, the chain has 1-6 carbons. Likewise, preferred cycloalkyls have from 3-10 carbon atoms in their ring structure, and more preferably have 5, 6 or 7 carbons in the ring structure. The ranges provided above are inclusive of all values between the minimum value and the maximum value.

The term "alkyl" includes both "unsubstituted alkyls" and "substituted alkyls", the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls.

The alkyl groups may also contain one or more heteroatoms within the carbon backbone. Examples include oxygen, nitrogen, sulfur, and combinations thereof. In certain embodiments, the alkyl group contains between one and four heteroatoms.

"Alkenyl" and "Alkynyl", as used herein, refer to unsaturated aliphatic groups containing one or more double or triple bonds analogous in length (e.g., $C_2$-$C_{30}$) and possible substitution to the alkyl groups described above.

"Aryl", as used herein, refers to 5-, 6- and 7-membered aromatic rings. The ring may be a carbocyclic, heterocyclic, fused carbocyclic, fused heterocyclic, bicarbocyclic, or biheterocyclic ring system, optionally substituted as described above for alkyl. Broadly defined, "Ar", as used herein, includes 5-, 6- and 7-membered single-ring aromatic groups that may include from zero to four heteroatoms. Examples include, but are not limited to, benzene, pyrrole, furan, thiophene, imidazole, oxazole, thiazole, triazole, pyrazole, pyridine, pyrazine, pyridazine and pyrimidine. Those aryl groups having heteroatoms in the ring structure may also be referred to as "heteroaryl", "aryl heterocycles", or "heteroaromatics". The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, and —CN. The term "Ar" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocycles, or both rings are aromatic. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

"Alkylaryl", as used herein, refers to an alkyl group substituted with an aryl group (e.g., an aromatic or hetero aromatic group).

"Heterocycle" or "heterocyclic", as used herein, refers to a cyclic radical attached via a ring carbon or nitrogen of a monocyclic or bicyclic ring containing 3-10 ring atoms, and preferably from 5-6 ring atoms, containing carbon and one to four heteroatoms each selected from non-peroxide oxygen, sulfur, and N(Y) wherein Y is absent or is H, O, ($C_{1-4}$) alkyl, phenyl or benzyl, and optionally containing one or more double or triple bonds, and optionally substituted with one or more substituents. The term "heterocycle" also encompasses substituted and unsubstituted heteroaryl rings. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

"Heteroaryl", as used herein, refers to a monocyclic aromatic ring containing five or six ring atoms containing carbon and 1, 2, 3, or 4 heteroatoms each selected from non-peroxide oxygen, sulfur, and N(Y) where Y is absent or is H, O, ($C_1$-$C_8$) alkyl, phenyl or benzyl. Non-limiting examples of heteroaryl groups include furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide), quinolyl (or its N-oxide) and the like. The term "heteroaryl" can include radicals of an ortho-fused bicyclic heterocycle of about eight to ten ring atoms derived therefrom, particularly a benz-derivative or one derived by fusing a propylene, trimethylene, or tetramethylene diradical thereto. Examples of heteroaryl include, but are not limited to, furyl, imidazolyl, triazolyl, triazinyl, oxazoyl, isoxazoyl, thiazolyl, isothiazoyl, pyraxolyl, pyrrolyl, pyrazinyl, tetrazolyl, pyridyl (or its N-oxide), thientyl, pyrimidinyl (or its N-oxide), indolyl, isoquinolyl (or its N-oxide), quinolyl (or its N-oxide), and the like.

"Halogen", as used herein, refers to fluorine, chlorine, bromine, or iodine.

The term "substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, aminoacid, peptide, and polypeptide groups.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

II. Compounds

Rhein analogues that exhibit anti-proliferative activity, particular against cancer cells, are described herein. In some embodiments, the compounds contain a flat or planar ring system. Such rings system by facilitate non-covalent binding of the compounds to the DNA complex, such as by intercalation. In some embodiment, the compounds contain a flat or planar ring system as described above and one or more substituents which are alkylating moieties, electrophilic groups or Michael acceptors or groups which contain one or more alkylating moieties, electrophilic groups and/or Michael acceptors. In particular embodiments, the alkylating moiety or moieties are found at the 3-position of the anthraquinone core. However, these moieties can be found at other locations including $R_1$ and $R_8$ as well as one or more positions on the cyclic core.

Examples of alkylating moieties include, but are not limited to, leaving groups (e.g., halogens, esters, etc) which are replaced by a nucleophilic group in substitutions reactions and electrophilic groups including Michael addition acceptors, such as α,β-unsaturated carbonyl-containing moieties, and combinations thereof. Specific Michael acceptors include, but not limited to, acrylates, itaconates, itaconamides, vinylsulfones and/or acrylamides.

The compounds described herein can also contain one more functional groups to improve the solubility of the compounds. For example, an oligo- or polyethylene glycol moiety can incorporated into one or more side chains on the rhein core to improve solubility. Other functional groups which can improve solubility include groups that are charged or become charged under physiological conditions, such as amines, sulfates, sulfonates, sulfonates, phosphates, phosphinates, phosphonates, carboxylic acid groups, etc. In some embodiments, the one or more functional groups to improve solubility are moieties in $R_3$. In other embodiments, the functional groups to improve solubility are moieties in other positions in the molecule, such as $R_1$ and $R_8$ and/or on positions on the cyclic core.

In some embodiments, the compounds have the formula:

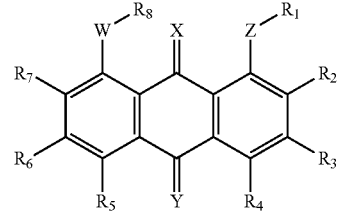

wherein

X and Y are independently O or S;

W and Z are independently absent or O, S, or substituted or unsubstituted alkylene;

$R_1$ and $R_8$ are independently hydrogen; hydroxy (—OH), thiol (—SH), substituted or unsubstituted alkyl, substituted or unsubstituted oligo- or polyether, substituted or unsubstituted primary amine, substituted or unsubstituted secondary amine, substituted or unsubstituted tertiary amine, —C(O)R or —C(O)OR, where R is hydrogen, halogen, substituted or unsubstituted alkyl or heteroalkyl, substituted or unsubstituted cycloalkyl or heterocycloalkyl, substituted or unsubstituted aryl or heteroaryl, or halogen; substituted or unsubstituted primary amide, substituted or unsubstituted secondary amide, substituted or unsubstituted tertiary amide, substituted or unsubstituted secondary carbamate, substituted or unsubstituted tertiary carbamate, substituted or unsubstituted urea, sulfinyl group, sulfonyl group, sulfino group, halogen, nitrile, $CF_3$, substituted or unsubstituted alkyl, substituted or unsubstituted cycloalkyl, substituted or unsubstituted heterocycloalkyl, substituted or unsubstituted alkylaryl, substituted or unsubstituted alkenyl, substituted or unsubstituted alkynyl, substituted or unsubstituted aryl, or substituted or unsubstituted heteroaryl group;

$R_3$ is halogen, substituted or unsubstituted alky or cycloalkyl, substituted or unsubstituted aryl; substituted or unsubstituted heteroaryl; M-Ar or M-hetAr, where Ar is substituted or unsubstituted aryl, hetAr is substituted or unsubstituted heteroaryl, and M is O, S, or $NR_9$; $N(R_9)_2$, CO—$NR_9(CH_2)_n(CH_2CH_2O)_mR_{10}$, $NR_9$—CO—$(CH_2)_n$ $(CH_2CH_2O)_mR_{10}$, $NR_9$—CO—$(CH_2)_nR_{10}$, —$(CR_{12}R_{13})_n$ $COR_{10}$, $NR_9$—$SO_2$—$(CH_2)_nR_{10}$, C≡C—$(CH_2)_nNR_9$— CO—$(CH_2)_oR_{10}$, $(CH_2)_nR_{10}$, or $COR_{10}$; wherein n, m, and o are independently an integer from 0-10, preferably 0-6, more preferably from 1-6, each occurrence of $R_9$ is independently hydrogen, alkyl, or aryl, and $R_{10}$ is hydrogen, substituted or unsubstituted alkyl or cycloalkyl, substituted or unsubstituted alkenyl or alkynyl, substituted or unsubstituted aryl or heteroaryl, or a leaving group, electrophilic group, reactive functional group, or Michael acceptor or a moiety containing a leaving group, electrophilic group, reactive functional group, or Michael acceptor;

$R_2$ and $R_4$-$R_7$ are independently hydrogen; hydroxy (—OH), thiol (—SH), ether, thioether, primary amine, secondary amine, tertiary amine, aldehyde, ketone, ester, carboxylic acid, primary amide, secondary amide, tertiary amide, secondary carbamate, tertiary carbamate, urea, sulfinyl group, sulfonyl group, sulfino group, phosphate, phosphinate, phosphonate, nitro, halogen, nitrile, $CF_3$, or substituted or unsubstituted alkyl, heteroalkyl, cycloalkyl, heterocycloalkyl, alkenyl, alkynyl, aryl or heteroaryl, or alkylaryl or alkylheteroaryl group.

In some embodiments, X, Y, W, and Z are oxygen.

In some embodiments, X, Y, W, and Z are oxygen and $R_1$ and $R_8$ are hydrogen, substituted or unsubstituted lower alkyl, such as methyl, ethyl, propyl (e.g., n-propyl or isobutyl), or butyl (e.g., n-butyl, isobutyl, sec-butyl, or t-butyl), substituted or unsubstituted lower alkenyl (e.g., propenyl), substituted or unsubstituted aryl, alkylaryl, arylalkyl (e.g., benzyl).

In some embodiments, X, Y, W, Z, $R_1$, and/or $R_8$ are as defined above and $R_2$ and $R_4$-$R_7$ are hydrogen.

In some embodiments, X, Y, W, and Z are oxygen, $R_1$ and $R_8$ are hydrogen, $R_2$ and $R_4$-$R_7$ are hydrogen, In some embodiments, X, Y, W, and Z are oxygen, $R_1$ and $R_8$ are substituted or unsubstituted alkyl, alkenyl, aryl, alkylaryl or aryalkyl, and $R_2$ and $R_4$-$R_7$ are hydrogen.

In some embodiments, X, Y, W, Z, $R_1$, and/or $R_8$ are as defined above and $R_3$ is NH—CO—$(CH_2)_n R_{10}$, wherein n is an integer from 0-10, preferably 0, 1, 2, or 3, and $R_{10}$ is hydrogen or a leaving group, a reactive functional group, an electrophilic group, a Michael acceptor, or a moiety containing the same and m is an integer from 0-3.

In some embodiments, X, Y, W, Z, $R_1$, and/or $R_8$ are as defined above and $R_3$ is NH—$SO_2$—$(CH_2)_n R_{10}$, wherein n is an integer from 0-10, preferably 0, 1, 2, or 3, and $R_{10}$ is hydrogen or a leaving group, a reactive functional group, an electrophilic group, a Michael acceptor, or a moiety containing the same, and m is an integer from 0-3.

In some embodiments, X, Y, W, Z, $R_1$, and/or $R_8$ are as defined above and $R_3$ is C≡C—$(CH_2)_n$NH—CO—$(CH_2)_o$ $R_{10}$, wherein n is an integer from 0-10, preferably 0, 1, 2, or 3, and $R_{10}$ is hydrogen or a leaving group, a reactive functional group, an electrophilic group, a Michael acceptor, or a moiety containing the same, and m is an integer from 0-3.

In some embodiments, X, Y, W, Z, $R_1$, and/or $R_8$ are as defined above and $R_3$ is $(CH_2)_n R_{10}$, wherein n is an integer from 0-10, preferably 0, 1, 2, or 3, $R_{10}$ is hydrogen or a leaving group, a reactive functional group, an electrophilic group, a Michael acceptor, or a moiety containing the same, and m is an integer from 0-3.

In some embodiments, X, Y, W, Z, $R_1$, and/or $R_8$ are as defined above and $R_3$ is $COR_{10}$, wherein $R_{10}$ is hydrogen or a leaving group, a reactive functional group, an electrophilic group, a Michael acceptor, or a moiety containing the same, and m is an integer from 0-3.

In some embodiments, X, Y, W, Z, $R_1$, $R_8$, and/or $R_3$ are as defined above and $R_{10}$ is hydrogen or a leaving group, electrophilic group, reactive functional group or Michael acceptor, such as halogen, azide, cyano, alkoxy or aroxy, trifluoromethyl, vinyl group or vinyl-containing group, hydroxy, amino, primary or secondary amine, or protected amine, such as Boc-protected amine.

In some embodiments, X, Y, W, Z, $R_1$, $R_8$, and/or $R_3$ are as defined above and $R_{10}$ is $(CH_2)_p NHCO(CH_2)_q$halogen or $(CH_2)_p NHCO(CH_2)_q NH_2$, wherein p and q are independently integers from about 1-6, preferably from about 1-3.

In some embodiments, X, Y, W, and Z are O.

In some embodiments, X and Y are O and W and Z are absent.

In some embodiments, X, Y, W, and Z are as defined above, and $R_1$ and $R_8$ are hydrogen, substituted or unsubstituted alkyl (e.g., methyl, ethyl, propyl, isopropyl, isobutyl, $(CH_2)_3 N_3$, etc.), substituted or unsubstituted alkenyl (e.g., propenyl), substituted or unsubstituted aryl or alkyl aryl (e.g., benzyl)

In some embodiments, X, Y, W, Z, and $R_1$-$R_{10}$ are as defined above, n is 0-3, m is 1, and U is selected from hydrogen or a reactive functional group, a leaving group, an electrophilic group, or a Michael acceptor, such as halogen (e.g., chlorine, bromine, iodine, and fluorine), azide, cyano, alkoxy or aroxy (e.g., methoxy, benzyloxy), trifluoromethyl, vinyl groups or vinyl-containing groups, hydroxy, amino, or primary, secondary, or tertiary amine.

A single $R_{10}$ or multiple $R_{10}$ groups can be present. For example, $R_{10}$ in the substituent $R_3$ can be represented at $(R_{10})_a$ where a is a variable from 0-3, preferably 1 or 2. In some embodiments, X, Y, W, Z, $R_1$-$R_{10}$, and n are as defined above, $R_{10}$ is as defined above, and a is 2. In some embodiments, $R_{10}$ is halogen (e.g., chlorine, bromine, iodine, and fluorine).

Examples of the compounds described above are shown in FIGS. 1 and 10-17.

In other embodiments, X, Y, W, and Z are oxygen, $R_1$ and $R_8$ are hydrogen, $R_2$ and $R_4$-$R_7$ are hydrogen, and $R_3$ is $NHCO(CH_2)_n R$, where n is an integer from 1-10, preferably 1-6, more preferably from 1-3, such as 1, and R is a primary amine (e.g., $NH_2$), secondary amine (e.g., NHR'), or tertiary amine (e.g., NR'R") or a substituted or unsubstituted heterocycloalkyl, such as piperidine, piperazine, or morpholine.

Examples of these compounds are shown below:

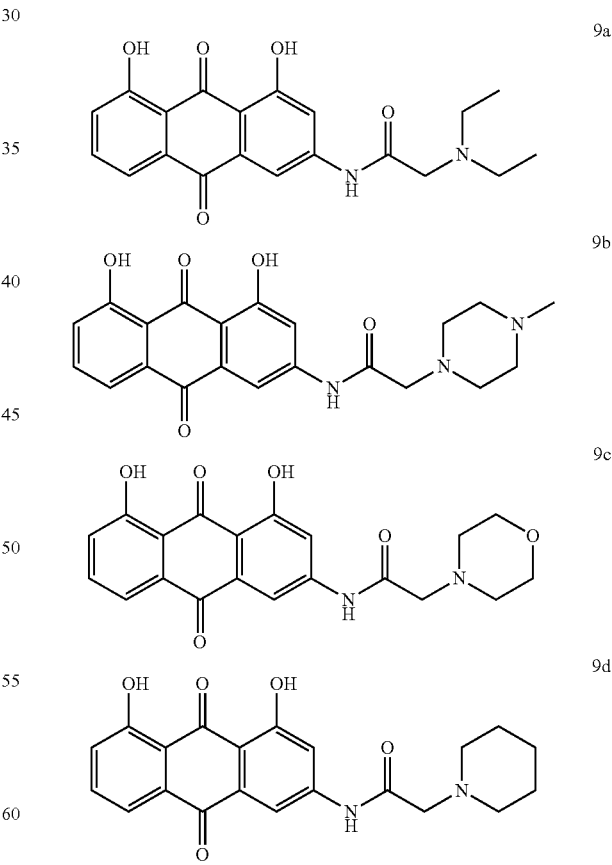

In other embodiments, $R_1$ and $R_8$ are hydrogen or lower alkyl and $R_3$ is a halogen or substituted or unsubstituted aromatic or heteroaromatic. Examples of these compounds are shown in Table 1.

TABLE 1

Demethylation reactions for Series 1 Rhein analogues synthesis

| Methylated | R group | Demethylated | R' group | Yield |
|---|---|---|---|---|
| 24 | —I | 24a | —S-Ph | 54% |
| 25a | 3,5-dimethylisoxazol-4-yl | 26a | 3,5-dimethylisoxazol-4-yl | 41% |
| 25b | thiophen-2-yl | 26b | thiophen-2-yl | 47% |
| 25c | 4-(dimethylamino)-3-methylphenyl | 26c | 4-(dimethylamino)-3-methylphenyl | 71% |
| 25d | 6-fluoropyridin-3-yl | 26d | 6-(phenylthio)pyridin-3-yl | 47% |
| 25e | 4-((tert-butoxy)methyl)phenyl | 26e | 4-((tert-butoxy)methyl)phenyl | 78% |
| 25f | 4-methoxyphenyl | 26f | 4-methoxyphenyl | 61% |
| 26f | 4-methoxyphenyl | 26g | 4-hydroxyphenyl | 28% |
| 25g | 4-acetylphenyl | — | NA | NA |
| 25h | furan-2-yl | — | NA | NA |

TABLE 1-continued

Demethylation reactions for Series 1 Rhein analogues synthesis

| Methylated | R group | Demethylated | R' group | Yield |
|---|---|---|---|---|
| 25i | 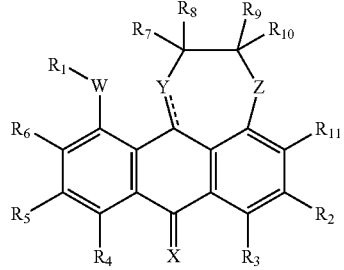 | — | NA | NA |

In some embodiments, the compound is not a compound in Table for compounds 9a-9d above. In some embodiments, the compound is not a compound wherein W and Z are O, $R_1$ and $R_8$ are methyl, and $R_3$ is amino ($NH_2$). In some embodiments, the compound is not a compound wherein W and Z are O, $R_1$ and $R_8$ are hydrogen or methyl, and $R_3$ is $NHCOCH_2$halogen. In some embodiments, the compound is not a compound wherein W and Z are O, $R_1$ and $R_8$ are hydrogen, and $R_3$ is $CONH(CH_2)_4NH_2$ or $CONH(CH_2)_4NHCOCH_2$halogen, wherein halogen is Br or Cl. In some embodiments, the compound is not a compound wherein W and Z are O, $R_1$ and $R_8$ are hydrogen, and $R_3$ is $CONH(CH_2)_3(OCH_2CH_2)_3CH_2NH_2$ or $CONH(CH_2)_3(OCH_2CH_2)_3CH_2COCH_2$halogen, wherein halogen is Br, Cl, or I.

In other embodiments, the compound has the formula:

[Structure with $R_1$–$R_{11}$, W, X, Y, Z]

wherein

X is independently O or S;

W and Z is independently absent or O, S, or substituted or unsubstituted alkylene;

Y is O, S, or NR;

the dotted line represents an optional double bond if valence permits;

$R_1$ is independently hydrogen; hydroxy (—OH), thiol (—SH), substituted or unsubstituted alkyl, substituted or unsubstituted alkene, substituted or unsubstituted oligo- or polyether, substituted or unsubstituted primary amine, substituted or unsubstituted secondary amine, substituted or unsubstituted tertiary amine, —C(O)R or —C(O)OR, where R is hydrogen, halogen, substituted or unsubstituted alkyl or heteroalkyl, substituted or unsubstituted cycloalkyl or heterocycloalkyl, substituted or unsubstituted aryl or heteroaryl, or halogen; substituted or unsubstituted primary amide, substituted or unsubstituted secondary amide, substituted or unsubstituted tertiary amide, substituted or unsubstituted secondary carbamate, substituted or unsubstituted tertiary carbamate, substituted or unsubstituted urea, sulfinyl group, sulfonyl group, sulfino group, halogen, nitrile, $CF_3$, substituted or unsubstituted alkyl, substituted or unsubstituted cycloalkyl, substituted or unsubstituted heterocycloalkyl, substituted or unsubstituted alkylaryl, substituted or unsubstituted alkenyl, substituted or unsubstituted alkynyl, substituted or unsubstituted aryl, or substituted or unsubstituted heteroaryl group;

$R_2$ is selected from $NR_{12}$—CO—$(CH_2)_nR_{13}$, $NR_{12}$—$SO_2$—$(CH_2)_nR_{13}$, $COR_{13}$, $(CH_2)_nR_{13}$, $C\equiv C$—$(CH_2)_nNR_{12}$—CO—$(CH_2)_oR_{13}$, CO—$NR_{12}(CH_2)_n(CH_2CH_2O)_mR_{13}$, $NR_{12}$—CO—$(CH_2)_n(CH_2CH_2O)_mR_{13}$, and —$(CR_{14}R_{15})_nCOR_{13}$, wherein n and m are integers from 0-10, preferably 0-6, such as 0, 1, 2, or 3, R is hydrogen, halogen, hydroxy, —OR, nitro, cyano, alkyl, or aryl, $R_{12}$ is hydrogen, alkyl, or aryl, and $R_{13}$ is hydrogen or a leaving group, a reactive functional group, an electrophilic group, a Michael acceptor, or a moiety containing the same; and $R_3$-$R_{11}$ are independently hydrogen; hydroxy (—OH), thiol (—SH), ether, thioether, primary amine, secondary amine, tertiary amine, aldehyde, ketone, ester, carboxylic acid, primary amide, secondary amide, tertiary amide, secondary carbamate, tertiary carbamate, urea, sulfinyl group, sulfonyl group, sulfino group, phosphate, phosphinate, phosphonate, nitro, halogen, nitrile, $CF_3$, or substituted or unsubstituted alkyl, heteroalkyl, cycloalkyl, heterocycloalkyl, alkenyl, alkynyl, aryl or heteroaryl, or alkylaryl or alkylheteroaryl group.

In some embodiments, X, W, and Z are O and Y is N.

In some embodiments, X and Z are O, Z is N, and W is absent.

In some embodiments, X, W, Z, and Y are as defined above and $R_1$ is hydrogen, substituted or unsubstituted alkyl (e.g., methyl, ethyl, propyl, isopropyl, isobutyl, $(CH_2)_3N_3$, etc.), substituted or unsubstituted alkenyl (e.g., propenyl), substituted or unsubstituted aryl or alkyl aryl (e.g., benzyl).

In some embodiments, X, Y, W, Z, and $R_1$-$R_{11}$ are as defined above, n is 0-3, m is 1, and $R_{13}$ is selected from hydrogen or a reactive functional group, a leaving group, or a Michael acceptor, such as halogen (e.g., chlorine, bromine, iodine, and fluorine), azide, cyano, alkoxy or aroxy (e.g., methoxy, benzyloxy), trifluoromethyl, vinyl groups or vinyl-containing groups, hydroxy, amino, or primary, secondary, or tertiary amine.

In some embodiments, X, Y, W, Z, $R_1$-$R_{11}$, and n are as defined above m is 2, and $R_{13}$ is as defined above. In some embodiments, U is halogen (e.g., chlorine, bromine, iodine, and fluorine).

III. Pharmaceutical Compositions

The compounds described herein can be formulated for enteral, parenteral, topical, or pulmonary administration. The compounds can be combined with one or more pharmaceutically acceptable carriers and/or excipients that are considered safe and effective and may be administered to an individual without causing undesirable biological side effects or unwanted interactions. The carrier is all components present in the pharmaceutical formulation other than the active ingredient or ingredients.

A. Parenteral Formulations

The compounds described herein can be formulated for parenteral administration. "Parenteral administration", as used herein, means administration by any method other than through the digestive tract or non-invasive topical or regional routes. For example, parenteral administration may include administration to a patient intravenously, intradermally, intraarterially, intraperitoneally, intralesionally, intracranially, intraarticularly, intraprostatically, intrapleurally, intratracheally, intravitreally, intratumorally, intramuscularly, subcutaneously, subconjunctivally, intravesicularly, intrapericardially, intraumbilically, by injection, and by infusion.

Parenteral formulations can be prepared as aqueous compositions using techniques is known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the active compounds as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, viscosity modifying agents, and combination thereof.

Suitable surfactants may be anionic, cationic, amphoteric or nonionic surface-active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for parenteral administration upon reconstitution. Suitable buffers include, but are not limited to, phosphate buffers, acetate buffers, and citrate buffers.

Water-soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the active compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The powders can be prepared in such a manner that the particles are porous in nature, which can increase dissolution of the particles. Methods for making porous particles are well known in the art.

1. Controlled Release Formulations

The parenteral formulations described herein can be formulated for controlled release including immediate release, delayed release, extended release, pulsatile release, and combinations thereof.

i. Nano- and Microparticles

For parenteral administration, the one or more compounds, and optional one or more additional active agents, can be incorporated into microparticles, nanoparticles, or combinations thereof that provide controlled release of the compounds and/or one or more additional active agents. In embodiments wherein the formulations contains two or more drugs, the drugs can be formulated for the same type of controlled release (e.g., delayed, extended, immediate, or pulsatile) or the drugs can be independently formulated for different types of release (e.g., immediate and delayed, immediate and extended, delayed and extended, delayed and pulsatile, etc.).

For example, the compounds and/or one or more additional active agents can be incorporated into polymeric microparticles, which provide controlled release of the drug(s). Release of the drug(s) is controlled by diffusion of the drug(s) out of the microparticles and/or degradation of the polymeric particles by hydrolysis and/or enzymatic degradation. Suitable polymers include ethylcellulose and other natural or synthetic cellulose derivatives.

Polymers, which are slowly soluble and form a gel in an aqueous environment, such as hydroxypropyl methylcellulose or polyethylene oxide, may also be suitable as materials for drug containing microparticles. Other polymers include, but are not limited to, polyanhydrides, poly(ester anhydrides), polyhydroxy acids, such as polylactide (PLA), polyglycolide (PGA), poly(lactide-co-glycolide) (PLGA), poly-3-hydroxybutyrate (PHB) and copolymers thereof, poly-4-hydroxybutyrate (P4HB) and copolymers thereof, polycaprolactone and copolymers thereof, and combinations thereof.

Alternatively, the drug(s) can be incorporated into microparticles prepared from materials which are insoluble in aqueous solution or slowly soluble in aqueous solution, but are capable of degrading within the GI tract by means including enzymatic degradation, surfactant action of bile acids, and/or mechanical erosion. As used herein, the term "slowly soluble in water" refers to materials that are not dissolved in water within a period of 30 minutes. Preferred examples include fats, fatty substances, waxes, wax-like substances and mixtures thereof. Suitable fats and fatty substances include fatty alcohols (such as lauryl, myristyl stearyl, cetyl or cetostearyl alcohol), fatty acids and derivatives, including but not limited to fatty acid esters, fatty acid glycerides (mono-, di- and tri-glycerides), and hydrogenated fats. Specific examples include, but are not limited to hydrogenated vegetable oil, hydrogenated cottonseed oil, hydrogenated castor oil, hydrogenated oils available under the trade name Sterotex®, stearic acid, cocoa butter, and stearyl alcohol. Suitable waxes and wax-like materials include natural or synthetic waxes, hydrocarbons, and normal waxes. Specific examples of waxes include beeswax, glycowax, castor wax, carnauba wax, paraffins and candelilla wax. As used herein, a wax-like material is defined as any material, which is normally solid at room temperature and has a melting point of from about 30 to 300° C.

In some cases, it may be desirable to alter the rate of water penetration into the microparticles. To this end, rate-controlling (wicking) agents may be formulated along with the fats or waxes listed above. Examples of rate-controlling materials include certain starch derivatives (e.g., waxy maltodextrin and drum dried corn starch), cellulose derivatives (e.g., hydroxypropylmethyl-cellulose, hydroxypropyl-cellulose, methylcellulose, and carboxymethyl-cellulose), alginic acid, lactose and talc. Additionally, a pharmaceutically acceptable surfactant (for example, lecithin) may be added to facilitate the degradation of such microparticles.

Proteins, which are water insoluble, such as zein, can also be used as materials for the formation of drug containing microparticles. Additionally, proteins, polysaccharides and combinations thereof, which are water-soluble, can be formulated with drug into microparticles and subsequently cross-linked to form an insoluble network. For example, cyclodextrins can be complexed with individual drug molecules and subsequently cross-linked.

Encapsulation or incorporation of drug into carrier materials to produce drug-containing microparticles can be achieved through known pharmaceutical formulation techniques. In the case of formulation in fats, waxes or wax-like materials, the carrier material is typically heated above its melting temperature and the drug is added to form a mixture comprising drug particles suspended in the carrier material, drug dissolved in the carrier material, or a mixture thereof. Microparticles can be subsequently formulated through several methods including, but not limited to, the processes of congealing, extrusion, spray chilling or aqueous dispersion. In a preferred process, wax is heated above its melting temperature, drug is added, and the molten wax-drug mixture is congealed under constant stirring as the mixture cools. Alternatively, the molten wax-drug mixture can be extruded and spheronized to form pellets or beads. These processes are known in the art.

For some carrier materials it may be desirable to use a solvent evaporation technique to produce drug-containing microparticles. In this case drug and carrier material are co-dissolved in a mutual solvent and microparticles can subsequently be produced by several techniques including, but not limited to, forming an emulsion in water or other appropriate media, spray drying or by evaporating off the solvent from the bulk solution and milling the resulting material.

In some embodiments, drug in a particulate form is homogeneously dispersed in a water-insoluble or slowly water soluble material. To minimize the size of the drug particles within the composition, the drug powder itself may be milled to generate fine particles prior to formulation. The process of jet milling, known in the pharmaceutical art, can be used for this purpose. In some embodiments drug in a particulate form is homogeneously dispersed in a wax or wax like substance by heating the wax or wax like substance above its melting point and adding the drug particles while stirring the mixture. In this case a pharmaceutically acceptable surfactant may be added to the mixture to facilitate the dispersion of the drug particles.

The particles can also be coated with one or more modified release coatings. Solid esters of fatty acids, which are hydrolyzed by lipases, can be spray coated onto microparticles or drug particles. Zein is an example of a naturally water-insoluble protein. It can be coated onto drug containing microparticles or drug particles by spray coating or by wet granulation techniques. In addition to naturally water-insoluble materials, some substrates of digestive enzymes can be treated with cross-linking procedures, resulting in the formation of non-soluble networks. Many methods of cross-linking proteins, initiated by both chemical and physical means, have been reported. One of the most common methods to obtain cross-linking is the use of chemical cross-linking agents. Examples of chemical cross-linking agents include aldehydes (gluteraldehyde and formaldehyde), epoxy compounds, carbodiimides, and genipin. In addition to these cross-linking agents, oxidized and native sugars have been used to cross-link gelatin. Cross-linking can also be accomplished using enzymatic means; for example, transglutaminase has been approved as a GRAS substance for cross-linking seafood products. Finally, cross-linking can be initiated by physical means such as thermal treatment, UV irradiation and gamma irradiation.

To produce a coating layer of cross-linked protein surrounding drug containing microparticles or drug particles, a water-soluble protein can be spray coated onto the microparticles and subsequently cross-linked by the one of the methods described above. Alternatively, drug-containing microparticles can be microencapsulated within protein by coacervation-phase separation (for example, by the addition of salts) and subsequently cross-linked. Some suitable proteins for this purpose include gelatin, albumin, casein, and gluten.

Polysaccharides can also be cross-linked to form a water-insoluble network. For many polysaccharides, this can be accomplished by reaction with calcium salts or multivalent cations, which cross-link the main polymer chains. Pectin, alginate, dextran, amylose and guar gum are subject to cross-linking in the presence of multivalent cations. Complexes between oppositely charged polysaccharides can also be formed; pectin and chitosan, for example, can be complexed via electrostatic interactions.

In certain embodiments, it may be desirable to provide continuous delivery of one or more compounds to a patient in need thereof. For intravenous or intraarterial routes, this can be accomplished using drip systems, such as by intravenous administration. For topical applications, repeated application can be done or a patch can be used to provide continuous administration of the compounds over an extended period of time.

2. Injectable/Implantable Solid Implants

The compounds described herein can be incorporated into injectable/implantable solid or semi-solid implants, such as polymeric implants. In one embodiment, the compounds are incorporated into a polymer that is a liquid or paste at room temperature, but upon contact with aqueous medium, such as physiological fluids, exhibits an increase in viscosity to form a semi-solid or solid material. Exemplary polymers include, but are not limited to, hydroxyalkanoic acid polyesters derived from the copolymerization of at least one unsaturated hydroxy fatty acid copolymerized with hydroxyalkanoic acids. The polymer can be melted, mixed with the active substance and cast or injection molded into a device. Such melt fabrication require polymers having a melting point that is below the temperature at which the substance to be delivered and polymer degrade or become reactive. The device can also be prepared by solvent casting where the polymer is dissolved in a solvent and the drug dissolved or dispersed in the polymer solution and the solvent is then evaporated. Solvent processes require that the polymer be soluble in organic solvents. Another method is compression molding of a mixed powder of the polymer and the drug or polymer particles loaded with the active agent.

Alternatively, the compounds can be incorporated into a polymer matrix and molded, compressed, or extruded into a device that is a solid at room temperature. For example, the compounds can be incorporated into a biodegradable polymer, such as polyanhydrides, polyhydroalkanoic acids (PHAs), PLA, PGA, PLGA, polycaprolactone, polyesters, polyamides, polyorthoesters, polyphosphazenes, proteins and polysaccharides such as collagen, hyaluronic acid, albumin and gelatin, and combinations thereof and compressed into solid device, such as disks, or extruded into a device, such as rods.

The release of the one or more compounds from the implant can be varied by selection of the polymer, the molecular weight of the polymer, and/ir modification of the polymer to increase degradation, such as the formation of pores and/or incorporation of hydrolyzable linkages. Methods for modifying the properties of biodegradable polymers to vary the release profile of the compounds from the implant are well known in the art.

B. Enteral Formulations

Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art.

Formulations may be prepared using a pharmaceutically acceptable carrier. As generally used herein "carrier" includes, but is not limited to, diluents, preservatives, binders, lubricants, disintegrators, swelling agents, fillers, stabilizers, and combinations thereof.

Carrier also includes all components of the coating composition, which may include plasticizers, pigments, colorants, stabilizing agents, and glidants. Delayed release dosage formulations may be prepared as described in standard references. These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

Optional pharmaceutically acceptable excipients include, but are not limited to, diluents, binders, lubricants, disintegrants, colorants, stabilizers, and surfactants. Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone® XL from GAF Chemical Corp).

Stabilizers are used to inhibit or retard drug decomposition reactions, which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

i. Controlled Release Formulations

Oral dosage forms, such as capsules, tablets, solutions, and suspensions, can for formulated for controlled release. For example, the one or more compounds and optional one or more additional active agents can be formulated into nanoparticles, microparticles, and combinations thereof, and encapsulated in a soft or hard gelatin or non-gelatin capsule or dispersed in a dispersing medium to form an oral suspension or syrup. The particles can be formed of the drug and a controlled release polymer or matrix. Alternatively, the drug particles can be coated with one or more controlled release coatings prior to incorporation in to the finished dosage form.

In another embodiment, the one or more compounds and optional one or more additional active agents are dispersed in a matrix material, which gels or emulsifies upon contact with an aqueous medium, such as physiological fluids. In the case of gels, the matrix swells entrapping the active agents, which are released slowly over time by diffusion and/or degradation of the matrix material. Such matrices can be formulated as tablets or as fill materials for hard and soft capsules.

In still another embodiment, the one or more compounds, and optional one or more additional active agents are formulated into a sold oral dosage form, such as a tablet or capsule, and the solid dosage form is coated with one or more controlled release coatings, such as a delayed release coatings or extended release coatings. The coating or coatings may also contain the compounds and/or additional active agents.

Extended Release Dosage Forms

The extended release formulations are generally prepared as diffusion or osmotic systems, which are known in the art. A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, and Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain preferred embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers.

In certain preferred embodiments, the acrylic polymer is comprised of one or more ammonio methacrylate copolymers Ammonio methacrylate copolymers are well known in the art, and are described in NF XVII as fully polymerized copolymers of acrylic and methacrylic acid esters with a low content of quaternary ammonium groups.

In one preferred embodiment, the acrylic polymer is an acrylic resin lacquer such as that which is commercially available from Rohm Pharma under the tradename Eudragit®. In further preferred embodiments, the acrylic polymer comprises a mixture of two acrylic resin lacquers commercially available from Rohm Pharma under the tradenames Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. Edragit® S-100 and Eudragit® L-100 are also preferred. The code designations RL (high permeability) and RS (low permeability) refer to the permeability properties of these agents. Eudragit® RL/RS mixtures are insoluble in water and in digestive fluids. However, multiparticulate systems formed to include the same are swellable and permeable in aqueous solutions and digestive fluids.

The polymers described above such as Eudragit® RL/RS may be mixed together in any desired ratio in order to ultimately obtain a sustained-release formulation having a desirable dissolution profile. Desirable sustained-release multiparticulate systems may be obtained, for instance, from 100% Eudragit® RL, 50% Eudragit® RL and 50% Eudragit® RS, and 10% Eudragit® RL and 90% Eudragit® RS. One skilled in the art will recognize that other acrylic polymers may also be used, such as, for example, Eudragit® L.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above can be combined in a final dosage form comprising single or multiple units. Examples of multiple units include, but are not limited to, multilayer tablets and capsules containing tablets, beads, or granules.

An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

Delayed Release Dosage Forms

Delayed release formulations can be created by coating a solid dosage form with a polymer film, which is insoluble in the acidic environment of the stomach, and soluble in the neutral environment of the small intestine.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit® (Rohm Pharma; Westerstadt, Germany), including Eudragit® L30D-55 and L100-55 (soluble at pH 5.5 and above), Eudragit® L-100 (soluble at pH 6.0 and above), Eudragit® S (soluble at pH 7.0 and above, as a result of a higher degree of esterification), and Eudragits® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

C. Topical Formulations

Suitable dosage forms for topical administration include creams, ointments, salves, sprays, gels, lotions, emulsions, and transdermal patches. The formulation may be formulated for transmucosal, transepithelial, transendothelial, or transdermal administration. The compounds can also be formulated for intranasal delivery, pulmonary delivery, or inhalation. The compositions may further contain one or more chemical penetration enhancers, membrane permeability agents, membrane transport agents, emollients, surfactants, stabilizers, and combination thereof.

1. Topical Formulations

"Emollients" are an externally applied agent that softens or soothes skin and are generally known in the art and listed in compendia, such as the "Handbook of Pharmaceutical Excipients", $4^{th}$ Ed., Pharmaceutical Press, 2003. These include, without limitation, almond oil, castor oil, ceratonia extract, cetostearoyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In one embodiment, the emollients are ethylhexylstearate and ethylhexyl palmitate.

"Surfactants" are surface-active agents that lower surface tension and thereby increase the emulsifying, foaming, dispersing, spreading and wetting properties of a product. Suitable non-ionic surfactants include emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In one embodiment, the non-ionic surfactant is stearyl alcohol.

"Emulsifiers" are surface active substances which promote the suspension of one liquid in another and promote the formation of a stable mixture, or emulsion, of oil and water. Common emulsifiers are: metallic soaps, certain animal and vegetable oils, and various polar compounds. Suitable emulsifiers include acacia, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxpropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In one embodiment, the emulsifier is glycerol stearate.

Suitable classes of penetration enhancers are known in the art and include, but are not limited to, fatty alcohols, fatty acid esters, fatty acids, fatty alcohol ethers, amino acids, phospholipids, lecithins, cholate salts, enzymes, amines and amides, complexing agents (liposomes, cyclodextrins, modified celluloses, and diimides), macrocyclics, such as macrocylic lactones, ketones, and anhydrides and cyclic ureas, surfactants, N-methyl pyrrolidones and derivatives thereof, DMSO and related compounds, ionic compounds, azone and related compounds, and solvents, such as alcohols, ketones, amides, polyols (e.g., glycols). Examples of these classes are known in the art.

i. Lotions, Creams, Gels, Ointments, Emulsions, and Foams

"Hydrophilic" as used herein refers to substances that have strongly polar groups that readily interact with water.

"Lipophilic" refers to compounds having an affinity for lipids.

"Amphiphilic" refers to a molecule combining hydrophilic and lipophilic (hydrophobic) properties "Hydrophobic" as used herein refers to substances that lack an affinity for water; tending to repel and not absorb water as well as not dissolve in or mix with water.

A "gel" is a colloid in which the dispersed phase has combined with the continuous phase to produce a semisolid material, such as jelly.

An "oil" is a composition containing at least 95% wt of a lipophilic substance. Examples of lipophilic substances include but are not limited to naturally occurring and synthetic oils, fats, fatty acids, lecithins, triglycerides and combinations thereof.

A "continuous phase" refers to the liquid in which solids are suspended or droplets of another liquid are dispersed, and is sometimes called the external phase. This also refers to the fluid phase of a colloid within which solid or fluid particles are distributed. If the continuous phase is water (or another hydrophilic solvent), water-soluble or hydrophilic drugs will dissolve in the continuous phase (as opposed to being dispersed). In a multiphase formulation (e.g., an emulsion), the discreet phase is suspended or dispersed in the continuous phase.

An "emulsion" is a composition containing a mixture of non-miscible components homogenously blended together. In particular embodiments, the non-miscible components include a lipophilic component and an aqueous component. An emulsion is a preparation of one liquid distributed in small globules throughout the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

An emulsion is a preparation of one liquid distributed in small globules throughout the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. The oil phase may consist at least in part of a propellant, such as an HFA propellant. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

A sub-set of emulsions are the self-emulsifying systems. These drug delivery systems are typically capsules (hard shell or soft shell) comprised of the drug dispersed or dissolved in a mixture of surfactant(s) and lipophilic liquids such as oils or other water immiscible liquids. When the capsule is exposed to an aqueous environment and the outer gelatin shell dissolves, contact between the aqueous medium and the capsule contents instantly generates very small emulsion droplets. These typically are in the size range of micelles or nanoparticles. No mixing force is required to generate the emulsion as is typically the case in emulsion formulation processes.

A "lotion" is a low- to medium-viscosity liquid formulation. A lotion can contain finely powdered substances that are in soluble in the dispersion medium through the use of suspending agents and dispersing agents. Alternatively, lotions can have as the dispersed phase liquid substances that are immiscible with the vehicle and are usually dispersed by means of emulsifying agents or other suitable stabilizers. In one embodiment, the lotion is in the form of an emulsion having a viscosity of between 100 and 1000 centistokes. The fluidity of lotions permits rapid and uniform application over a wide surface area. Lotions are typically intended to dry on the skin leaving a thin coat of their medicinal components on the skin's surface.

A "cream" is a viscous liquid or semi-solid emulsion of either the "oil-in-water" or "water-in-oil type". Creams may contain emulsifying agents and/or other stabilizing agents. In one embodiment, the formulation is in the form of a cream having a viscosity of greater than 1000 centistokes, typically in the range of 20,000-50,000 centistokes. Creams are often time preferred over ointments, as they are generally easier to spread and easier to remove.

The difference between a cream and a lotion is the viscosity, which is dependent on the amount/use of various oils and the percentage of water used to prepare the formulations. Creams are typically thicker than lotions, may have various uses and often one uses more varied oils/butters, depending upon the desired effect upon the skin. In a cream formulation, the water-base percentage is about 60-75% and the oil-base is about 20-30% of the total, with the other percentages being the emulsifier agent, preservatives and additives for a total of 100%.

An "ointment" is a semisolid preparation containing an ointment base and optionally one or more active agents. Examples of suitable ointment bases include hydrocarbon bases (e.g., petrolatum, white petrolatum, yellow ointment, and mineral oil); absorption bases (hydrophilic petrolatum, anhydrous lanolin, lanolin, and cold cream); water-removable bases (e.g., hydrophilic ointment), and water-soluble bases (e.g., polyethylene glycol ointments). Pastes typically differ from ointments in that they contain a larger percentage of solids. Pastes are typically more absorptive and less greasy that ointments prepared with the same components.

A "gel" is a semisolid system containing dispersions of small or large molecules in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components. Suitable gelling agents include, but are not limited to, modified celluloses, such as hydroxypropyl cellulose and hydroxyethyl cellulose; Carbopol homopolymers and copolymers; and combinations thereof. Suitable solvents in the liquid vehicle include, but are not limited to, diglycol monoethyl ether; alklene glycols, such as propylene glycol; dimethyl isosorbide; alcohols, such as isopropyl alcohol and ethanol. The solvents are typically selected for their ability to dissolve the drug. Other additives, which improve the skin feel and/or emolliency of the formulation, may also be incorporated. Examples of such additives include, but are not limited, isopropyl myristate, ethyl acetate, $C_{12}$-$C_{15}$ alkyl benzoates, mineral oil, squalane, cyclomethicone, capric/caprylic triglycerides, and combinations thereof.

Foams consist of an emulsion in combination with a gaseous propellant. The gaseous propellant consists primarily of hydrofluoroalkanes (HFAs). Suitable propellants include HFAs such as 1,1,1,2-tetrafluoroethane (HFA 134a) and 1,1,1,2,3,3,3-heptafluoropropane (HFA 227), but mixtures and admixtures of these and other HFAs that are currently approved or may become approved for medical use are suitable. The propellants preferably are not hydrocarbon propellant gases, which can produce flammable or explosive vapors during spraying. Furthermore, the compositions preferably contain no volatile alcohols, which can produce flammable or explosive vapors during use.

Buffers are used to control pH of a composition. Preferably, the buffers buffer the composition from a pH of about 4 to a pH of about 7.5, more preferably from a pH of about 4 to a pH of about 7, and most preferably from a pH of about 5 to a pH of about 7. In a preferred embodiment, the buffer is triethanolamine.

Preservatives can be used to prevent the growth of fungi and microorganisms. Suitable antifungal and antimicrobial agents include, but are not limited to, benzoic acid, butylparaben, ethyl paraben, methyl paraben, propylparaben, sodium benzoate, sodium propionate, benzalkonium chloride, benzethonium chloride, benzyl alcohol, cetylpyridinium chloride, chlorobutanol, phenol, phenylethyl alcohol, and thimerosal.

In certain embodiments, it may be desirable to provide continuous delivery of one or more compounds to a patient in need thereof. For topical applications, repeated application can be done or a patch can be used to provide continuous administration of the compounds over an extended period of time.

D. Pulmonary Formulations

In one embodiment, the compounds are formulated for pulmonary delivery, such as intranasal administration or oral inhalation. The respiratory tract is the structure involved in the exchange of gases between the atmosphere and the blood stream. The lungs are branching structures ultimately ending with the alveoli where the exchange of gases occurs. The alveolar surface area is the largest in the respiratory system and is where drug absorption occurs. The alveoli are covered by a thin epithelium without cilia or a mucus blanket and secrete surfactant phospholipids. The respiratory tract encompasses the upper airways, including the oropharynx and larynx, followed by the lower airways, which include the trachea followed by bifurcations into the bronchi and bronchioli. The upper and lower airways are called the conducting airways. The terminal bronchioli then divide into respiratory bronchiole, which then lead to the ultimate respiratory zone, the alveoli, or deep lung. The deep lung, or alveoli, is the primary target of inhaled therapeutic aerosols for systemic drug delivery.

Pulmonary administration of therapeutic compositions comprised of low molecular weight drugs has been observed, for example, beta-androgenic antagonists to treat asthma. Other therapeutic agents that are active in the lungs have been administered systemically and targeted via pulmonary absorption. Nasal delivery is considered to be a promising technique for administration of therapeutics for the following reasons: the nose has a large surface area available for drug absorption due to the coverage of the epithelial surface by numerous microvilli, the subepithelial layer is highly vascularized, the venous blood from the nose passes directly into the systemic circulation and therefore avoids the loss of drug by first-pass metabolism in the liver, it offers lower doses, more rapid attainment of therapeutic blood levels, quicker onset of pharmacological activity, fewer side effects, high total blood flow per $cm^3$, porous endothelial basement membrane, and it is easily accessible.

The term aerosol as used herein refers to any preparation of a fine mist of particles, which can be in solution or a suspension, whether or not it is produced using a propellant. Aerosols can be produced using standard techniques, such as ultrasonication or high-pressure treatment.

Carriers for pulmonary formulations can be divided into those for dry powder formulations and for administration as solutions. Aerosols for the delivery of therapeutic agents to the respiratory tract are known in the art. For administration via the upper respiratory tract, the formulation can be formulated into a solution, e.g., water or isotonic saline, buffered or un-buffered, or as a suspension, for intranasal administration as drops or as a spray. Preferably, such solutions or suspensions are isotonic relative to nasal secretions and of about the same pH, ranging e.g., from about pH 4.0 to about pH 7.4 or, from pH 6.0 to pH 7.0. Buffers should be physiologically compatible and include, simply by way of example, phosphate buffers. For example, a representative nasal decongestant is described as being buffered to a pH of about 6.2. One skilled in the art can readily determine a suitable saline content and pH for an innocuous aqueous solution for nasal and/or upper respiratory administration.

Preferably, the aqueous solution is water, physiologically acceptable aqueous solutions containing salts and/or buffers, such as phosphate buffered saline (PBS), or any other aqueous solution acceptable for administration to a animal or human. Such solutions are well known to a person skilled in the art and include, but are not limited to, distilled water, de-ionized water, pure or ultrapure water, saline, phosphate-buffered saline (PBS). Other suitable aqueous vehicles include, but are not limited to, Ringer's solution and isotonic sodium chloride. Aqueous suspensions may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

In another embodiment, solvents that are low toxicity organic (i.e. nonaqueous) class 3 residual solvents, such as ethanol, acetone, ethyl acetate, tetrahydrofuran, ethyl ether, and propanol may be used for the formulations. The solvent is selected based on its ability to readily aerosolize the formulation. The solvent should not detrimentally react with the compounds. An appropriate solvent should be used that dissolves the compounds or forms a suspension of the compounds. The solvent should be sufficiently volatile to enable formation of an aerosol of the solution or suspension.

Additional solvents or aerosolizing agents, such as freons, can be added as desired to increase the volatility of the solution or suspension.

In one embodiment, compositions may contain minor amounts of polymers, surfactants, or other excipients well known to those of the art. In this context, "minor amounts" means no excipients are present that might affect or mediate uptake of the compounds in the lungs and that the excipients that are present are present in amount that do not adversely affect uptake of compounds in the lungs.

Dry lipid powders can be directly dispersed in ethanol because of their hydrophobic character. For lipids stored in organic solvents such as chloroform, the desired quantity of solution is placed in a vial, and the chloroform is evaporated under a stream of nitrogen to form a dry thin film on the surface of a glass vial. The film swells easily when reconstituted with ethanol. To fully disperse the lipid molecules in the organic solvent, the suspension is sonicated. Nonaqueous suspensions of lipids can also be prepared in absolute ethanol using a reusable PARI LC Jet+ nebulizer (PARI Respiratory Equipment, Monterey, Calif.).

Dry powder formulations ("DPFs") with large particle size have improved flowability characteristics, such as less aggregation, easier aerosolization, and potentially less phagocytosis. Dry powder aerosols for inhalation therapy are generally produced with mean diameters primarily in the range of less than 5 microns, although a preferred range is between one and ten microns in aerodynamic diameter. Large "carrier" particles (containing no drug) have been co-delivered with therapeutic aerosols to aid in achieving efficient aerosolization among other possible benefits.

Polymeric particles may be prepared using single and double emulsion solvent evaporation, spray drying, solvent extraction, solvent evaporation, phase separation, simple and complex coacervation, interfacial polymerization, and other methods well known to those of ordinary skill in the art. Particles may be made using methods for making microspheres or microcapsules known in the art. The preferred methods of manufacture are by spray drying and freeze drying, which entails using a solution containing the surfactant, spraying to form droplets of the desired size, and removing the solvent.

The particles may be fabricated with the appropriate material, surface roughness, diameter and tap density for localized delivery to selected regions of the respiratory tract such as the deep lung or upper airways. For example, higher density or larger particles may be used for upper airway delivery. Similarly, a mixture of different sized particles, provided with the same or different EGS may be administered to target different regions of the lung in one administration.

Formulations for pulmonary delivery include unilamellar phospholipid vesicles, liposomes, or lipoprotein particles. Formulations and methods of making such formulations containing nucleic acid are well known to one of ordinary skill in the art. Liposomes are formed from commercially available phospholipids supplied by a variety of vendors including Avanti Polar Lipids, Inc. (Birmingham, Ala.). In one embodiment, the liposome can include a ligand molecule specific for a receptor on the surface of the target cell to direct the liposome to the target cell.

E. Other Active Agents

The compounds described herein can be co-administered with one or more additional active agents, such as diagnostic agents, therapeutic agents, and/or prophylactic agents. Suitable classes of active agents include, but are not limited to:

Alkylating agents, such as nitrogen mustards (e.g., mechloroethamine, cyclophosphamide, ifosfamide, melphalan, and chlorambucil), ethylenimines and methylmelamines (e.g., heaxmethylmelamine), alkyl sulfonates (e.g., thiotepa and busulfan) nitrosoureas (e.g., carmustine, lomustine, semustine, and streptozocin), and triazines (e.g., dacarbazine);

Antimetabolites, such as folic acid and analogs thereof (e.g., methotrexate), pyrimidine analogs (e.g., fluoracil, floxuridine, and cytarabine), purine analogs and related inhibitors (e.g., mercaptopurine, thioguanine, and pentostatin), Cytotoxic anticancer agents, such as paclitaxel;

Cytostatic and/or cytotoxic agents such as anti-angiogenic agents such as endostatin, angiostatin, thalidomide;

Analgesics, such as opioid and non-opioid analgesics; and

Vaccines containing cancer antigens or immunomodulators such as cytokines to enhance the anti-cancer activity;

Natural products, such as vinca alkaloids (e.g., vinblastine and vincristine), epipodophyllotoxins (e.g., etoposide and tertiposide), antibiotics (e.g., dactinomycin, daunorubicin, doxorubicin, bleomycin, plicamycin, and mitomycin), enzymes (e.g., L-asparaginase), and biological response modifiers (e.g., interferon alpha);

Proteasome inhibitors, such as lactacystin, MG-132, and PS-341;

Tyrosine kinase inhibitors, such as Gleevec®, ZD 1839 (Iressa®), SH268, genistein, CEP2563, SU6668, SU1 1248, and EMD121974;

Retinoids and synthetic retinoids, such as bexarotene, tretinoin, 13-cis-retinoic acid, 9-cis-retinoic acid, .alpha.-difluoromethylornithine, ILX23-7553, fenretinide, and N-4-carboxyphenyl retinamide;

Cyclin-dependent kinase inhibitors, such as flavopiridol, UCN-01, roscovitine and olomoucine;

COX-2 inhibitors include, such as celecoxib, valecoxib, and rofecoxib;

Prenylprotein transferase inhibitors, such as R1 15777, SCH66336, L-778,123, BAL9611 and TAN-1813;

Hormones and antagonists, such as adrenocorticosteroids (e.g., prednisone), progestins (e.g, hydroxyprogesterone caproate, medroxyprogesterone acetate, and megestrol acetate), estrogens (e.g., diethylstilbestrol and ethinyl estradiol), antiestrogen (e.g., tamoxifen), androgens (e.g., testosterone propionate, fluoxtnesterone, antiandrogen), and gonadotropin-releasing hormone analogs;

Sigma-2 receptor agonists, such as CB-64D, CB-184 and haloperidol;

HMG-CoA reductase inhibitors, such as lovastatin, simvastatin, pravastatin, fluvastatin, atorvastatin and cerivastatin;

HIV protease inhibitors, such as amprenavir, abacavir, CGP-73547, CGP-61755, DMP-450, indinavir, nelfinavir, tipranavir, ritonavir, saquinavir, ABT-378, AG 1776, and BMS-232,632;

Miscellaneous compounds include platinum coordination complexes (e.g., cisplatin and carboplatin), anthracenedione (e.g., mitoxantrone), substituted urea (hydroxyurea), methyl hydrazines (e.g., procarbazine), and adrenocortical suppressants (e.g., mitotane and aminogluethimide).

The one or more compounds and the one or more additional active agents can be formulated in the same dosage form or separate dosage forms. Alternatively, the one or more additional active agents can be administered simultaneously or almost simultaneously in different dosage forms. If in separate dosage units, the one or more compounds and the one or more additional active agents can be administered by the same route of administration or by different routes of administration. For example, the one or more compounds and the one or more additional active agents can both be administered parenterally, or one can be administered parenterally and one orally.

If the one or more compounds and the one or more active agents are administered sequentially, the second agent to be administered is administered typically less than 6 hours following administration of the first agent, preferably less than 4 hours after the first agent, more preferably less than 2 hours after the first agent, more preferably less than 1 hour after the first agent, most preferably less than 30 minutes after administration of the first agent, and most preferably immediately after administration of the first agent "Immediately", as used here, means less than 10 minutes, preferably less than 5 minutes, more preferably less than 2 minutes, most preferably less than one minute.

The compounds and the one or more additional active agents can be formulated for controlled release, for example, immediate release, delayed release, extended release, pulsatile release, and combinations thereof. In one embodiment, the one or more compounds are formulated for immediate release and the one or more additional agents are formulated for delayed, extended, or pulsatile release. In another embodiment, the one or more compounds are formulated for delayed, extended, or pulsatile release and the one or more additional active agents are formulated for immediate release. In still another embodiment, the one or more compounds and the one or more additional active agents are independently formulated for delayed, extended, or pulsatile release.

IV. Methods of Making the Compounds

The compounds described herein contain a planar aromatic system as an intercalation moiety and an alkylating moiety. These compounds can be prepared by a variety of methodologies. One approach involves the direct replacement of the carboxylic acid group at position 3 of the core structure with an amino group. Another approach involves the use of commercially available rhein (1) and the attachment of amine linkers of various sizes and chemical properties to position 3 of the polycyclic aromatic system before the addition of alkylating agents. Two different sized linkers were chosen to be attached to rhein (1): a four-carbon diamine linker and a long diamine with ethylene glycol moieties for improved solubility.

The synthesis of the first series of compounds started with rhein (1). The first step involved the formation of acyl azide at position 3. The formation of the azide was done by addition of diphenylphosphoryl azide (DPPA) to (1) in anhydrous dimethylformamide (DMF). Triethyl amine (TEA) was used in the reaction as a base, and the yield of the reaction was 40%. The second step of the synthesis used Curtis rearrangement through heating at reflux in 1,4-dioxane for 2 hours and then hydrolysis with NaOH solution, giving a reaction yield of 30%. The synthesized compound 3 was used as a starting material for three analogues, each containing different alkylating agent (Scheme 1.1). The amine at position 3 of compound 3 was acylated using three agents, leading to three different compounds. Chloroacetyl chloride was used to form compound 5, bromoacetyl bromide was used to result in compound 6, and iodoacetyl chloride was used for the formation of compound 7.

Scheme 1.1. Synthetic route to compound 3.

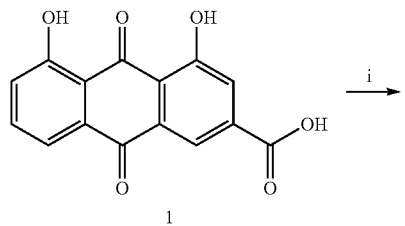

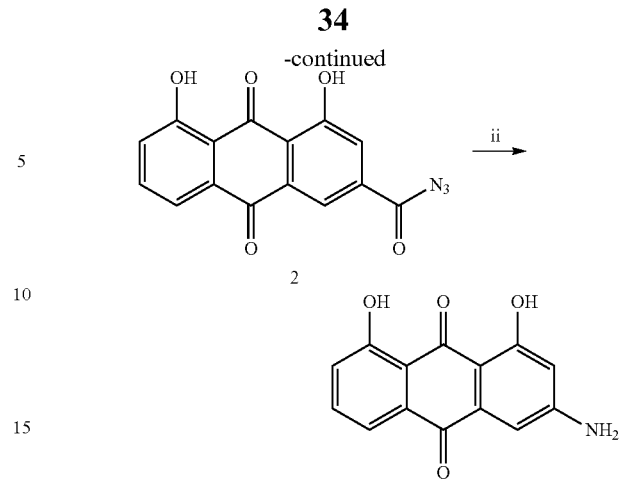

Reagents and conditions: i) DPPA, Et$_3$N, DMF, 30 min., room temperature ii) dioxane, NaOH, reflux, 4 h, 31% yield.

Analogues derived from compound 3.

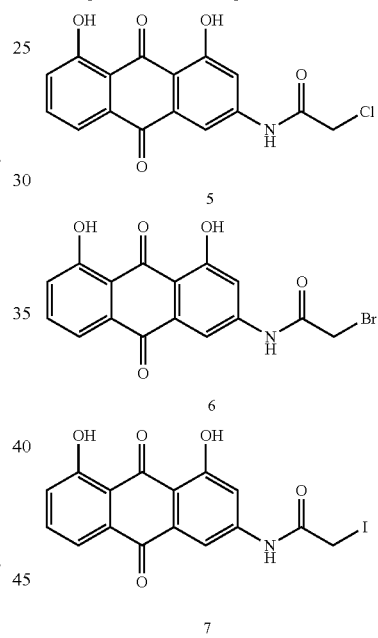

A similar approach was used to synthesize three more rhein analogues using amine (11) as a stating material (Scheme 1.2). Compound 11 was acylated using chloroacetyl chloride, bromoacetyl bromide, and iodoacetyl chloride, to give compounds 12, 13, and 14 respectively. The reaction yields were in the range between 30-40%. The low yields for these reactions are due to the extremely poor solubility of the anthraquinone compounds being synthesized. The starting material 1 itself has poor solubility in dichloromethane (DCM). Increased amount of the alkylating agent, up to two equivalents, to the free amine did not improve the reaction yields. Addition of one equivalent of TEA did not affect the reaction outcome as well. In an attempt to improve the yields the temperature of the reaction mixture was increased to 60° C.; no significant increase in yield was observed.

Scheme 1.2. Synthetic route to compound 11.

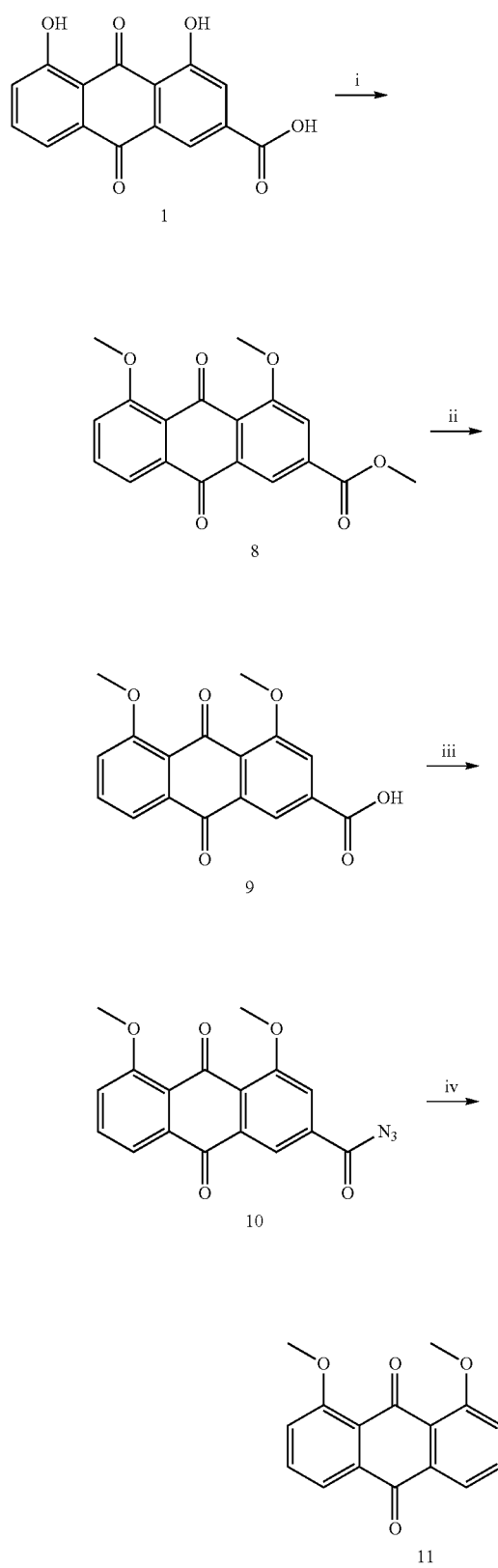

Reagents and conditions i) NaH, MeI, DMF, ii) NaOH, EtOH/H₂O, iii) DPPA, Et₃N, DMF, iv) dioxane, NaOH Analogues derived from coupound 11.

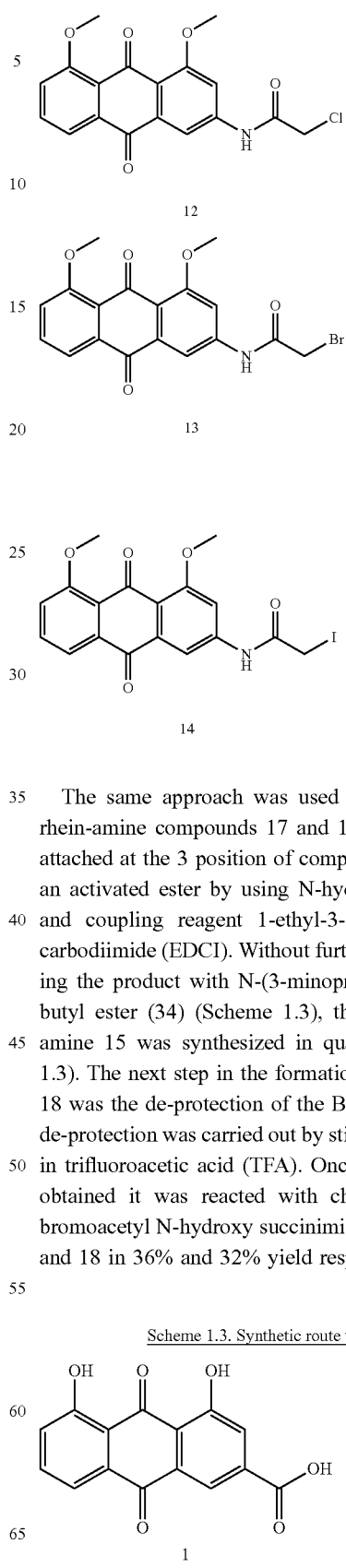

The same approach was used for the synthesis of the rhein-amine compounds 17 and 18. The carboxylic group attached at the 3 position of compound 1 was converted to an activated ester by using N-hydroxysuccinimide (NHS) and coupling reagent 1-ethyl-3-(3-dimethylaminopropyl) carbodiimide (EDCI). Without further purification, by reacting the product with N-(3-minopropyl)carbamic acid tert-butyl ester (34) (Scheme 1.3), the desired Boc-protected amine 15 was synthesized in quantitative yield (Scheme 1.3). The next step in the formation of compounds 17, and 18 was the de-protection of the Boc protecting group. The de-protection was carried out by stirring the protected amine in trifluoroacetic acid (TFA). Once the free amine 16 was obtained it was reacted with chloroacetyl chloride and bromoacetyl N-hydroxy succinimide to give compounds 17 and 18 in 36% and 32% yield respectively.

Scheme 1.3. Synthetic route to compound 16.

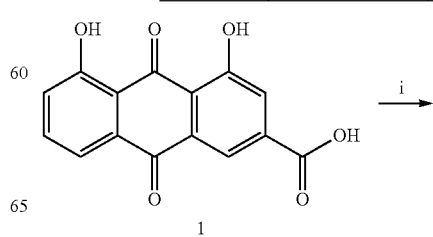

37

-continued

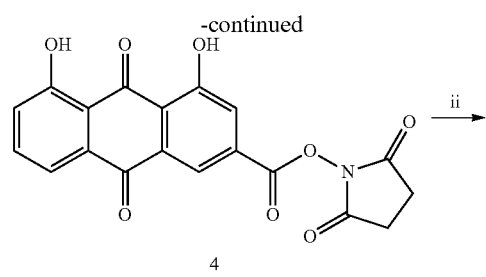

4

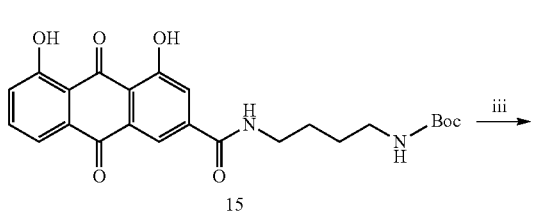

15

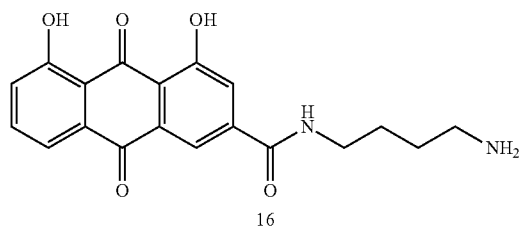

16

38

-continued

Reagents and conditions: i) NHS, EDCl, DCM, 0° C. to room temperature, overnight
ii) 34, Et₃N, DCM, room temperature, 2 h. iii) TFA, DCM, room tempeature 2 h, quantitative yield.
Analogues derviced from compound 16.

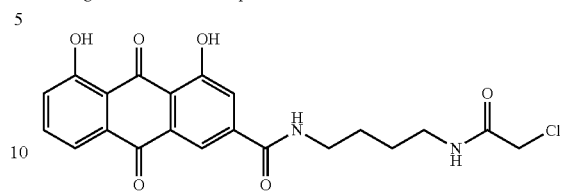

17

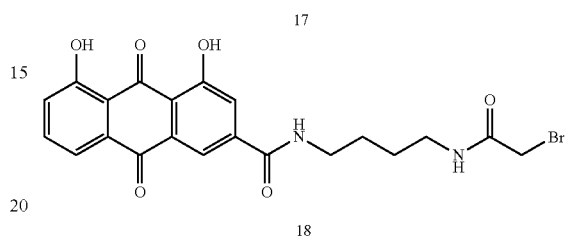

18

In an attempt to improve solubility, a long chain linker containing the ethylene glycol moiety was used in the synthesis of three more rhein analogues. N-[(tert-Butoxycarbonyl]-4,7,10-trioxa-1,13-tridecanediamine (35) was directly added to the activated ester 4 generated in situ from 1 using EDCI and NHS to give the Boc-protected amine 19 in 98% yield (Scheme 1.4). This was followed by the de-protection of the Boc-group in TFA, giving the free amine 20 in quantitative yield. Amine 20 was reacted with chloroacetyl chloride, bromoacetyl N-hydroxy succinimide, and iodoacetyl chloride to give analogues 21, 22, and 23 respectively. Despite the addition of linker 35 containing the ethylene glycol moiety, the solubility of the synthesized compounds did not improve and the yields ranged from 30% to 39%. All of the eleven compounds were examined for their in vitro cytotoxicity using the MTT (3-(4,5-dimethylthiazol-2-yl)-2,5-diphenyltetrazolium bromide) assay.

Scheme 1.4. Synthetic route to compound 20.

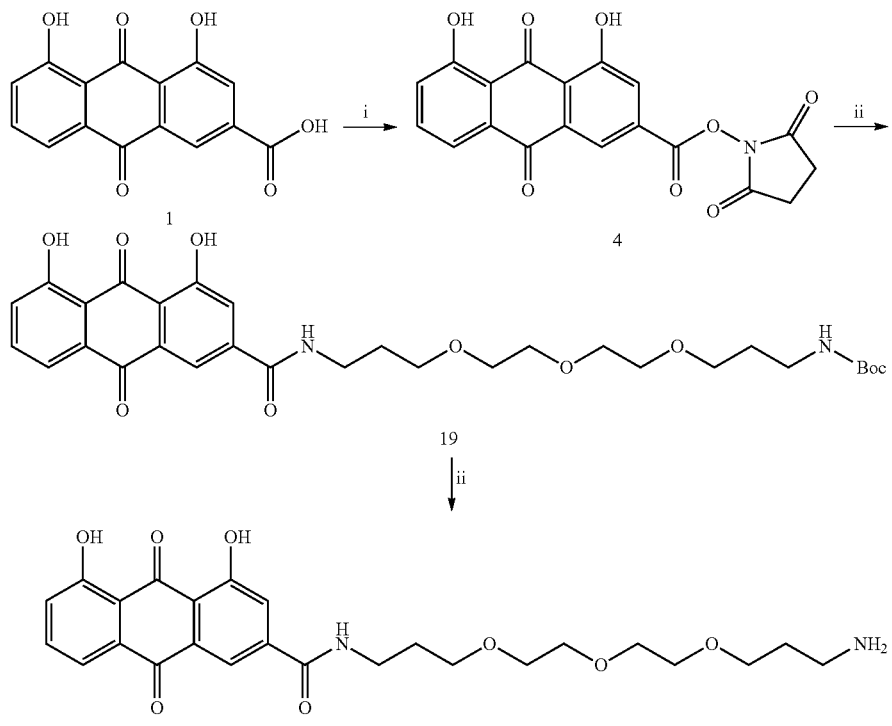

-continued
Reagents and conditions i)NHS, EDCl, DCM, 0° C. to room temperature, overnight ii) 35, Et₃N, DCM, room temperature, 2 h. iii) TFA, DCM, room temperature 2 h., quantitative yield
Analogues derived from compound 20.
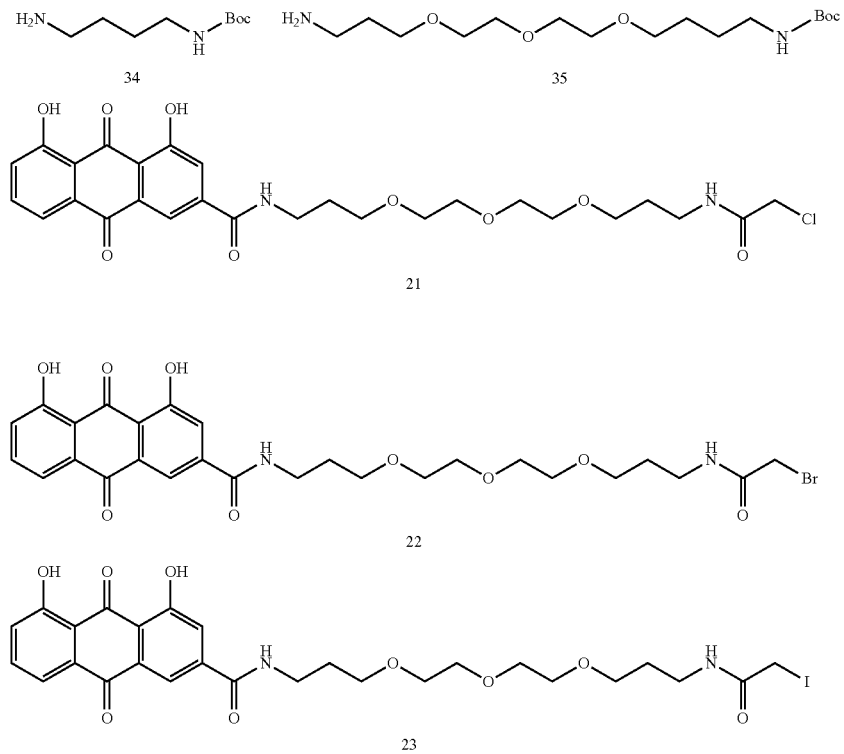
Synthesis of diethoxy derivatives is shown below in Scheme 1.5.
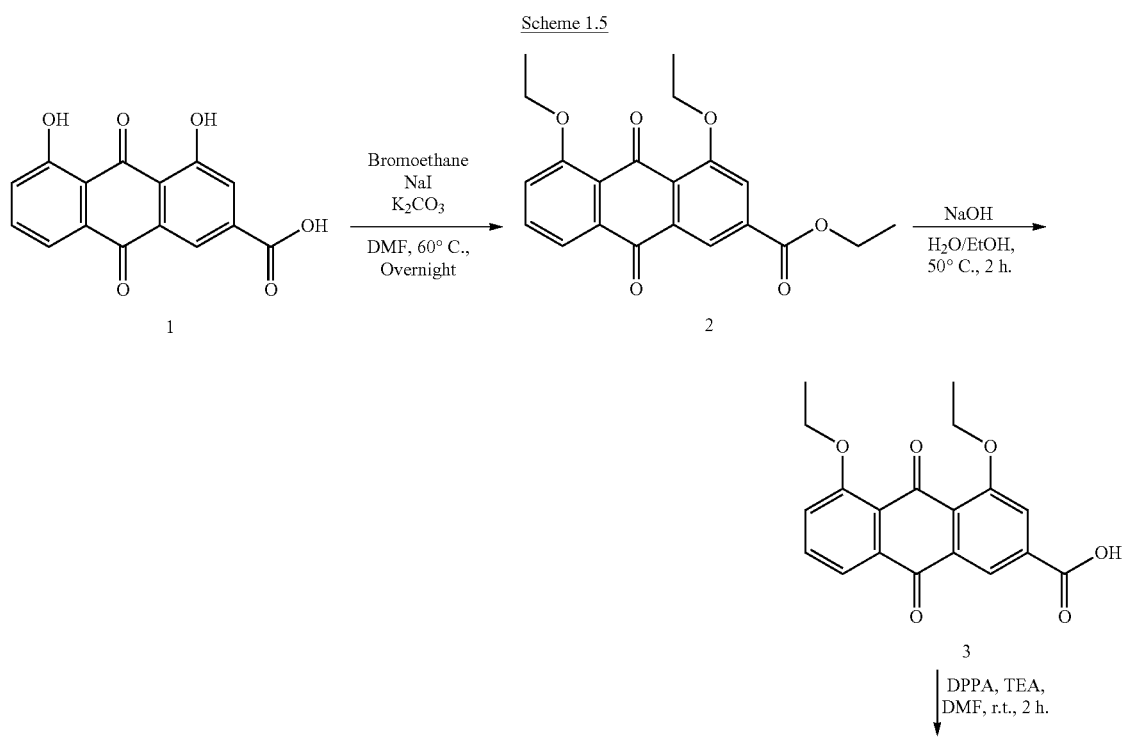

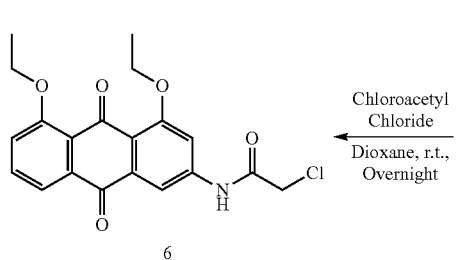
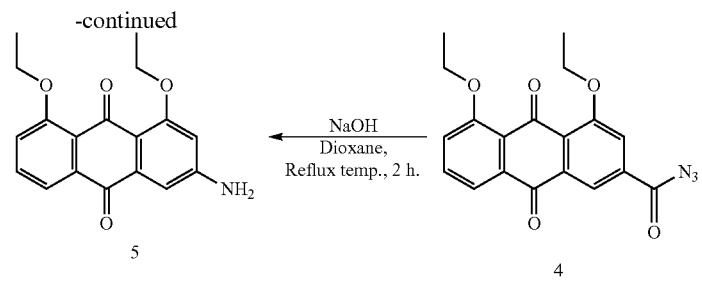

In order to improve the solubility of the flat anthraquinone rhein analogues, longer side chains at positions 1 and 8 of the core rhein structure were incorporated. The placement of long alkyl chains at these positions should disrupt the pi-pi stacking of the flat polycyclic aromatic systems and improve solubility. This was in fact observed with the diethyl compounds shown above.

The compounds described herein can be grouped into eight major groups based on the modifications made at the 1 and 8 positions of the core anthraquinone structure (e.g., compounds containing methyl, ethyl, propyl, benzyl, allyl, azido-alkyl, isopropyl, and isobutyl functional groups protecting the 1 and 8-hydroxyl positions (FIGS. 10-16). The synthetic strategy used to prepare the compounds shown in FIGS. 1-5 involved four steps. Seven of the synthetic routes described herein (Schemes 2-6, 8, and 9) utilize a similar strategy with slight variations.

The aniline compounds in schemes 2-6, 8, and 9 (compounds 5, 9, 13, 17, 21, 26, 30, and 34) prepared from the four step methodology were used as building blocks to prepare a variety of compounds tested against a variety of cancer cell lines. The first step of each of these five routes involves protection through alkylation of the 1- and 8-hydroxyl groups and formation of an ester at position 3 through reaction with methyl iodide, 1-bromoethane, 1-bromopropane, benzyl chloride, allyl bromide, 1-bromo-2-methyl propane, and 1-bromo-3-methyl butane to give compounds 2, 6, 10, 14, 18, 27, and 31 (See Schemes 2-9).

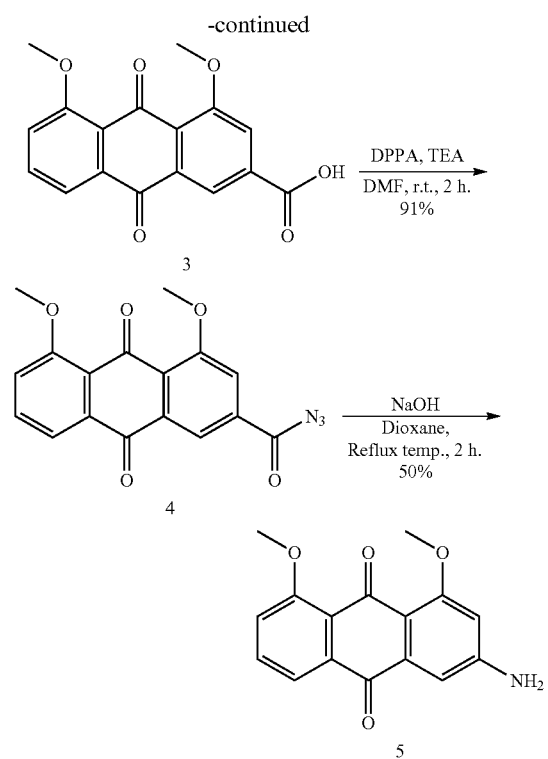

Scheme 2. Synthetic route to compound 5

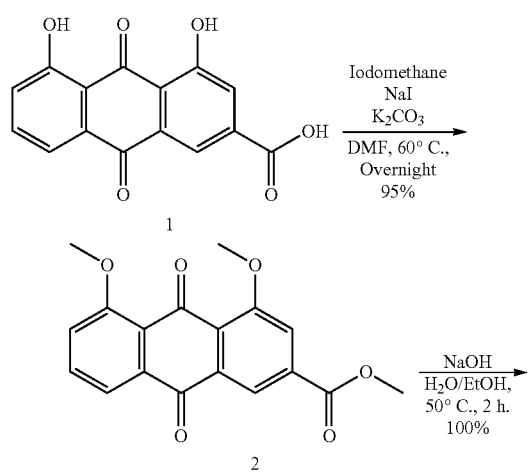

Scheme 3. Synthethic route to compound 9

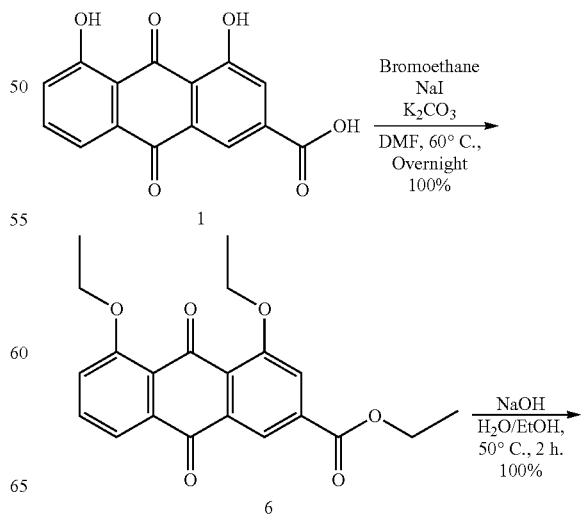

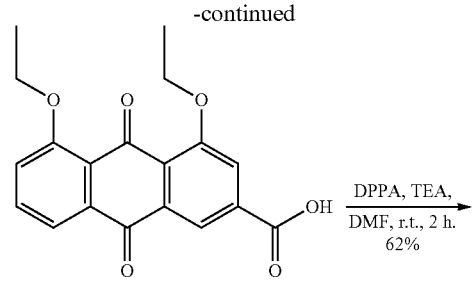

Scheme 6. Synthetic route to compound 21
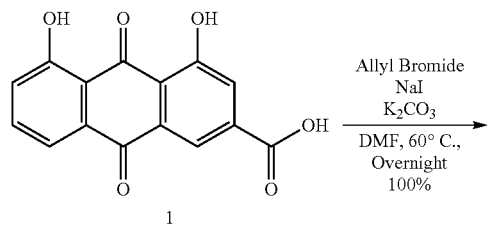
1
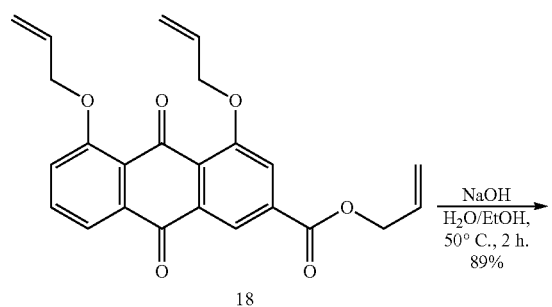
18
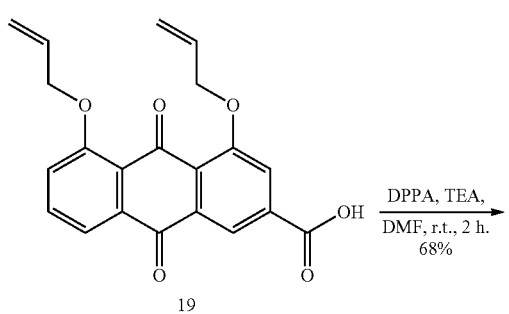
19
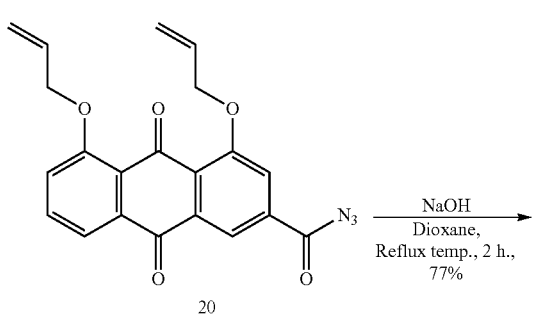
20
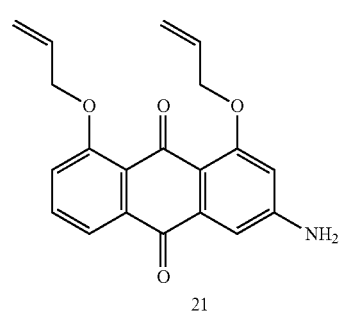
21
Scheme 7. Synthetic route to compound 26
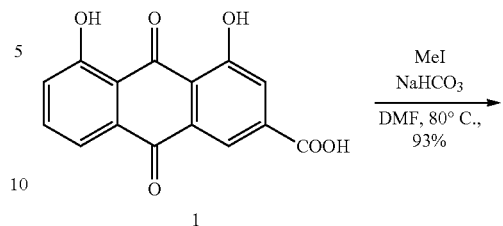
1
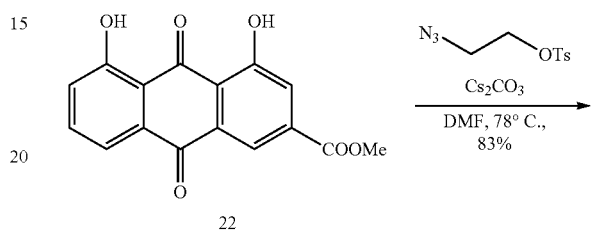
22
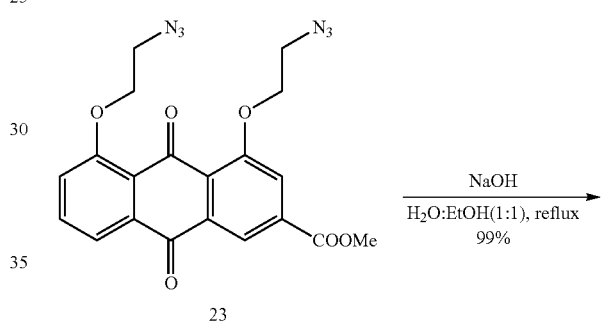
23
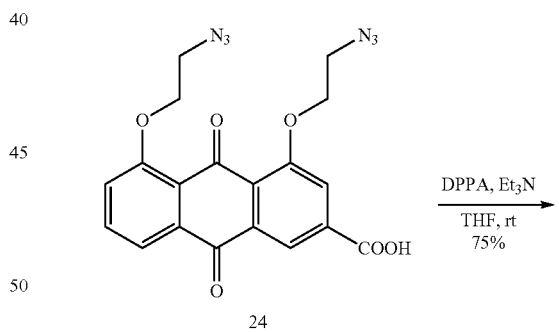
24
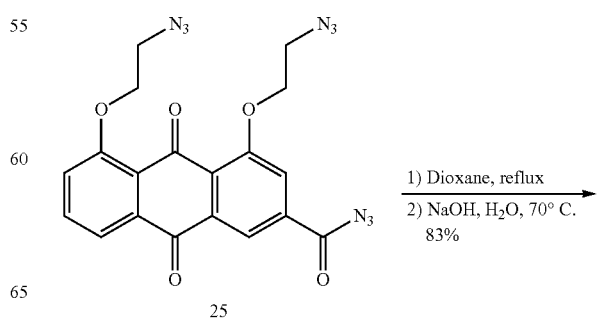
25

47
-continued
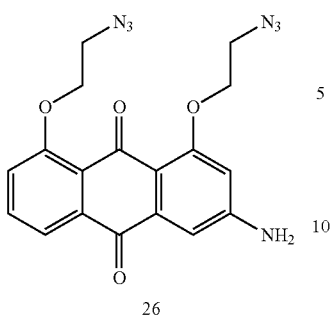
26
Scheme 8. Synthetic route to compound 30
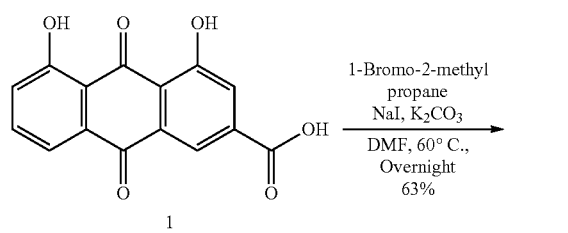
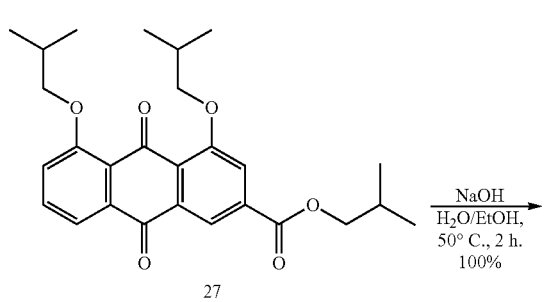
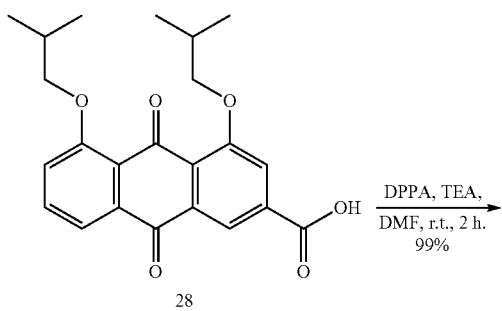
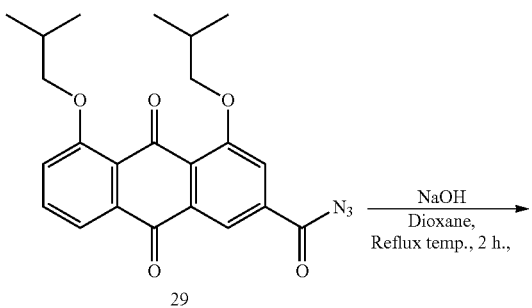
48
-continued
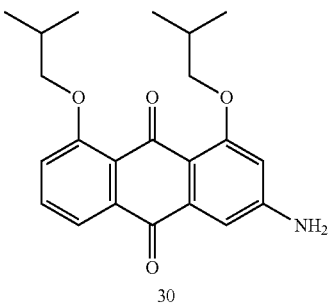
30
Scheme 9. Synthetic route to compound 34
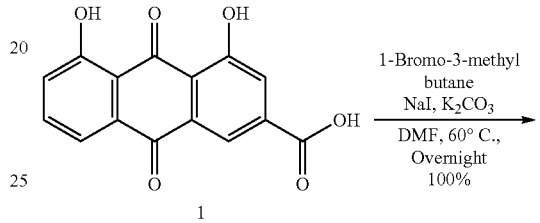
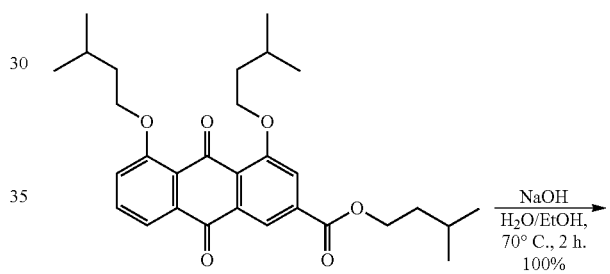
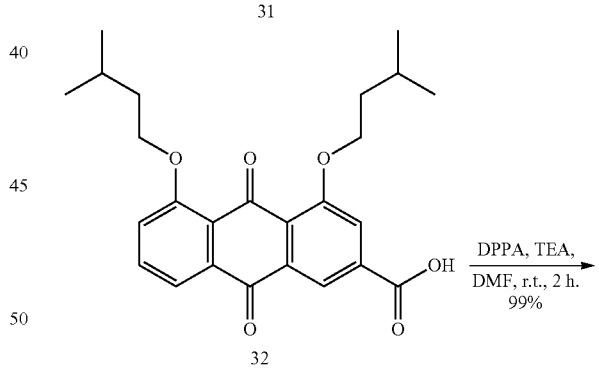
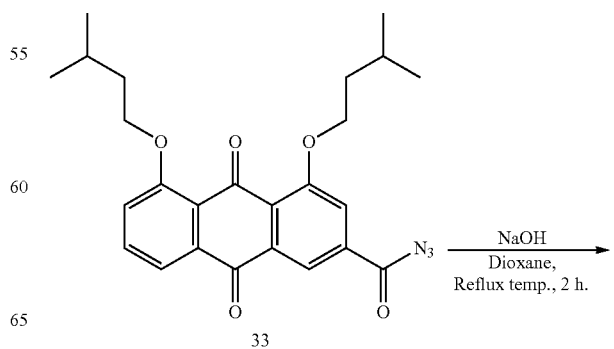

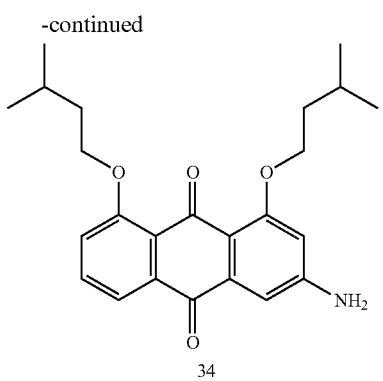
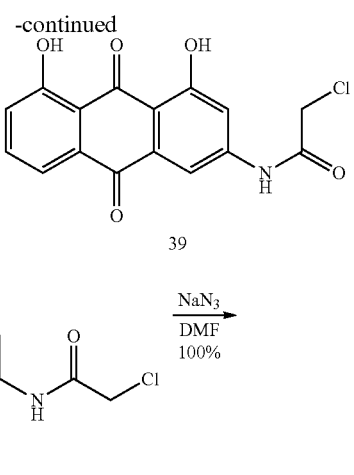
The preparation of a variety of derivatives/analogs from amines 5, 9, 13, 17, 21, 26, 30, or 34 is shown in Scheme 10.
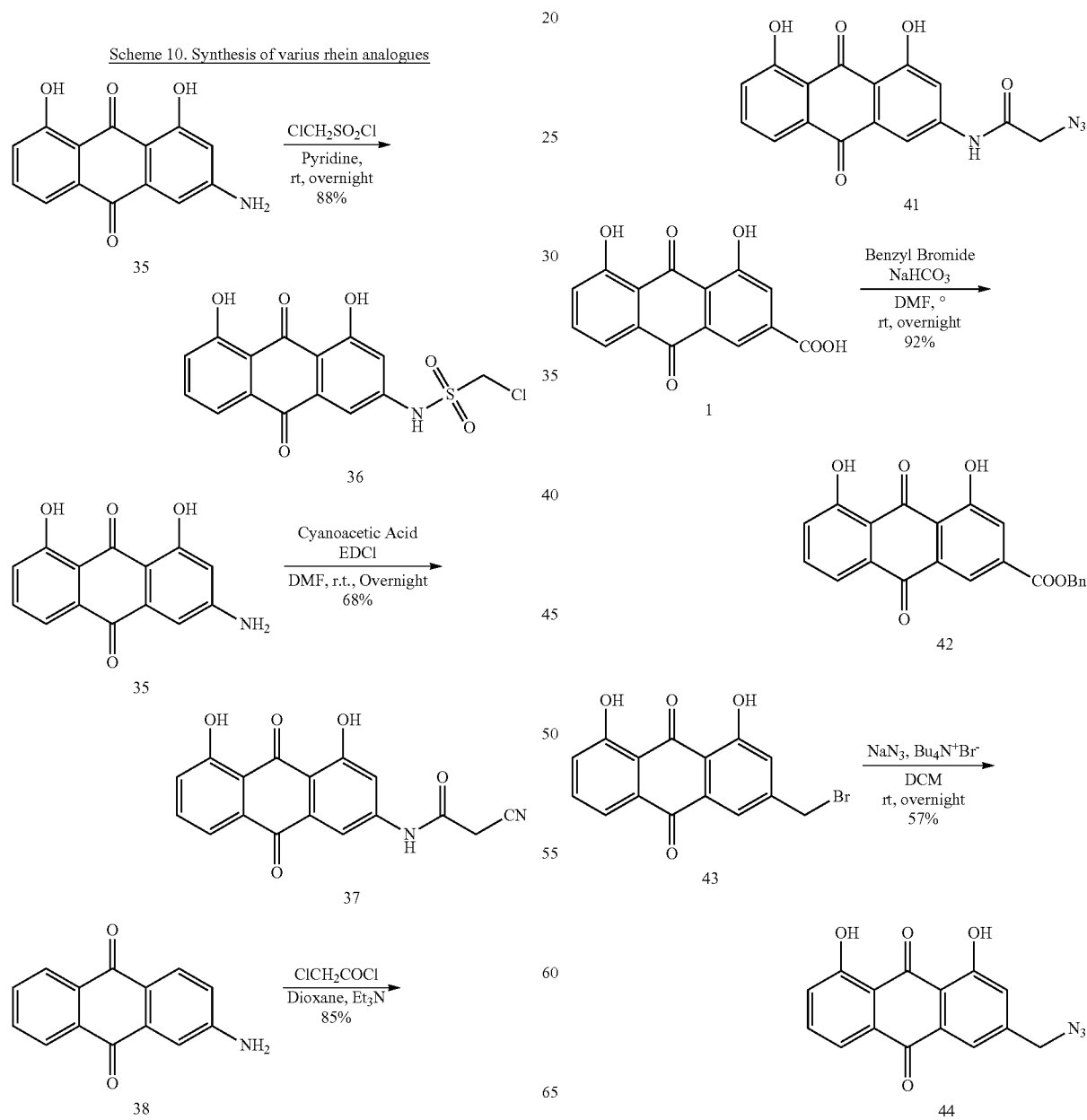

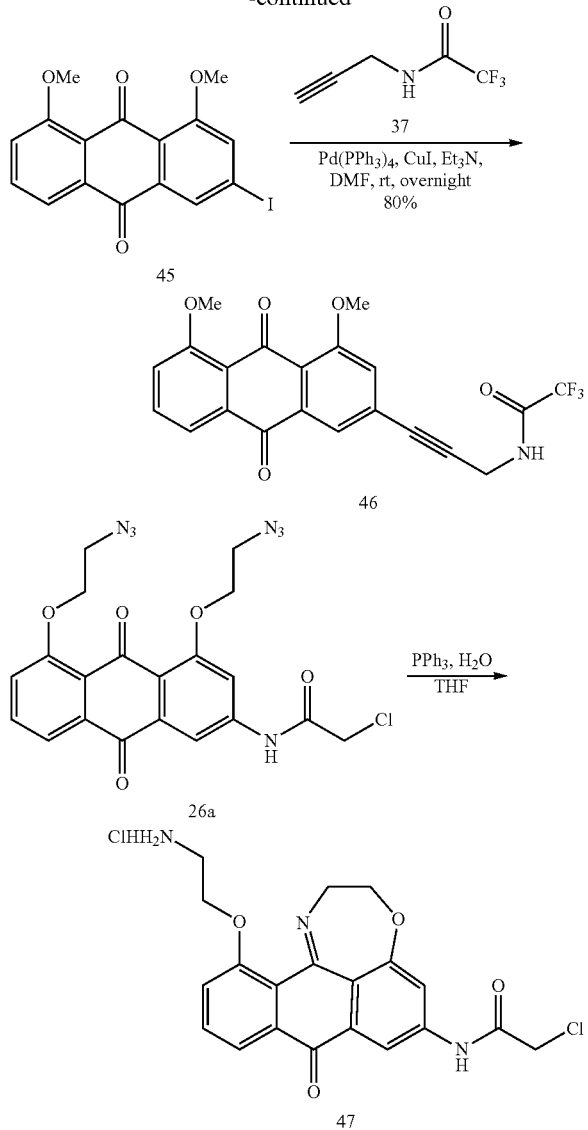

V. Methods of Using the Compounds

The compounds described herein can be administered to a subject in need thereof to treat the subject either prophylactically (i.e., to prevent cancer) or therapeutically (i.e., to treat cancer after it has been detected), including reducing tumor growth, reducing the risk of local invasiveness of a tumor, increasing survival time of the patient, and/or reducing the risk of metastasis of a primary tumor.

The compounds described herein can contact a target cell to inhibit the initiation and promotion of cancer, to kill cancer/malignant cells, to inhibit cell growth, to induce apoptosis, to inhibit metastasis, to decrease tumor size, to otherwise reverse or reduce the malignant phenotype of tumor cells, and combinations thereof. This may be achieved by contacting a tumor or tumor cell with a single composition or pharmacological formulation that includes the compound(s), or by contacting a tumor or tumor cell with more than one distinct composition or formulation, simultaneously, wherein one composition includes one or more compounds described herein and the other includes a second agent.

Exemplary cancers, which can be treated, include, but are not limited to, cancer of the skin, colon, uterine, ovarian, pancreatic, lung, bladder, breast, renal system, and prostate. Other cancers include, but are not limited to, cancers of the brain, liver, stomach, esophagus, head and neck, testicles, cervix, lymphatic system, larynx, esophagus, parotid, biliary tract, rectum, endometrium, kidney, and thyroid; including squamous cell carcinomas, adenocarcinomas, small cell carcinomas, gliomas, neuroblastomas, and the like. Assay methods for ascertaining the relative efficacy of the compounds described herein in treating the above types of cancers as well as other cancers are well known in the art.

The compounds described herein can also be used to treat metastatic cancer either in patients who have received prior chemo, radio, or biological therapy or in previously untreated patients. In one embodiment, the patient has received previous chemotherapy. Patients can be treated using a variety of routes of administration including systemic administration, such as intravenous administration or subcutaneous administration, oral administration or by intratumoral injection.

The compounds described herein can also be used to treat patients who have been rendered free of clinical disease by surgery, chemotherapy, and/or radiotherapy. In these aspects, the purpose of therapy is to prevent or reduce the likelihood of recurrent disease. Adjuvant therapy can be administered in the same regimen as described above to prevent recurrent disease.

Rhein analogues were synthesized by linking an alkylating agent to position 3 of the core structure. The synthesized analogues were tested in vitro by using the MTT assay against three different cell lines: HeLa, Hek, and KB. All of the compounds tested showed improved cytotoxicity compared to rhein with $IC_{50}$ values in the μM range against cancer cells. Four of the compounds 5, 12, 14, and 18, showed significant improvement against HeLa cells. The improvement of cytotoxycity at such level is evidence that the combination of an intercalating moiety and an alkylating agent can be a successful strategy for designing DNA targeting anticancer drugs. In some embodiments, the compounds exhibit an $IC_{50}$ against a particular cell line or lines of less than 100, 95, 90, 85, 80, 75, 70, 65, 60, 55, 50, 45, 40, 35, 30, 25, 20, 15, 10, 5, 4, 3, 2, or 1 micromolar. In other embodiments, the compounds exhibit an $IC_{50}$ against a particular cell line or lines which is similar to that of doxorubicin but wherein the compounds exhibit less toxicity than doxorubicin. In still other embodiments, the compounds exhibit an $IC_{50}$ less than about 100 micromolar and exhibit reduced toxicity compared to doxorubicin.

It was observed that the compounds described herein efficiently induced cell death in wt-p53, but not in p53-deficient cancer cells and normal cells. Furthermore, the cytotoxic and apoptotic effects of the compounds described herein are closely associated with the concomitant expression of MDM2 and MDM4.

MDM2 is a negative regulator of the p53 tumor suppressor. MDM2 protein functions as an E3 ubiquitin ligase that recognizes the N-terminal trans-activation domain (TAD) of the p53 tumor suppressor and as an inhibitor of p53 transcriptional activation. Several human tumor types have been shown to have increased levels of MDM2, including soft tissue sarcomas and osteosarcomas as well as breast tumors. MDM4 (also called MDMX) is also a negative regulator of p53.

The data suggests that a different pathway for activating p53 is the major mechanism by which the compounds described herein exhibit pro-apoptotic activity, and that it differs from the mechanism of doxorubicin.

Doxorubicin interacts with DNA by intercalation, inhibiting the progression of the enzyme topoisomerase II (topo II), which relaxes supercoils in DNA for transcription. Doxorubicin stabilizes the topo II complex after it has broken the DNA chain for replication, preventing the DNA double helix from being resealed and thereby stopping the process of replication, leading to DNA damage and activation of p53. Unfortunately, the DNA intercalating drug doxorubicin does distinguish between the cancer cells and normal cells, and it causes DNA damage and p53 activation in both.

The compounds described herein do not appear to intercalate to DNA. However, the compounds do specifically bind to the C-terminal RING domain of either MDM2 or MDM4 and block their interaction resulting in activation of p53. In contrast, Rhein-8 activates p53 relying on the expression of MDM2 and its heterodimer with MDM4, which is critical for inhibition of p53 in cancer cells but not in normal cells. Thus, unlike doxorubicin, the compounds described herein only induce activation of p53 in cancer cells but not in normal cells.

When studied in a panel of cancer cell lines: 6 ALL and 2 neuroblastoma (NB) that have wt-p53 phenotype and different overexpression of MDM2 and MDM4, one or more of the compounds describe herein showed potent cytotoxic effect at a lower concentration (1-2 μM) on ALL lines but not on NB lines. All 6 wt-p53 ALL lines studied concomitantly express high levels of both MDM2 and MDM4 as compared with normal bone marrow mononuclear (NBMM) cells, while 2 wt-p53 NB lines express high levels of either MDM2 or MDM4. In addition, one or more of the compounds described herein had almost no cytotoxic effect on ALL lines with a null- and mutant-p53 phenotype and no MDM2/MDM4 expression. These observations suggest that, unlike doxorubicin, the compounds described herein selectively kill cancer cells that have wt-p53 and a concomitant overexpression of MDM2 and MDM4.

Doxorubicin induces cancer cell death through the p53-dependent apoptosis pathway. The compounds described herein were evaluated to determine if they induced ALL cell death via a similar mechanism as doxorubicin. The effect of the compounds described herein on the activation of p53 and its known targets p21 and PUMA that induce cell-cycle arrest and apoptosis was investigated. By Western blot assays, it was found that one or more of the compounds induced activation of p53, p21 and PUMA in dose- and time-dependent manners. The compounds described herein induced dose- and time-dependent activation of caspase-3 and cleavage of PARP. Corresponding with the observed accumulation of p53 and induction of p21 and PUMA, there was a G1 cell-cycle arrest and apoptosis as detected by PI and annexin V staining and flow cytometry in ALL cells treated with one or more of the compounds described herein. These results suggest that the compounds described herein, like doxorubicin, induce ALL cell death via the p53-dependent apoptosis pathway.

The cytotoxic and inhibitory effects of the compounds described herein on normal human BM cells in vitro, as compared with doxorubicin was evaluated. The WST cytotoxic assay results showed that while 40-50% of human NBMM cells survived after treatment with doxorubicin at concentration of 1-2 μM, over 90% of these cells survived after treatment with same concentration of one or more of the compounds described herein. Significantly, the compounds described herein showed almost no or much less ($p<0.1$) of an inhibitory effect on CFU-GM and BFU-E of normal human BM in vitro, as compared with doxorubicin given at the same concentration.

Toxicity was also evaluated in mice. 15 mg Doxorubicin administered in a single injection at a dose of 15/kg resulted in the death of all mice at day 7 due to cardiac toxicity. In contrast, mice administered MG1 at a dose of 100 mg/kg/day, three times a day, were alive after 9 days. Subsequently, a single injection of MG1 at a dose of 400 mg/kg was administered via injection. None of the mice died after this injection.

The compositions described herein contain an effective amount of the one or more of the compounds described herein. The amount to be administered can be readily determined by the attending physician based on a variety of factors including, but not limited to, age of the patient, weight of the patient, disease or disorder to be treated, presence of a pre-existing condition, and dosage form to be administered (e.g., immediate release versus modified release dosage form). Typically, the effective amount is from about 0.1 mg/kg/day to about 200 mg/kg/day, more preferably from 0.1 mg/kg/day to 50 mg/kg/day, more preferably from 0.1 mg/kg/day to 25 mg/kg/day, and most preferably from 0.1 mg/kg/day to 10 mg/kg/day. Dosages greater or less than this may be administered depending on the diseases or disorder to be treated.

EXAMPLES

Rhein (1) was purchased from Nanjing ZeLang Medical Technology Co. LTD, China, and directly used without further purification. Other starting materials and solvents were purchased from Aldrich and Acros. Some starting materials such as 11 and the Boc-protected amine of compounds 15, and 35 were prepared in house. $^1$H spectra were obtained on a Bruker 400 NMR spectrometer in a deuterated solvent with TMS (δ=0.00 ppm). For all reactions, analytical grade solvents were used. Anhydrous solvents were used for all moisture-sensitive reactions.

Example 1. Synthesis of 1,8-dihydroxy Rhein Analogs

Synthesis of 1,8-Dihydroxy-3-amino-anthraquinone (3)

Compound 1 (500 mg, 1.7 mmol) was suspended in anhydrous dimethyl formamide (DMF, 6 mL) in a dry round bottom flask and cooled to 0° C. Triethyl acetic acid (TEA) (490 μL, 3.5 mmol) was added at 0° C. Diphenylphosphoryl azide (DPPA, 400 μL, 1.8 mmol) was added drop wise after 1 was completely dissolved. The reaction mixture was stirred at room temperature for 20 minutes. TLC (hexanes: ethyl acetate=3:1) showed complete consumption of the starting material. The solvent was evaporated in vacuo and the obtained oil was purified by silica gel column chromatography using a mixture of hexanes and ethyl acetate in a 2:1 ratio as the eluent. 200 mg of a brown-yellow powder was obtained.

Compound 2 was dissolved in 1,4-dioxane (4 mL) and stirred under reflux for 2 hours. After the color of the solution turned from brown to bright red, TLC (hexanes: ethyl acetate=2:1) showed product formation. The 1,2-dioxane volume was reduced by half using a rotavapor. 2N NaOH (4 mL) was added to the solution and a fine precipitate formed. The suspension was stirred under reflux for 2 additional hours. The solution was cooled and neutralized by addition of 1N HCl. The precipitate was too fine to be filtered so it was extracted by using dichloromethane (DCM, 3×10 mL) and washed with water (2×5 mL) and brine (1×5 mL). The organic layer was dried over $MgSO_4$, filtered and concentrated in vacuo. The obtained residue is bright red powder that was purified using silica gel column chromatography, with mixture of eluent hexanes and ethyl acetate in 10:1 ratio (50 mg, 31% yield). $^1H$ NMR (acetone-$d_6$): δ 12.04 (s, 1H), 12.27 (s, 1H), 7.67 (d, 1H, J=1.2 Hz), 7.56-7.50 (m, 2H), 7.27-7.23 (m, 1H), 7.14-(d, 1H, J=2.0 Hz), 6.37 (d, 1H, J=2.0 Hz); MS: m/z [M–H]$^-$ calculated $C_{14}H_9NO_4$ 254.01, found 254.04.

1,8-Dihydroxy-3-(2'-chloro-acetamido)-anthraquinone (5)

Chloroacetyl chloride (23 µL, 0.3 mmol) was injected slowly into the solution of (3) (50 mg, 0.2 mmol) in anhydrous 1,4-dioxane (5 mL). The mixture was stirred at room temperature for 2 h. The reaction mixture was followed by TLC (DCM:MeOH=10:1) and diluted by $H_2O$ (20 mL) and the suspension was extracted with $CH_2Cl_2$ (2×50 mL). The organic layers were combined, dried over $MgSO_4$, filtered and concentrated in vacuo. The residue was purified with silica gel column chromatography eluting with DCM:MeOH (60:1) to give an orange colored solid product (20 mg, 30% yield). $^1H$ NMR (DMSO-$d_6$): δ 12.02 (s, 1H), 11.06 (s, 1H), 7.87 (s, 1H), 7.809-7.79 (m, 2H), 7.74-7.72 (m, 1H), 7.33-7.31 (m, 1H), 4.36 (d, 2H, J=1.2 Hz); MS: m/z [M–H]$^-$ calculated $C_{16}H_{10}ClNO_5$ 330.00, found 330.10.

1,8-Dihydroxy-3-(2'-bromo-acetamido)-anthraquinone (6)

Bromoacetyl bromide (26 µL, 0.3 mmol) was injected slowly into the solution of (3) (50 mg, 0.2 mmol) in anhydrous 1,4-dioxane (5 mL). The mixture was stirred at room temperature for 2 h. The reaction mixture was followed by TLC (DCM:MeOH=10:1) and diluted by $H_2O$ (20 mL) and the suspension was extracted with $CH_2Cl_2$ (2×50 mL). The organic layers were combined, dried over $MgSO_4$, filtered and concentrated in vacuo. The residue was purified with silica gel column chromatography. The product was eluted with DCM:ethyl acetate (20:1). Orange color solid was obtained as product (18 mg, 30% yield). $^1H$ NMR (DMSO-$d_6$): δ 12.05 (s, 1H), 10.18 (s, 1H), 7.88 (d, 1H, J=2.0 Hz), 7.82-7.80 (m, 2H), 7.78-7.76 (m, 1H), 7.35 (d, 1H, J=8.4 Hz), 4.14 (s, 2H); MS: m/z [M–H]$^-$ calculated $C_{16}H_{10}BrNO_5$ 392.9, found 392.1.

1,8-Dihydroxy-3-(2'-iodo-acetamido)-anthraquinone (7)

Iodoacetyl chloride (27 µL, 0.3 mmol) was injected slowly into the solution of (3) (50 mg, 0.2 mmol) in anhydrous 1,4-dioxane (5 mL). The mixture was stirred at room temperature for 2 h. The reaction was followed by TLC (DCM:MeOH=10:1), and after completion was diluted by $H_2O$ (20 mL) and the suspension was extracted with $CH_2Cl_2$ (2×50 mL). The organic layers were combined, dried over $MgSO_4$, filtered and concentrated in vacuo. The residue was purified with silica gel column chromatography. The compound was eluted with DCM:MeOH (1:0, 60:1). Orange color solid was obtained as product (24 mg, 33% yield). $^1H$ NMR (DMSO-$d_6$): δ 11.96 (s, 1H), 11.85 (s, 1H), 7.80 (d, 1H, J=2.1 Hz), 7.75 (d, 1H, J=2.0 Hz), 7.60-7.58 (m, 2H), 7.38 (d, 1H, J=8.4 Hz), 3.87 (s, 2H); MS: m/z [M–H]$^+$ calculated $C_{16}H_{10}INO_5$ 422.9, found 422.1.

1,8-Dihydroxy-3-(2'-amido-7'-amino)-anthraquinone (16)

The Boc-protected amine of (15) (200 mg, 0.4 mmol) was suspended in DCM (5 mL). Trifluoroacetic acid was added (5 mL) and the solution was stirred at room temperature and followed by TLC (DCM:MeOH=10:1), until full de-protection was achieved. The organic layer was concentrated in vacuo. The residue was purified with silica gel column chromatography. The residue was eluted with DCM:MeOH (10:1, 8:1, 1:1). Orange color solid was obtained as product (142 mg, quantitative yield). $^1H$ NMR (DMSO-$d_6$): δ 8.96 (t, 1H, J=5.6 Hz), 8.14 (d, 1H, J=1.6 Hz), 7.81-7.74 (m, 1H), 7.73-7.71 (m, 2H), 7.40-7.38 (m, 1H), 3.38 (d, 2H, J=5.6 Hz), 2.80 (s, 2H), 2.45 (s, 2), 1.57 (s, 4H);

1,8-Dihydroxy-3-(9'-chloro-aceta-2',7'diamido)-anthraquinone (17)

Chloroacetyl chloride (24 µL, 0.21 mmol) was injected slowly into the solution of 16 (50 mg, 0.14 mmol) in anhydrous 1,4-dioxane (5 mL). The mixture was stirred at room temperature for 2 h. The reaction was followed by TLC (DCM:MeOH=10:1), and after completion was diluted by $H_2O$ (20 mL) and the suspension was extracted with $CH_2Cl_2$ (2×50 mL). The organic layers were combined, dried over $MgSO_4$, filtered and concentrated in vacuo. The residue was purified with silica gel column chromatography. The residue was eluted with DCM:methanol (60:1). Orange color solid was obtained as product (22 mg, 36% yield). $^1H$ NMR (DMSO-$d_6$): δ 11.92 (s, 2H), 8.23 (s, 1H), 7.86-7.84 9 (m, 1H), 7.77 (d, 2H, J=8.4 Hz), 7.43 (d, 1H, J=8.4 Hz), 4.03 (s, 2H), 3.24-3.20 (m, 2H), 3.25-3.18 (m, 1H), 1.54-1.50 (m, 2H), 1.49-1.45 (m, 2H); MS: m/z [M+H]$^+$ calculated $C_{21}H_{19}ClN_2O_6$ 431.1, found 431.2.

1,8-Dihydroxy-3-(9'-bromo-aceta-2',7'diamido)-anthraquinone (18)

A solution of bromoacetyl N-hydroxy succinimide (39.4 mg, 0.17 mmol) in 1 mL of anhydrous 1,4-dioxane was injected slowly into the solution of 16 (50 mg, 0.14 mmol) in anhydrous dioxane (5 mL). The mixture was stirred at room temperature for 2 hours. The reaction was followed by TLC (DCM:MeOH=10:1), and after completion was diluted by $H_2O$ (20 mL) and the suspension was extracted with $CH_2Cl_2$ (2×50 mL). The organic layers were combined, dried over $MgSO_4$, filtered and concentrated in vacuo. The residue was purified with silica gel column chromatography. The compound was eluted with DCM:methanol (60:1). Orange color solid was obtained as product (21 mg, 32% yield). $^1H$ NMR (DMSO-$d_6$): δ 11.9 (s, 2H), 8.91 (t, 1H, J=5.6 Hz), 8.24 (t, 1H, J=5.6 Hz), 8.16 (d, 1H, J=1.6 Hz), 7.84-7.80 (m, 1H), 7.76-7.63 (m, 2H), 7.41-7.35 (m, 1H), 4.0 (s, 1H), 3.15-3.10 (m, 2H), 2.52 (m, 2H), 1.51-1.43 (m, 4H); MS [M+H]$^+$ calculated $C_{21}H_{19}BrN_2O_6$ 475.04, found 475.1.

1,8-Dihydroxy-3-(6',9',12'-trioxa-2',16'-tridecanediamino)-anthraquinone (20)

Rhein (1) (500 mg, 1.8 mmol) was dissolved in dry DCM and cooled to 0° C. NHS (202 mg, 1.9 mmol) was added and the reaction mixture was stirred for 5 minutes followed by addition of EDCI (278 mg, 1.8 mmol). The reaction was monitored by TLC (DCM:MeOH=8:1) and stirred for 4 hours. To the reaction mixture, 35 (624 mg, 1.9 mmol) was added followed by TEA (183 μL, 1.3 mmol) and the mixture was stirred overnight at room temperature. After TLC showed consumption of the starting material, the organic solvent was concentrated in vacuo. The residue was purified using silica gel column chromatography with an eluent consisting of mixture between DCM:MeOH=10:1. 940 mg brown oil was obtained. The Boc-protected amine 19 (500 mg, 0.9 mmol) was suspended in DCM (7 mL). TFA (7 mL) was added and the solution was stirred at room temperature overnight. The reaction was followed by TLC (DCM:MeOH=8:1). The organic layer was concentrated in vacuo. The residue was purified with silica gel column chromatography. The residue was eluted with DCM:MeOH (10:1, 8:1, 1:1). Orange color solid was obtained as product (438 mg, quantitative yield). $^1$H NMR (DMSO-$d_6$): δ 7.9 (s, 1H), 7.66-7.60 (m, 2H), 7.54 (s, 1H), 7.28 (d, 1H, J=8.0 Hz), 3.61-3.52 (m, 13H), 3.43 (t, 2H, J=6.4 Hz), 3.22 (s, 2H), 3.08 (t, 2H, J=6.3 Hz), 1.91-1.84 (m, 4H).

1,8-Dihydroxy-3-(18'-chloro-aceta-6',9',12'-trioxa-2',16'-tridecanediamido)-anthraquinone (21)

Chloroacetyl chloride (24 μL, 0.3 mmol) was injected slowly into the solution of 20 (90 mg, 0.2 mmol) in anhydrous 1,4-dioxane (5 mL). The mixture was stirred at room temperature for 30 minutes. The reaction was followed by TLC (DCM:MeOH=10:1). The organic layer was concentrated in vacuo. The residue was purified using silica gel column chromatography. The compound was eluted with DCM:methanol (60:1). Orange color solid was obtained as product (11 mg, 30% yield). $^1$H NMR (DMSO-$d_6$): δ 8.23 (s, 1H), 7.86-7.81 (m, 1H), 7.79-7.73 (m, 2H), 7.45-7.41 (m, 1H), 4.01 (s, 2H), 3.42-3.51 (m, 14H), 3.40 (t, 2H, J=6.0 Hz), 3.15-3.10 (m, 2H), 1.73 (t, 2H, J=6.2 Hz), 1.67 (t, 2H, J=6.2 Hz); MS: m/z [M–H]$^+$ calculated $C_{22}H_{31}ClN_2O_9$ 563.1, found 563.3.

1,8-Dihydroxy-3-(18'-bromo-aceta-6',9',12'-trioxa-2',16'-tridecanediamido)-anthraquinone (22)

Bromoacetyl N-hydroxy succinimide (79 mg, 0.3 mmol) was injected slowly into the solution of (20) (80 mg, 0.2 mmol) in anhydrous 1,4-dioxane (5 mL). The mixture was stirred at room temperature for 1 hour. The reaction was followed by TLC (DCM:MeOH=10:1), and 0.5 equivalent of TEA was added. The reaction was diluted by $H_2O$ (2 mL) and the suspension was extracted with $CH_2Cl_2$ (2×20 mL). The organic layers were combined, dried over $MgSO_4$, filtered and concentrated in vacuo. The residue was purified using silica gel column chromatography. The compound was eluted with DCM:methanol (1:0, 60:1). Orange color solid was obtained as product (47 mg, 39% yield). $^1$H NMR (DMSO-$d_6$): δ 11.90 (s, 2H), 8.18 (s, 1H), 7.83 (t, 1H, J=8.4 Hz), 7.61-7.45 (m, 2H), 7.42-7.40 (m, 1H), 4.02 (s, 2H), 3.52-3.45 (m, 14H), 3.39 (t, 2H, J=6.2 Hz), 3.17-3.08 (m, 2H), 1.82-1.75 (m, 2H), 1.67-1.61 (m, 2H); MS: m/z [M–H]$^-$ calculated $C_{27}H_{31}BrN_2O_9$ 607.1, found 606.3.

1,8-Dihydroxy-3-(18'-iodo-aceta-6',9',12'-trioxa-2',16'-tridecanediamido)-anthraquinone (23)

Iodoacetyl chloride (25 μL, 0.3 mmol) was injected slowly into the solution of 20 (90 mg, 0.2 mmol) in anhydrous 1,4-dioxane (5 mL). The mixture was stirred at room temperature for 1 hour. The reaction was followed by TLC (DCM:MeOH=10:1). The organic layer was concentrated in vacuo. The residue was purified using silica gel column chromatography. The product was eluted with DCM:methanol (60:1). Orange color solid was obtained as product (26 mg, 20% yield). $^1$H NMR (DMSO-$d_6$): δ 8.12 (d, 1H, J=1.6), 7.79-7.73 (m, 2H), 7.68-7.67 (m, 1H), 7.33-7.31 (m, 1H), 3.68-3.60 (m, 11H), 3.57-3.47 (m, 7H), 3.36-3.31 (m, 1H), 3.26-3.21 (m, 1H), 1.94-1.88 (m, 2H), 1.80-1.71 (m, 2H); MS: m/z [M–H]$^+$ calculated $C_{27}H_{31}IN_2O_9$ 655.1, found 655.3.

General Procedure for the Synthesis of 24a, 26a-f by Thiophenol Demethylation

The mixture of 1,8-dimethoxy-anthraquinone compounds (0.07 mmol), PhSH (0.40 mmol), and K2CO3 (0.40 mmol) in dry NMP (4 mL) was heated at 140-160° C. for 20-60 min under $N_2$. The mixture was then diluted with $H_2O$ (150 mL). The aqueous suspension was extracted with ethyl acetate (100 mL×3). The organic layers were combined and concentrated in vacuo. The residue was purified on a silica gel column using ethyl acetate/hexane solvent system as the eluent.

1,8-Dihydroxy-3-(phenylthio)-anthraquinone (24a)

Yield: 10 mg, 54%. $^1$H NMR (CDCl$_3$): δ=12.10 (s, 1H), 12.09 (s, 1H), 7.80-7.77 (dd, 1H, $J_1$=1.2 Hz, $J_2$=7.6 Hz), 7.65 (t, 1H, J=8.0 Hz), 7.60-7.57 (m, 3H), 7.50 (d, 2H, J=1.6 Hz), 7.48 (d, 1H, J=1.6 Hz), 7.30-7.27 (dd, 1H, $J_1$=1.2 Hz, $J_2$=7.6 Hz), 6.80 (d, 1H, J=1.6 Hz); $^{13}$C NMR (CDCl$_3$): δ=192.0, 181.8, 163.1, 162.6, 152.9, 137.1, 135.5, 133.6, 133.5, 130.4, 129.4, 125.0, 120.2, 119.6, 118.1, 116.1, 113.2; HRMS: m/z [M–H]$^-$ calcd for $C_{20}H_{11}O_4S$, 347.0378, found 347.0377.

1,8-Dihydroxy-3-(3',5'-dimethyl-isoxazol-4'-yl)-anthraquinone (26a)

Yield: 10 mg, 41%. $^1$H NMR (CDCl$_3$): δ=12.12 (s, 1H), 12.06 (s, 1H), 7.85 (d, 1H, J=7.2 Hz), 7.75 (d, 1H, J=1.6 Hz), 7.72 (t, 1H, J=8.0 Hz), 7.33 (d, 1H, J=7.6 Hz), 7.20 (d, 1H, J=1.6 Hz), 2.53 (s, 3H), 2.38 (s, 3H); $^{13}$C NMR (CDCl$_3$): δ=192.7, 181.7, 167.1, 163.0, 162.8, 140.4, 137.6, 134.3, 133.7, 125.1, 123.8, 120.4, 120.3, 116.0, 115.3, 115.0, 12.3, 11.3; HRMS: m/z [M–H]$^-$ calcd for $C_{19}H_{12}O_5N$, 334.0715, found 334.0709.

1,8-Dihydroxy-3-(thiophen-2'-yl)-anthraquinone (26b)

Yield: 10 mg, 47%. $^1$H NMR (CDCl$_3$): δ=12.05 (s, 2H), 8.07 (s, 1H), 7.86 (d, 1H, J=6.8 Hz), 7.66 (t, 1H, J=7.6 Hz), 7.58 (s, 1H), 7.46 (m, 2H), 7.29 (d, 1H, J=8.0 Hz), 7.15 (s, 1H); $^{13}$C NMR (CDCl$_3$): δ=192.4, 181.9, 163.6, 163.0, 143.4, 142.1, 137.2, 134.7, 134.1, 128.9, 128.5, 126.7, 125.0, 120.3, 119.8, 117.7, 116.4, 115.0; HRMS: m/z [M–H]$^-$ calcd for $C_{18}H_9O_4S$, 321.0222, found 321.0236.

1,8-Dihydroxy-3-(4'-dimethylamino-3'-methylphenyl)-anthraquinone (26c)

Yield: 20 mg, 71%. $^1$H NMR (CDCl$_3$): δ=12.13 (s, 1H), 12.05 (s, 1H), 8.03 (s, 1H), 7.81 (d, 1H, J=7.2 Hz), 7.64 (t, 1H, J=8.4 Hz), 7.53-7.49 (m, 2H), 7.42 (s, 1H), 7.26 (d, 1H, J=8.4 Hz), 7.06 (d, 1H, J=8.0 Hz), 2.80 (s, 6H), 2.40 (s, 3H); $^{13}$C NMR (CDCl$_3$): δ=192.3, 182.1, 163.2, 162.6, 154.5, 150.0, 137.0, 133.9, 133.8, 132.2, 131.4, 130.3, 125.5, 124.7, 120.7, 120.2, 118.7, 118.6, 116.2, 114.2, 44.0, 19.2; HRMS: m/z [M+H]$^+$ calcd for $C_{23}H_{20}O_4N$, 374.1392, found 374.1397.

1,8-Dihydroxy-3-(6'-phenylthio-pyridin-3'-yl)-anthraquinone (26d)

Yield: 11 mg, 47%. $^1$H NMR (CDCl$_3$): δ=12.01 (s, 1H), 11.98 (s, 1H), 8.76 (s, 1H), 8.00 (d, 1H, J=1.6 Hz), 7.83 (dd, 1H, $J_1$=1.2 Hz, $J_2$=7.6 Hz), 7.74 (dd, 1H, $J_1$=2.4 Hz, $J_2$=8.4 Hz), 7.68-7.62 (m, 3H), 7.45-7.43 (m, 4H), 7.29 (dd, 1H, $J_1$=1.2 Hz, $J_2$=8.4 Hz), 7.03 (d, 1H, J=8.4 Hz); $^{13}$C NMR (CDCl$_3$): δ=192.8, 181.7, 163.6, 163.4, 163.0, 148.2, 146.7, 137.5, 135.4, 135.1, 134.8, 134.0, 130.9, 130.5, 130.0, 129.7, 125.1, 121.5, 121.4, 120.4, 118.4, 116.3, 115.5; HRMS: m/z [M+H]$^+$ calcd for $C_{25}H_{16}NO_4S$, 426.0800, found 426.0800.

1,8-Dihydroxy-3-(4'-t-butoxymethyl-phenyl)-anthraquinone (26e)

Yield: 22 mg, 78%. $^1$H NMR (CDCl$_3$): δ=12.08 (s, 1H), 12.04 (s, 1H), 8.04 (d, 1H, J=1.6 Hz), 7.81 (dd, 1H, $J_1$=1.2 Hz, $J_2$=7.6 Hz), 7.67-7.63 (m, 3H), 7.48 (s, 1H), 7.45 (m, 2H), 7.27 (dd, 1H, $J_1$=1.2 Hz, $J_2$=7.6 Hz), 4.51 (s, 2H), 1.33 (s, 9H); $^{13}$C NMR (CDCl$_3$): δ=192.6, 181.9, 163.1, 162.7, 150.0, 141.9, 137.2, 137.1, 134.0, 133.8, 128.2, 127.4, 124.8, 121.7, 120.3, 119.0, 116.1, 114.7, 73.9, 63.9, 27.9; HRMS: m/z [M+H]$^+$ calcd for $C_{25}H_{23}O_5$ 403.1545, found 403.1543.

1,8-Dihydroxy-3-(4'-methoxyphenyl)-anthraquinone (26f)

Yield: 18 mg, 61%. $^1$H NMR (CDCl$_3$): δ=12.06 (s, 1H), 12.00 (s, 1H), 8.05 (d, 1H, J=1.6 Hz), 7.83 (d, 1H, J=7.2 Hz), 7.64 (m, 3H, $J_1$=8.8 Hz, $J_2$=7.2 Hz), 7.44 (d, 1H, J=1.6 Hz), 7.27 (d, 1H, J=8.4 Hz), 7.00 (d, 2H, J=8.8 Hz), 3.87 (s, 3H); $^{13}$C NMR (CDCl$_3$): δ=192.7, 182.1, 163.5, 162.9, 161.4, 150.0, 137.1, 134.4, 134.2, 131.0, 128.8, 124.8, 121.0, 120.2, 118.7, 116.5, 115.0, 114.6, 55.7; HRMS: m/z [M−H]$^-$ calcd for $C_{21}H_{13}O_5$ 345.0763, found 345.0767.

1,8-Dihydroxy-3-(4'-hydroxyphenyl)-anthraquinone (26g)

The mixture of 6f (15 mg, 0.043 mmol), PhSH (13 μL, 0.13 mmol), and K$_2$CO$_3$ (36 mg, 0.26 mmol) in dry NMP (1 mL) was heated at 170-180° C. for 1 h under N$_2$. The mixture was then diluted with H$_2$O and acidified with HCl (5 M). The aqueous suspension was extracted with ethyl acetate and then concentrated in vacuo. The residue was purified with silica gel column using ethyl acetate/hexane (1:4). Yield: 4 mg, 28%. $^1$H NMR (DMSO): δ=11.97 (s, 2H), 9.99 (s, 1H), 7.90 (d, 1H, J=1.6 Hz), 7.80 (t, 1H, J=8.0 Hz), 7.73-7.70 (m, 3H), 7.56 (d, 1H, J=1.6 Hz), 7.38 (dd, 1H, $J_1$=1.2 Hz, $J_2$=8.0 Hz), 6.92 (d, 2H, J=8.4 Hz); $^{13}$C NMR (DMSO): δ=191.2, 181.4, 162.1, 161.3, 159.2, 148.6, 137.3, 133.7, 133.3, 128.6, 127.8, 124.5, 119.6, 119.4, 116.7, 116.1, 114.0; HRMS: m/z [M−H]$^-$ calcd for $C_{20}H_{11}O_5$ 331.0606, found 331.0614.

1,8-Dihydroxy-3-amino-anthraquinone (MG10)

The mixture of 3 (1.7 g, 6.0 mmol), PhSH (3.3 mL, 30 mmol), and K$_2$CO$_3$ (4.1 g, 30 mmol) in dry NMP (100 mL) was heated at 150-160° C. for 1 h under N$_2$. The mixture was then diluted with CH$_2$Cl$_2$ and washed with brine. The organic layer was concentrated in vacuo. The residue was diluted with H$_2$O (250 mL) and hexane (250 mL). Deep red precipitate was formed in the organic/aqueous interface and collected by filtration as product (1.5 g, 98%). $^1$H NMR (DMSO): δ=12.42 (s, 1H), 12.23 (s, 1H), 7.70-7.63 (m, 2H), 7.30 (d, 1H, J=8.0 Hz), 7.16 (s, 2H), 7.04 (s, 1H), 6.25 (s, 1H); $^{13}$C NMR (DMSO): δ=187.5, 181.9, 164.9, 161.0, 157.5, 135.9, 134.7, 133.1, 124.3, 119.0, 115.9, 108.6, 105.4, 102.0; HRMS: m/z [M−H]$^-$ calcd for $C_{14}H_8O_4N$, 254.0453, found 254.0441.

General Procedure for the Synthesis of 9a-d

The mixture of 3 (MG1) (0.3 mmol) and a secondary amine (1.5 mmol) in dry dioxane (9 mL) was heated at 80-90° C. for 2 h. The reaction mixture was concentrated in vacuo and the residue was dissolved in a minimal amount of CH$_2$Cl$_2$. The solution was then diluted with hexane (2 times volume) and stored at −20° C. Precipitation was observed. Yellow solid was obtained as product after filtration.

1,8-Dihydroxy-3-(2'-diethylamino-acetamido)-anthraquinone (9a)

Yield: 42 mg, 36%. $^1$H NMR (CDCl$_3$): δ=12.16 (s, 2H), 9.90 (s, 1H), 8.03 (d, 1H, J=2.0 Hz), 7.82 (d, 1H, J=7.6 Hz), 7.66 (t, 1H, $J_1$=7.6 Hz, $J_2$=8.4 Hz), 7.57 (d, 1H, J=2.0 Hz), 7.29 (d, 1H, J=8.4 Hz), 3.21 (s, 2H), 2.69 (q, 4H, J=7.2 Hz), 1.12 (t, 6H, J=7.2 Hz); $^{13}$C NMR (CDCl$_3$): δ=191.4, 181.9, 171.2, 164.9, 162.7, 145.6, 136.9, 134.8, 133.7, 125.1, 120.2, 116.1, 112.5, 112.1, 111.2, 58.2, 49.2, 12.6; HRMS: m/z [M−H]$^-$ calcd for $C_{20}H_{19}O_5N_2$ 367.1294, found 367.1296.

1,8-Dihydroxy-3-(2'-(4''-methylpiperazin-1''-yl)-acetamido)-anthraquinone (9b)

Yield: 54 mg, 45%. $^1$H NMR (DMSO): δ=11.97 (s, 2H), 10.51 (s, 1H), 7.97 (d, 1H, J=2.0 Hz), 7.80-7.76 (m, 2H), 7.72-7.70 (dd, 1H, $J_1$=1.2 Hz, $J_2$=7.6 Hz), 7.37-7.35 (dd, 1H, $J_1$=1.2 Hz, $J_2$=8.4 Hz), 3.38 (s, 2H), 3.22 (s, 4H), 2.90 (s, 4H), 2.75 (s, 3H); $^{13}$C NMR (DMSO): δ=190.0, 180.9, 168.9, 162.7, 161.1, 146.2, 136.7, 134.0, 133.1, 124.1, 119.1, 115.6, 111.3, 110.9, 59.8, 52.3, 48.8, 42.0; HRMS: m/z [M+H]$^+$ calcd for $C_{21}H_{22}O_5N_3$ 396.1559, found 396.1556.

1,8-dihydroxy-3-(2'-morpholino-acetamido)-anthraquinone (9c)

Yield: 100 mg, 82%. $^1$H NMR (DMSO): δ=11.80-11.40 (s, broad, 2H), 10.47 (s, 1H), 7.90 (d, 1H, J=2.0 Hz), 7.78-7.74 (m, 2H), 7.66 (d, 1H, J=7.2 Hz), 7.33 (d, 1H, J=8.4 Hz), 3.66 (t, 4H, J=4.4 Hz), 3.22 (s, 2H), 2.54 (t, 4H, J=4.4 Hz); $^{13}$C NMR (DMSO): δ=190.2, 181.1, 169.6, 163.0, 161.3, 146.5, 137.0, 134.1, 133.2, 124.4, 119.4, 115.7, 111.4, 111.1, 66.0, 62.0, 53.1; HRMS: m/z [M+H]$^+$ calcd for $C_{20}H_{19}O_6N_2$ 383.1243, found 383.1228.

1,8-Dihydroxy-3-(2'-piperidinyl-acetamido)-anthraquinone (9d)

Yield: 55 mg, 47%. $^1$H NMR (DMSO): δ=12.50-11.50 (s, broad, 2H), 9.65 (s, 1H), 7.92 (d, 1H, J=2.0 Hz), 7.81-7.78 (dd, 2H, $J_1$=1.2 Hz, $J_2$=7.6 Hz), 7.64-7.60 (m, 2H), 7.27-7.25 (d, 1H, J=8.4 Hz), 3.11 (s, 2H), 2.58 (t, 4H, J=5.2 Hz), 1.69 (m, 4H), 1.53 (t, 2H, J=5.6 Hz); $^{13}$C NMR (DMSO): δ=191.6, 181.8, 169.9, 165.0, 162.9, 145.9, 136.9, 135.1, 134.0, 125.0, 120.2, 116.3, 112.7, 112.3, 111.3, 63.1, 55.3, 26.5, 23.8; HRMS: m/z [M+H]$^+$ calcd for $C_{21}H_{21}O_5N_2$ 381.1450, found 381.1442.

Example 2. Synthesis of 1,8-dimethoxy Rhein Analogs 1,8-dimethoxy-3-(2'-chloro-acetamido)-anthraquinone (12)

Chloroacetyl chloride (21 µL, 0.2 mmol) was injected slowly into the solution of (11) (50 mg, 0.17 mmol) in anhydrous 1,4-dioxane (5 mL). The mixture was stirred at room temperature for 2 h. The reaction was followed by TLC (DCM:MeOH=10:1), and after completion was diluted by H$_2$O (20 mL) and the suspension was extracted with CH$_2$Cl$_2$ (2×50 mL). The organic layers were combined, dried over MgSO$_4$, filtered and concentrated in vacuo. The residue was purified with silica gel column chromatography. It was eluted with DCM:MeOH (60:1). Orange color solid was obtained as product (8 mg, 30% yield). $^1$H NMR (DMSO-d$_6$): δ 10.81 (s, 1H), 7.93 (d, 1H, J=2.0 Hz), 7.82 (d, 1H, J=2.0 Hz), 7.76-7.682 (m, 2H), 7.55-7.529 (m, 1H), 4.34 (s, 2H), 3.93 (d, 6H, J=7.6 Hz); MS: m/z [M+H]$^+$ calculated $C_{18}H_{14}ClNO_5$ 360.0, found 360.2.

1,8-dimethoxy-3-(2'-bromo-acetamido)-anthraquinone (13)

Bromoacetyl bromide (23 µL, 0.26 mmol) was injected slowly into the solution of (11) (50 mg, 0.17 mmol) in anhydrous 1,4-dioxane (5 mL). The mixture was stirred at room temperature for 2 h. The reaction was followed by TLC (DCM:MeOH=10:1), and after completion was diluted by H$_2$O (20 mL) and the suspension was extracted with CH$_2$Cl$_2$ (2×50 mL). The organic layers were combined, dried over MgSO$_4$, filtered and concentrated in vacuo. The residue was purified with silica gel column chromatography. The compound was eluted with DCM:MeOH (1:0, 60:1). Orange color solid was obtained as product (13 mg 20% yield). $^1$H NMR (DMSO-d$_6$): δ 10.95 (s, 1H), 7.91 (d, 1H, J=2.0 Hz), 7.82 (d, 1H, J=2.0 Hz), 7.76-7.68 (m, 2H), 7.55-7.53 (m, 1H), 4.10 (s, 2H), 3.95 (d, 6H, J=7.2 Hz); MS: m/z [M+H]$^+$ calculated $C_{18}H_{14}BrNO_5$ 405.2, found 405.2.

1,8-dimethoxy-3-(2'-iodo-acetamido)-anthraquinone (14)

Iodoacetyl chloride (24 µL, 0.26 mmol) was injected slowly into the solution of (11) (50 mg, 0.17 mmol) in anhydrous 1,4-dioxane (5 mL). The mixture was stirred at room temperature for 2 h. The reaction was followed by TLC (DCM:MeOH=10:1), and after completion was diluted by H$_2$O (20 mL) and the suspension was extracted with CH$_2$Cl$_2$ (2×50 mL). The organic layers were combined, dried over MgSO$_4$, filtered and concentrated in vacuo. The residue was purified with silica gel column chromatography. The residue was eluted with DCM:MeOH (1:0:60:1). Orange color solid was obtained as product (27 mg, 35% yield). $^1$H NMR (DMSO-d$_6$): δ 7.92 (d, 1H, J=2.0 Hz), 7.78 (d, 1H, J=2.0 Hz), 7.76-7.66 (m, 2H), 7.48-7.46 (m, 1H), 3.93 (d, 6H, J=5.2 Hz), 3.87 (s, 2H); MS: m/z [M+H]$^+$ calculated $C_{18}H_{14}INO_5$ 451.9, found 452.0.

1,8-Dimethoxy-3-methylcarboxylate-anthraquinone

Rhein (10 g, 35 mmol) was suspended in dry DMF (300 mL) in a round bottom flask and cooled down in an ice-bath under N$_2$. Sodium hydride (9 g, 60% dispersed in mineral oil, 225 mmol) was then added. The mixture's color turned from yellow to deep red. The reaction flask outlet was connected to a bubbler sealed with mineral oil. As the bubbling reached a steady and slow speed, iodomethane (18 mL, 290 mmol) was added through a syringe in one-shot. The mixture was kept in an ice-bath. The reaction temperature was slowly increased to room temperature as the ice melting away. After stirring overnight, the reaction mixture was diluted with H$_2$O (1 L). The aqueous suspension was repeatedly extracted with CH$_2$Cl$_2$. The organic layers were combined and concentrated into about 250 mL. MeOH (4 times volume) was added to dilute the solution and the mixture was cooled at 4° C. in a refrigerator. The precipitate from the solution was filtered to give yellow solid as the product (8.9 g, 77%). $^1$H NMR (CDCl$_3$): δ=8.46 (d, 1H, J=1.6 Hz), 7.94 (d, 1H, J=1.2 Hz), 7.87-7.85 (dd, 1H, J$_1$=0.8 Hz, J$_2$=7.6 Hz), 7.67 (t, 1H, J=8.0 Hz), 7.32 (d, 1H, J=8.4 Hz), 4.07 (s, 3H), 4.02 (s, 3H), 4.00 (s, 3H); $^{13}$C NMR (CDCl$_3$): δ=183.3, 182.4, 165.6, 159.7, 135.0, 134.9, 134.8, 134.4, 126.9, 124.0, 120.0, 119.2, 118.4, 118.3, 56.9, 56.7, 52.9; HRMS: m/z [M+H]$^+$ calcd for $C_{18}H_{15}O_6$ 327.0869, found 327.0857.

1,8-Dimethoxy-3-carboxy-anthraquinone 1,8-Dimethoxy-3-methylcarboxylate-anthraquinone (8.9 g, 27 mmol) was suspended in EtOH (45 mL). NaOH solution in EtOH/H$_2$O (0.46 M, 90 mL, 1:1 v/v) was then added. The mixture was stirred at 50° C. for 1 h, and the reaction color turned from yellow to deep red. The suspension was cooled down in an ice-bath and acidified with HCl (1 M). The solution color changed to light yellow and precipitation was observed. The precipitation was filtered to give yellow solid as the product (8.9 g, 100%). $^1$H NMR (DMSO): δ=8.17 (d, 1H, J=1.6 Hz), 7.89 (d, 1H, J=1.2 Hz), 7.76-7.69 (m, 2H), 7.54 (d, 1H, J=8.0 Hz), 3.99 (s, 3H), 3.93 (s, 3H); $^{13}$C NMR (DMSO): δ=182.5, 180.6, 165.6, 158.8, 158.7, 135.4, 134.3, 134.2, 133.9, 126.1, 123.4, 119.1, 118.4, 118.2, 118.1, 56.4, 56.3; HRMS: m/z [M–H]$^-$ calcd for $C_{12}H_{12}O_6$ 311.0556, found 311.0547.

1,8-Dimethoxy-anthraquinone-3-carboxyl azide (2)

1,8-Dimethoxy-3-carboxy-anthraquinone (8.9 g, 28 mmol) was dissolved in DMF (93 mL) together with Et$_3$N (4.1 mL, 57 mmol). The solution turned into burgundy color and was cooled down in an ice-bath. Diphenylphosphoryl azide (6.2 mL, 29 mmol) was added dropwise into the solution while stirring. Afterwards, the solution was stirred at r.t. for 1 h and diluted by H$_2$O (1.2 L). The suspension was filtered to give light yellow solid as the product (9.0 g, 94%). $^1$H NMR (CDCl$_3$): δ=8.43 (d, 1H, J=1.6 Hz), 7.90 (d, 1H, J=1.2 Hz), 7.86-7.84 (dd, 1H, J$_1$=0.8 Hz, J$_2$=7.6 Hz), 7.67 (t, 1H, J=8.0 Hz), 7.33 (d, 1H, J=8.0 Hz), 4.07 (s, 3H), 4.02 (s, 3H); $^{13}$C NMR (CDCl$_3$): δ=183.1, 182.3, 171.4, 159.9, 159.8, 135.3, 135.1, 134.7, 134.6, 127.8, 124.0, 120.0, 119.3, 118.5, 117.6, 57.1, 56.8; HRMS: m/z [M+H]$^+$ calcd for $C_{17}H_{12}N_3O_5$ 338.0777, found 338.0769.

1,8-Dimethoxy-3-amino-anthraquinone (3a)

Acyl azide 2 (9.0 g, 27 mmol) was refluxed in dry dioxane (200 mL) for 30 min under N$_2$. TLC monitoring showed the disappearance of 2. The mixture was concentrated in vacuo and diluted with NaOH (aq) solution (1M, 400 mL). The suspension was refluxed for 4 h and then cooled down to r.t.

The precipitation from the solution was filtered and washed with acetone. The filtrated solution was extracted repeatedly with $CH_2Cl_2$. The organic layers were combined and concentrated to give deep red solid as the product (4.0 g, 53%). $^1H$ NMR ($CDCl_3$): δ=7.78 (d, 1H, J=7.6 Hz), 7.55 (t, 1H, J=8.0 Hz), 7.25 (m, 1H), 7.03 (d, 1H, J=2.0 Hz), 6.44 (d, 1H, J=2.0 Hz), 3.96 (s, 3H), 3.91 (s, 3H); $^{13}C$ NMR ($CDCl_3$): δ=184.8, 181.8, 162.3, 159.8, 151.9, 136.6, 135.0, 133.3, 124.5, 119.1, 118.6, 115.7, 104.7, 102.7, 56.8, 56.5; HRMS: m/z $[M+H]^+$ calcd for $C_{16}H_{14}NO_4$ 284.0923, found 284.0914.

1,8-Dimethoxy-3-iodo-anthraquinone (4)

Aminoanthraquinone 3a (2.0 g, 7.1 mmol), isopentyl nitrite (6.0 mL, 45 mmol) and diiodomethane (15 mL, 186 mmol) were mixed and stirred in dry THF (200 mL) at 50-60° C. for 2 days under $N_2$. The mixture was concentrated in vacuo and the residue was purified on a silica gel column. The product was eluted with ethyl acetate/hexane (1:1). After removal of the solvent, yellow solid was obtained as product (1.4 g, 50%). $^1H$ NMR ($CDCl_3$): δ=8.14 (d, 1H, J=1.6 Hz), 7.80-7.78 (dd, 1H, $J_1$=0.8 Hz, $J_2$=8.0 Hz), 7.64 (t, 1H, J=8.0 Hz), 7.60 (d, 1H, J=1.2 Hz), 7.30 (d, 1H, J=8.0 Hz), 4.00 (s, 3H), 3.99 (s, 3H); $^{13}C$ NMR ($CDCl_3$): δ=182.9, 182.3, 159.7, 159.6, 135.0, 134.3, 128.2, 127.1, 123.8, 123.3, 119.2, 118.5, 100.7, 57.0, 56.7; HRMS: m/z $[M+H]^+$ calcd for $C_{16}H_{12}O_4I$ 394.9780, found 394.9785.

General Procedure for the Synthesis of 25a-i by Suzuki Coupling of 4 with $RB(OH)_2$ The mixture of 4 (0.13 mmol), $RB(OH)_2$ (0.23 mmol), $Pd(PPh_3)_4$ (0.013 mmol) and $K_2CO_3$ (0.38 mmol) in dry DMF (5 mL) was heated at 70-80° C. for 1 h to overnight under $N_2$. The mixture was then diluted with $CH_2Cl_2$ (40 mL) and washed with $H_2O$ (50 mL, twice or three times). The organic layer was concentrated in vacuo and the residue was purified on a silica gel column. The product was eluted with ethyl acetate/hexane or ethyl acetate/$CH_2Cl_2$ solvent system. After removal of the solvent, the solid was further purified by dissolving in a minimal amount of $CH_2Cl_2$ and then precipitation through hexane addition.

1,8-Dimethoxy-3-(3',5'-dimethyl-isoxazol-4'-yl)-anthraquinone (25a)

Yield: 50 mg, 92%. $^1H$ NMR ($CDCl_3$): δ=7.84-7.82 (dd, 1H, $J_1$=0.8 Hz, $J_2$=7.6 Hz), 7.73 (d, 1H, J=1.6 Hz), 7.65 (t, 1H, J=8.0 Hz), 7.34-7.31 (dd, 1H, $J_1$=0.8 Hz, $J_2$=8.4 Hz), 7.14 (d, 1H, J=1.6 Hz), 4.02 (s, 3H), 4.01 (s, 3H), 2.48 (s, 3H), 2.33 (s, 3H); $^{13}C$ NMR ($CDCl_3$): δ=183.9, 182.5, 166.5, 160.0, 159.7, 158.3, 136.7, 135.3, 134.8, 134.2, 124.0, 123.2, 119.3, 119.2, 118.5, 118.2, 115.8, 56.8, 56.7, 12.0, 11.1; HRMS: m/z $[M+H]^+$ calcd for $C_{21}H_{18}NO_5$ 364.1185, found 364.1169.

1,8-Dimethoxy-3-(thiophen-2'-yl)-anthraquinone (25b)

Yield: 45 mg, 87%. $^1H$ NMR ($CDCl_3$): δ=8.08 (d, 1H, J=2.0 Hz), 7.87-7.85 (dd, 1H, $J_1$=0.8 Hz, $J_2$=7.6 Hz), 7.65 (t, 1H, J=8.0 Hz), 7.55-7.54 (dd, 1H, $J_1$=1.2 Hz, $J_2$=3.6 Hz), 7.46 (d, 1H, J=1.2 Hz), 7.43-7.42 (dd, 1H, $J_1$=0.8 Hz, $J_2$=5.2 Hz), 7.32 (d, 1H, J=8.0 Hz), 7.17-7.15 (dd, 1H, $J_1$=4.8 Hz, $J_2$=3.6 Hz), 4.08 (s, 3H), 4.02 (s, 3H); $^{13}C$ NMR ($CDCl_3$): δ=184.1, 182.4, 160.4, 159.8, 142.5, 139.9, 135.5, 134.9, 134.0, 128.7, 127.3, 125.6, 124.2, 122.8, 119.2, 118.5, 116.3, 114.6, 56.8, 56.7; HRMS: m/z $[M+H]^+$ calcd for $C_{20}H_{15}O_4S$, 351.0691, found 351.0682.

1,8-Dimethoxy-3-(4'-dimethylamino-3'-methylphenyl)-anthraquinone (25c)

Yield: 63 mg, 100%. $^1H$ NMR ($CDCl_3$): δ=8.05 (d, 1H, J=1.6 Hz), 7.86-7.84 (dd, 1H, $J_1$=1.2 Hz, $J_2$=7.6 Hz), 7.62 (t, 1H, J=8.0 Hz), 7.51-7.48 (m, 2H), 7.45 (d, 1H, J=1.6 Hz), 7.31-7.29 (dd, 1H, $J_1$=0.8 Hz, $J_2$=8.4 Hz), 7.10 (d, 1H, J=8.0 Hz), 7.17-7.15 (dd, 1H, $J_1$=4.8 Hz, $J_2$=3.6 Hz), 4.07 (s, 3H), 4.01 (s, 3H), 2.77 (s, 6H), 2.41 (s, 3H); $^{13}C$ NMR ($CDCl_3$): δ=184.4, 182.8, 160.3, 159.7, 153.8, 146.9, 135.1, 135.0, 133.9, 132.8, 132.4, 130.2, 125.4, 124.3, 122.2, 119.2, 118.8, 118.3, 117.3, 115.9, 56.8, 56.7, 44.1, 19.1; HRMS: m/z $[M+H]^+$ calcd for $C_{25}H_{24}O_4N$, 402.1705, found 402.1704.

1,8-Dimethoxy-3-(6'fluoropyridin-3'-yl)-anthraquinone (25d)

Yield: 46 mg, 99%. $^1H$ NMR ($CDCl_3$): δ=8.53 (d, 1H, J=1.6 Hz), 8.10 (td, 1H, $J_1$=2.0 Hz, $J_2$=8.0 Hz), 8.01 (d, 1H, J=1.6 Hz), 7.86 (d, 1H, J=8.0 Hz), 7.67 (t, 1H, J=8.0 Hz), 7.42 (s, 1H), 7.33 (d, 1H, J=8.4 Hz), 7.01-7.07 (dd, 1H, $J_1$=2.8 Hz, $J_2$=8.8 Hz), 4.09 (s, 3H), 4.03 (s, 3H); $^{13}C$ NMR ($CDCl_3$): δ=184.0, 182.5, 160.5, 159.8, 146.5, 146.3, 142.4, 140.2, 140.1, 135.6, 134.9, 134.3, 133.3, 124.1, 123.6, 119.3, 118.6, 117.6, 116.2, 110.3, 109.9, 57.0, 56.8; HRMS: m/z $[M+H]^+$ calcd for $C_{21}H_{15}NO_4F$ 364.0985, found 364.0977.

1,8-Dimethoxy-3-(4'-t-butoxymethyl-phenyl)-anthraquinone (25e)

Yield: 30 mg, 55%. $^1H$ NMR ($CDCl_3$): δ=8.06 (s, 1H), 7.85 (s, 1H, J=5.2 Hz), 7.65 (s, 3H), 7.47 (s, 3H), 7.30 (m, 1H), 4.52 (s, 2H), 4.07 (s, 3H), 4.01 (s, 3H), 1.32 (s, 9H); $^{13}C$ NMR ($CDCl_3$): δ=184.3, 182.8, 160.2, 159.7, 146.8, 141.1, 138.2, 135.2, 135.0, 134.0, 128.2, 127.3, 124.2, 122.7, 119.2, 118.3, 117.6, 116.4, 73.8, 63.9, 56.8, 56.7, 27.9; HRMS: m/z $[M+H]^+$ calcd for $C_{27}H_{27}O_5$ 431.1858, found 431.1863.

1,8-Dimethoxy-3-(4'-methoxyphenyl)-anthraquinone (25f)

Yield: 56 mg, 98%. $^1H$ NMR ($CDCl_3$): δ=8.03 (d, 1H, J=1.6 Hz), 7.86-7.84 (dd, 1H, $J_1$=1.2 Hz, $J_2$=7.6 Hz), 7.63 (m, 3H, $J_1$=8.4 Hz, $J_2$=7.6 Hz), 7.43 (d, 1H, J=2.0 Hz), 7.30 (d, 1H, J=8.4 Hz), 7.01 (d, 2H, J=8.8 Hz), 4.07 (s, 3H), 4.01 (s, 3H), 3.87 (s, 3H); $^{13}C$ NMR ($CDCl_3$): δ=184.4, 182.8, 160.5, 160.3, 159.7, 146.5, 135.2, 135.1, 134.0, 131.7, 128.6, 124.2, 122.3, 119.2, 118.4, 117.2, 115.8, 114.7, 56.8, 56.7, 55.6; HRMS: m/z $[M+H]^+$ calcd for $C_{23}H_{19}O_5$ 375.1232, found 375.1247.

1,8-Dimethoxy-3-(4'-acetylphenyl)-anthraquinone (25g)

Yield: 50 mg, 81%. $^1H$ NMR ($CDCl_3$): δ=8.07-8.05 (m, 3H, $J_1$=1.6 Hz, $J_2$=8.0 Hz), 7.85-7.83 (dd, 1H, $J_1$=0.8 Hz, $J_2$=7.6 Hz), 7.76 (d, 2H, J=8.4 Hz), 7.65 (t, 1H, $J_1$=8.4 Hz, $J_2$=7.6 Hz), 7.48 (d, 1H, J=1.6 Hz), 7.32 (d, 1H, J=8.0 Hz), 4.09 (s, 3H), 4.02 (s, 3H), 2.66 (s, 3H); $^{13}C$ NMR ($CDCl_3$): δ=197.7, 184.0, 182.6, 160.3, 159.8, 145.4, 143.7, 137.2, 135.3, 134.9, 134.2, 129.2, 127.6, 124.1, 123.4, 119.2, 118.4, 117.9, 116.5, 56.9, 56.7, 26.9; HRMS: m/z [M+H]$^+$ calcd for $C_{24}H_{19}O_5$ 387.1232, found 387.1241.

1,8-Dimethoxy-3-(furan-2'-yl)-anthraquinone (25h)

Yield: 34 mg, 78%. $^1$H NMR (CDCl$_3$): δ=8.06 (s, 1H), 7.83 (d, 1H, J=7.6 Hz), 7.61-7.52 (m, 3H), 7.27 (t, 1H, J$_1$=8.4 Hz, J$_2$=4.0 Hz), 6.88 (d, 1H, J=3.2 Hz), 6.52 (s, 1H), 4.05 (s, 3H), 3.99 (s, 3H); $^{13}$C NMR (CDCl$_3$): δ=184.0, 182.0, 160.7, 160.0, 152.6, 143.8, 136.0, 135.7, 135.2, 133.8, 124.8, 123.0, 119.4, 118.9, 114.7, 112.8, 112.5, 108.8, 56.9; HRMS: m/z [M+H]$^+$ calcd for $C_{20}H_{15}O_5$ 335.0919, found 335.0935.

1,8-Dimethoxy-3-(pyridin-3'-yl)-anthraquinone (25i)

Yield: 35 mg, 100%. $^1$H NMR (CDCl$_3$): δ=8.93 (s, 1H), 8.68 (s, 1H), 8.03 (d, 1H, J=1.6 Hz), 7.99 (d, 1H, J=8.0 Hz), 7.84 (d, 1H, J=7.6 Hz), 7.64 (t, 1H, J=8.0 Hz), 7.46 (d, 1H, J=1.2 Hz), 7.43 (m, 1H), 7.32 (d, 1H, J=8.4 Hz), 4.09 (s, 3H), 4.02 (s, 3H); $^{13}$C NMR (CDCl$_3$): δ=183.9, 182.5, 160.3, 159.7, 150.0, 148.3, 143.4, 135.4, 135.0, 134.8, 134.7, 134.2, 123.9, 123.3, 119.1, 118.4, 117.6, 116.2, 56.8, 56.7; HRMS: m/z [M+H]$^+$ calcd for $C_{21}H_{16}NO_4$ 346.1079, found 346.1084.

Example 3. MTT Assay

Figure 1A:
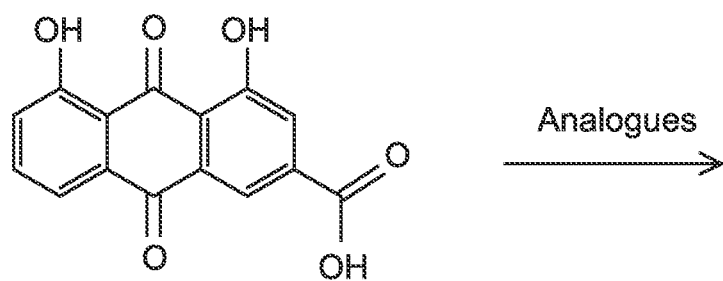
Figure 1A:
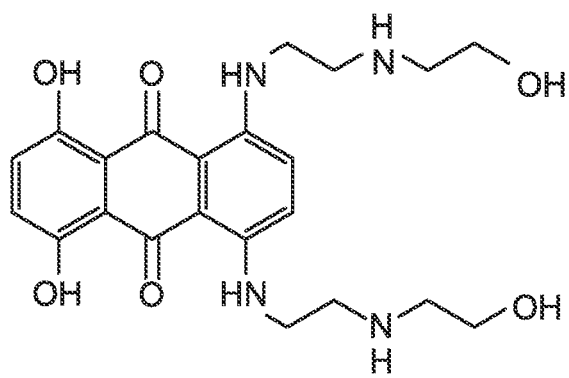
Figure 2A:
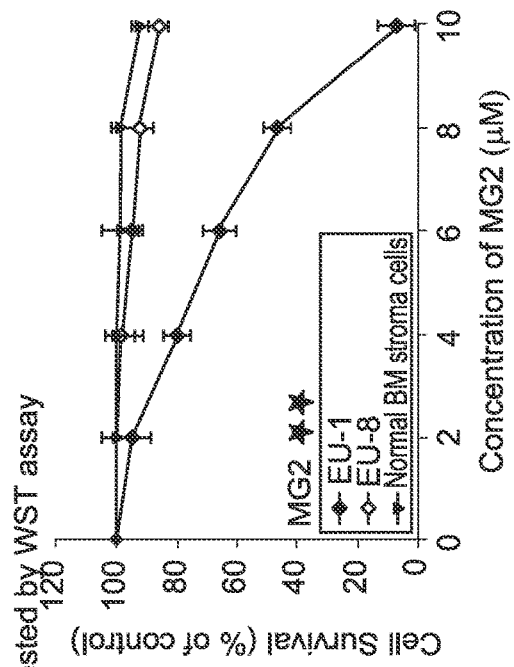
Figure 2B:
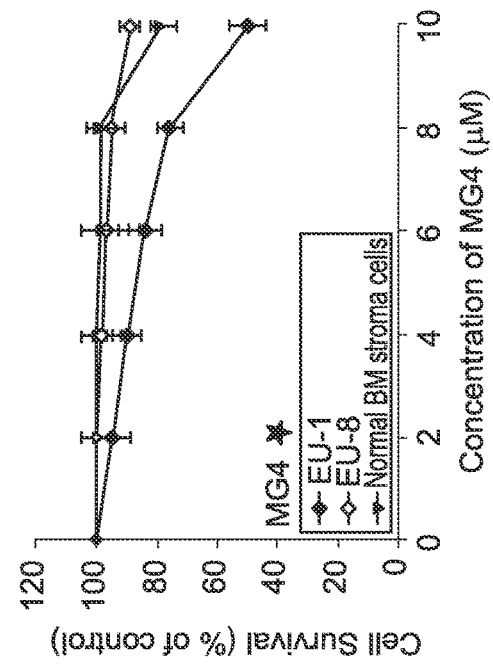
Figure 2C:
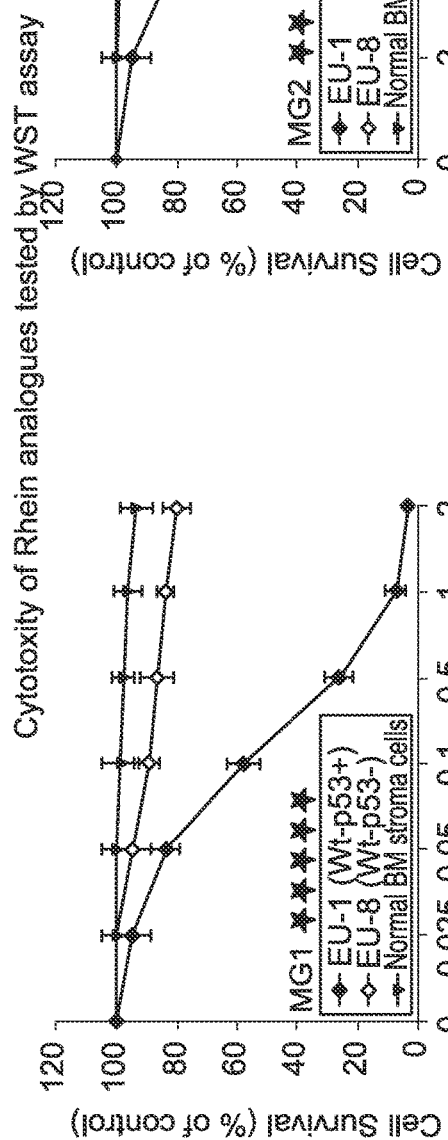
Figure 2D:
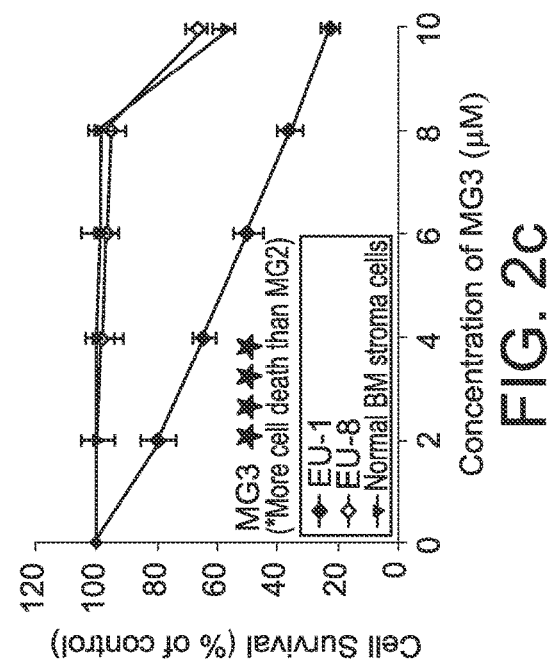
Figure 2E:
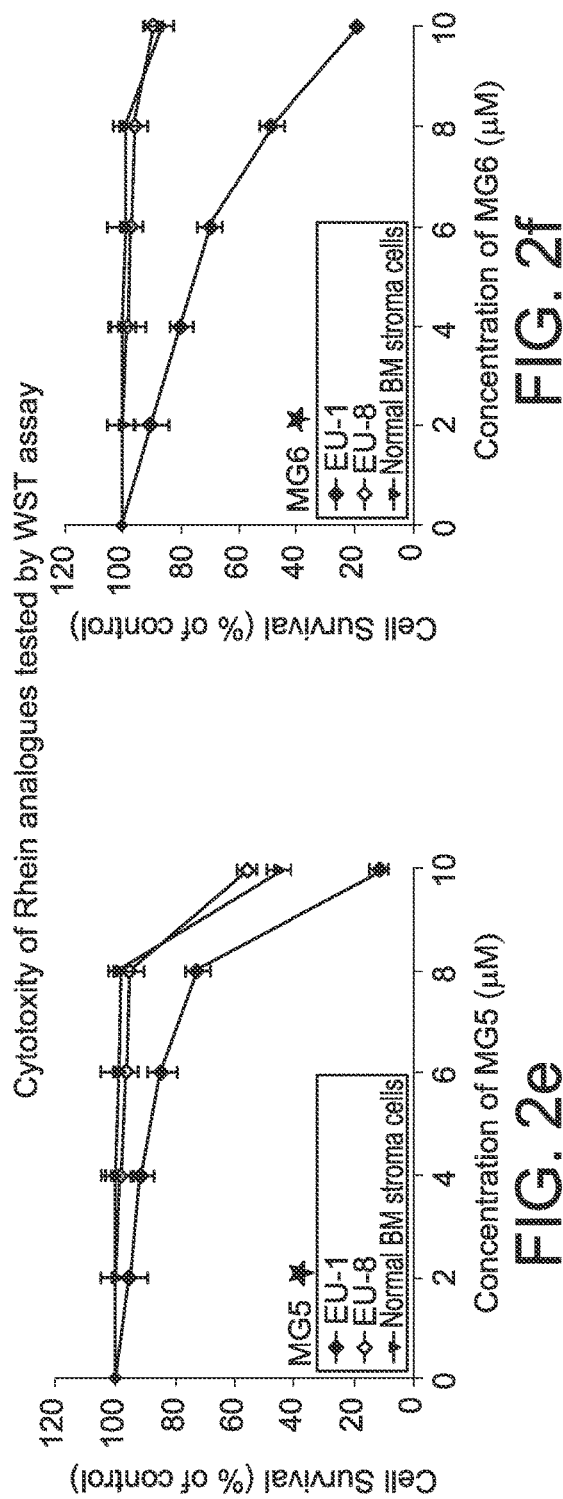
Figure 2F:
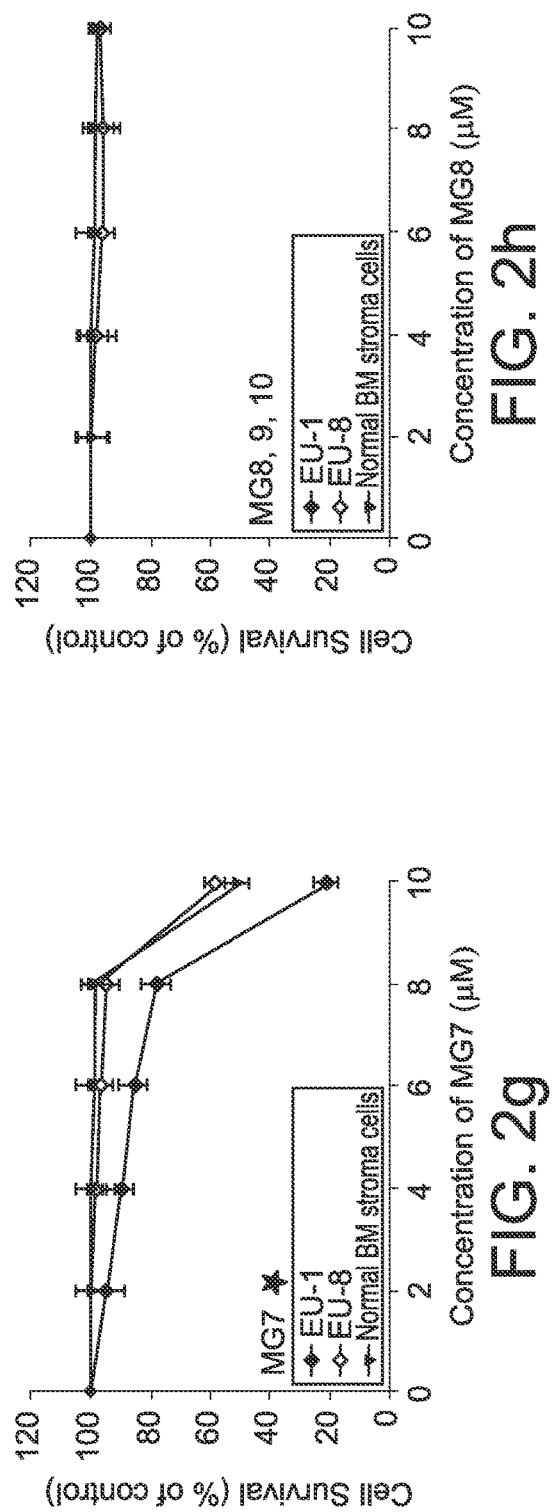
Figure 2G:
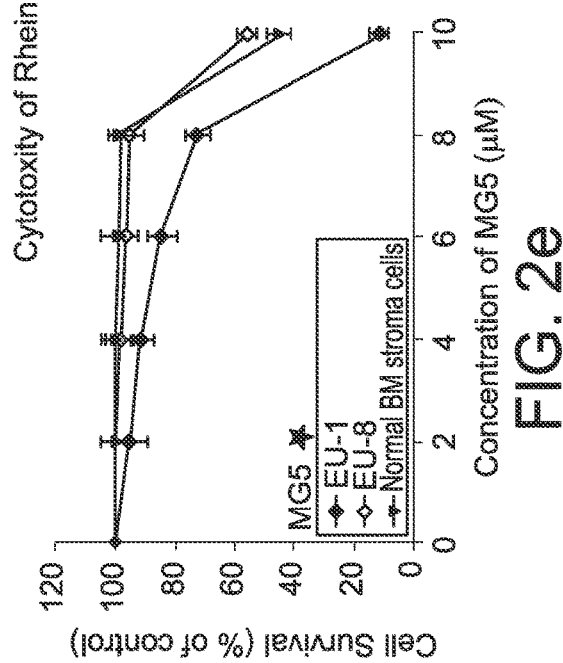
Figure 2H:
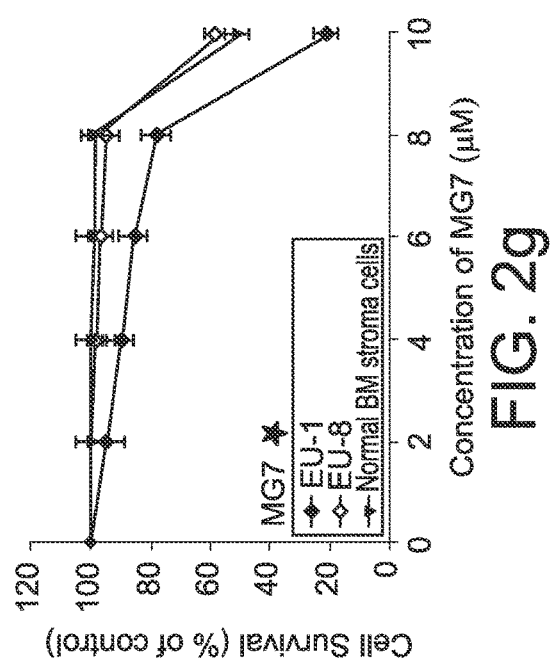

HeLa, Hek, and KB cell lines were purchased from ATCC. All of the cell lines were cultured in RPMI-1640 medium. The medium was supplemented with 10% fetal bovine serum and 1% penicillin/streptomycin. For the cytotoxicity assays, cells were seeded into 96-well plate (2.5× 10$^4$ in 100 µL per well for HeLa, 3.0×10$^4$ for KB, and 5×10$^4$ for Hek). The compounds were dissolved or suspended in DMSO to make 10 mM stock solutions. The structures of the compounds tested are shown in FIG. 1. The stock solution was diluted using DMSO to various concentrations. 1 µL of each concentration was diluted 100 fold with medium into the well plate keeping the DMSO<1% throughout the experiment. Addition of compounds was performed after adherent cells reached 40-50% confluence. After incubation for 48 h. at 37° C. in humidified atmosphere with 5% CO$_2$, 10 µL of MTT (5 mg/mL in PBS) was added. After addition of MTT the cells were incubated for another 4 h. The culture medium was then aspirated and 100 µL of DMSO was added to each well. The 96-well plate was read by microarray reader for optical density at 490 nm. All tests were performed in triplicates and IC$_{50}$ values were estimated from the averaged response curves. For compounds with IC$_{50}$<100 µM, the MTT assay was repeated. The results are shown in Table 2, FIGS. 2a-2i, and FIG. 4.

TABLE 2

Cytotoxicity of rhein analogs compared to doxorubicin against three different cell lines.

| Compounds | IC$_{50}$ (µM) against HeLa | IC$_{50}$ (µM) against Hek | IC$_{50}$ (µM) against KB |
|---|---|---|---|
| Rhein | >100 | >100 | >100 |
| 5 | 4 | 4 | 4.5 |
| 6 | 40 | 8 | 15 |
| 7 | 10 | 2 | 9 |
| 12 | 1.3 | 1.9 | 5.2 |
| 13 | 8 | 2.3 | 38 |
| 14 | 2.5 | 1.4 | 10 |
| 17 | 16 | 8 | 19 |

TABLE 2-continued

Cytotoxicity of rhein analogs compared to doxorubicin against three different cell lines.

| Compounds | IC$_{50}$ (µM) against HeLa | IC$_{50}$ (µM) against Hek | IC$_{50}$ (µM) against KB |
|---|---|---|---|
| 18 | 3 | 1.4 | 4.8 |
| 21 | 14 | 8 | 21 |
| 22 | 7 | 2.2 | 9 |
| 23 | 5.8 | 4 | 8 |
| Doxorubicin | 1.5 | 0.15 | 0.4 |

The in vitro cytotoxicity studies of the synthesized compounds were performed in three different cell lines (HeLa, Hek, and KB). The activities of the herein described analogues were compared to that of rhein itself and doxorubicin. Due to the poor solubility of the compounds, all of the solutions used for biological testing were prepared using DMSO as solvent.

The cytotoxicity studies against HeLa cell line reveal that the compounds' activities are in the µM range and vary from IC$_{50}$=40 µM to IC$_{50}$=1.3 µM (Table 1). The least potent rhein analogue (6) (IC$_{50}$=40 µM) is 2.5 times more potent that rhein itself (IC50=100 µM). The most potent compound 12 (IC$_{50}$=1.3 µM) is about 100-fold more potent than rhein (IC50=100 µM) against the cervical cancer cell HeLa. Compound 12 (IC$_{50}$=1.3 µM) appears to have similar cytotoxicity against HeLa when compared with doxorubicin (IC$_{50}$=1.4 µM). All of the synthesized compounds showed significant improvement of the activity compared to rhein (Table 1).

With respect to Hek cell lines, all of the rhein analogues showed dramatically improved activity with IC$_{50}$ values in the single digit µM range (Table 1). The most potent compound against Hek cells is compound 18 (IC$_{50}$=1.4 µM).

The described rhein analogues were tested against a third cell line, KB. Once again all of the synthesized compounds showed great improvement in their activity compared to rhein. The most potent compound against this cell line is 18 (IC$_{50}$=4.8 µM). The least potent compound 13 (IC$_{50}$=38 µM) against the KB cells showed two and a half times increase in activity compared to rhein (IC$_{50}$=100 µM).

Rhein analogues 5, 12, 14, and 18 showed low micro molar IC$_{50}$ values against all three cell lines assayed (Table 1). Two of the compounds that exhibited the highest activities, compounds 12 and 14, have the two hydroxyl groups on the anthraquinone moiety protected by a methoxy group. The fact that the above-mentioned compounds have the lowest IC$_{50}$ values implies that the methoxy protection at positions 1 and 8 on the anthraquinone moiety plays a crucial role in the increased activity of these compounds. On the other hand, it has been reported that rhein analogues having the methoxy groups at positions 1 and 8 do not show any cytotoxicity against L1210 leukemic cells, which suggest that there might be other structural factors that result in the increased cytotoxicity.

Considering the fact that in previous studies the methoxy protected compounds did not show cytotoxic activity against carcinoma cells one can speculate that in fact the key factor for the improved activity is the addition of alkylating agent to position 3 of the polycyclic aromatic system. While the intercalating power of the 1,8-methoxy protected compounds might not be as good as that of the free 1,8-hydroxy compounds, interactions of the planar part of these molecules with the DNA base pairs can bring the alkylator in closer proximity to the highly nucleophilic DNA backbone.

Having the alkylating agent in close proximity to the DNA backbone or a nucleophilic group of a neighboring base can promote covalent interactions. Intercalation as well as covalent interactions with the DNA can cause conformational changes and even rupture of the DNA helix, which can induce apoptosis.

Two more important structural factors may play an important role: (1) the type of alkylator and (2) the length of the linker. In the case of 12 and 14, the alkylating agent is directly attached to the amine at position 3. Compounds 12 and 14 have shown great improvement in cytotoxycity compared to rhein. These compounds can be used as leads for future development because they carry the potential for further improvement of their activity. The use of a longer linker between the polycyclic aromatic system and the alkylating agent might have positive effects on the compounds' cytotoxicities. The three compounds that have a short linker at position 3 did not show high potency. On the contrary, some of them, 6, 7, and 13, have the highest $IC_{50}$ values in the in vitro studies (Table 1).

The type of leaving group on the alkylating agent may also play an important role in increasing the activity of the compounds. Initially a hypothesis was made based on the atomic size and the chemical properties of the leaving groups of the alkylating agents; compounds containing iodide and bromide should exhibit better activity than compounds containing chloride. Strong evidence supporting that hypothesis was not obtained from the performed studies. Two of the four most potent compounds contain chlorides as leaving groups after a potential alkylation reaction. One of them has iodide, and one has bromide. Clearly the most potent compound against all of the three cell lines studies is compound 12 that carries the combination of methoxy protected hydroxy groups and a chloride as leaving group after potential alkylation reaction. The attempt to increase solubility by the addition of a long linker containing ethylene glycol did not result in the expected increase of the biological activity.

In conclusion, eleven new rhein analogues have been synthesized by linking an alkylating agent to position 3 of the core structure. The synthesized analogues were tested in vitro by using the MTT assay against three different cell lines: HeLa, Hek, and KB. All of the compounds tested showed improved cytotoxicity compared to rhein with $IC_{50}$ values in the μM range against cancer cells. Four of the compounds, 5, 12, 14, and 18, showed significant improvement against HeLa cells. The improvement of cytotoxycity at such level is evidence that the combination between an intercalating moiety and an alkylating agent can be a successful strategy for designing DNA targeting anticancer drugs.

Figures 3A, 3B:
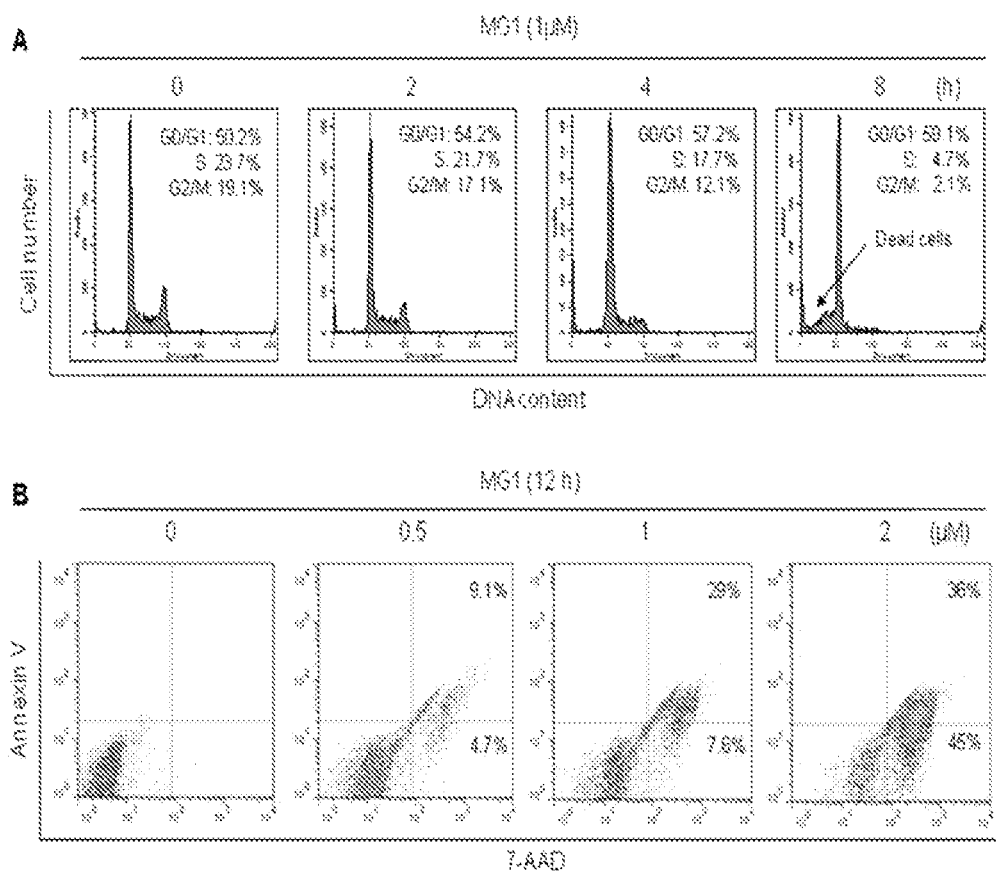
FIGS. 3a and 3b are graphs showing cell-cycle arrest (a) and apoptosis (b) of MG1-treated EU-1 cells were analyzed by flow cytometry.
Figure 4:
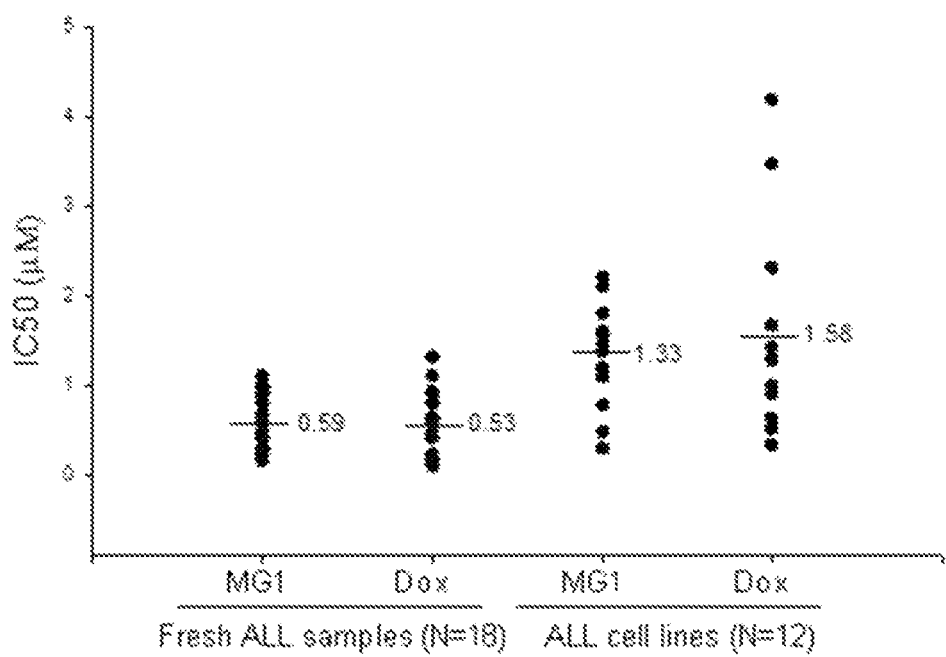
FIG. 4 is a graph showing the distribution of $IC_{50}$ values for MG1 and doxorubicin-treated primary ALL patient samples and ALL cell lines.

MG1 was selected for further investigation. The expression of p53 and its target p21 (for G1 cell cycle arrest) and PUMA (for apoptosis) as well as activation of caspase-3 and cleavage of death substrate PARD in EU-1 cells treated with different concentrations of MG1 over a period of 8 hours and as a function of a single concentration at different time points. Cell cycle arrest (A) and apoptosis (B) of MG1-treated EU-1 cells was analyzed by flow cytometry. The results are shown in FIGS. 3A and 3B. The mechanism of cancer cell death of MG1 compared to doxorubicin was also investigated. Comet images show that doxorubicin induces cancer cell death through DNA damage while MG1 induces cell apoptosis not through DNA damage (see FIG. 4).

Figures 5A, 5B:
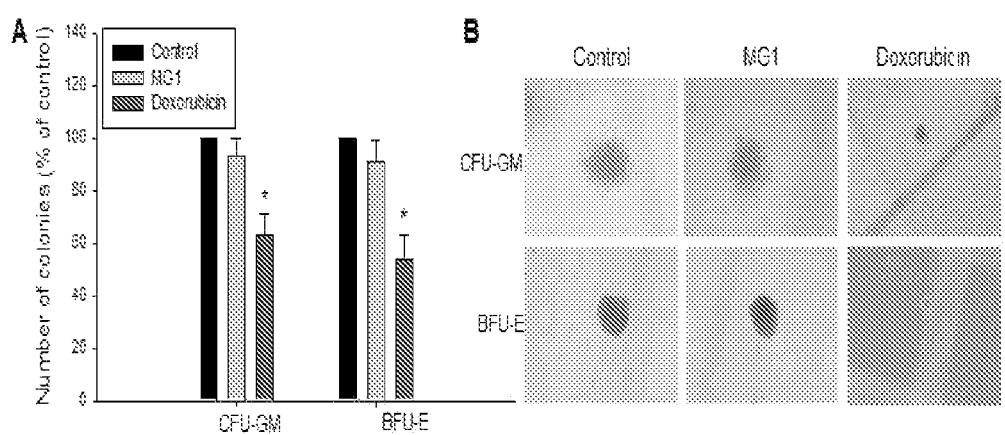
FIGS. 5a and 5b are graphs comparing the inhibitory effects of MG1 and doxorubicin on the CFU-GM and BFU-E of normal human BM as assessed by in vitro colony formation analysis.

The compounds described herein exhibited less toxicity compared to doxorubicin. FIG. 5 shows the effects of MG1 and doxorubicin on CFU-GM and BFU-E of normal human bone marrow. The effect of MG1 was much closer to the control (no drug) than doxorubicin indicating substantially less toxicity to human bone marrow. Toxicity was also evaluated in mice. The treatments doses and observations are shown in FIG. 6. 15 mg Doxorubicin administered in a single injection at a dose of 15/kg resulted in the death of all mice at day 7 due to cardiac toxicity. In contrast, mice administered MG1 at a dose of 100 mg/kg/day, three times a day, were alive after 9 days. Subsequently, a single injection of MG1 at a dose of 400 mg/kg was administered via injection. None of the mice died after this injection.

Figure 7:
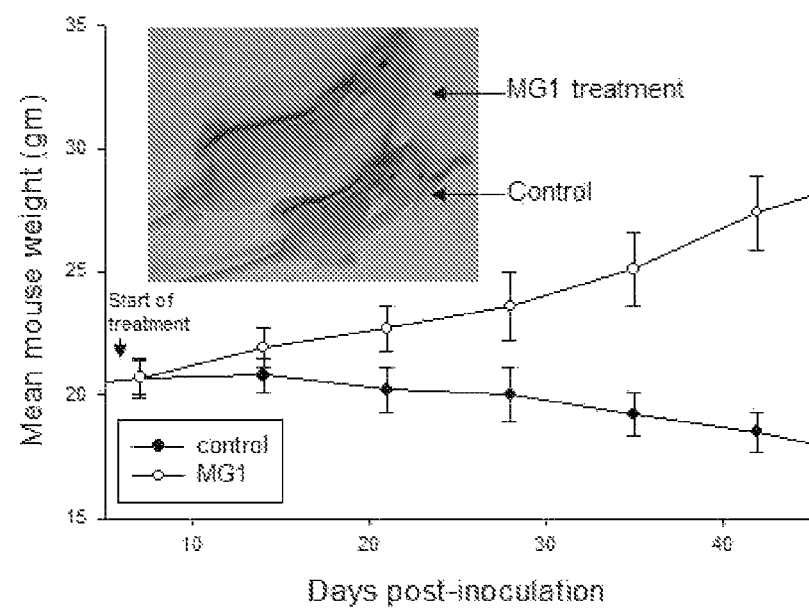
FIG. 7 is a graph showing the weight of SCID mice inoculated with EU-1 leukemia cells in the presence or absence (control) of MG1treatment. Insert: size comparison of representative mouse from each group at 49 days post-treatment. Weight gains were observed in MG1-treated mice and weight loss in control group (without MG1 treatment).

The effect of MG1 versus a control (no drug) was evaluated in mice inoculated with EU-1 leukemia cells. The results are shown in FIG. 7.

Additional compounds 9a-d, shown above, and the compounds in Table 1 were prepared and their cytotoxicities were evaluated. The date is shown below in Tables 3 and 4.

TABLE 3

Cytotoxicity evaluation of series 2 rhein analogues

| Compounds | $IC_{50}$ (μM) against HeLa | $IC_{50}$ (μM) against MOLT4 |
|---|---|---|
| Rhein | >100 | 37 |
| 7 | 17 | 10 |
| 8 | 2.7 | 0.6 |
| 9a | 6.1 | 3.0 |
| 9b | 5.8 | 3.1 |
| 9c | 13[a] | 25 |
| 9d | 33 | 4.1 |
| Doxorubicin | 0.98 | 0.04 |

[a]$R^2$ < 0.8 for non-linear regression in sigmoidal model fitting.

TABLE 4

Cytotoxicity evaluation of Series 1 rhein analogues using the MTT assay

| Compounds | $IC_{50}$ (μM) against HeLa | $IC_{50}$ (μM) against MOLT4 |
|---|---|---|
| Rhein | >100 | 37 |
| 24a | 3.4 | 1.4 |
| 26a | 16 | 14 |
| 26b | >100 (36)[a][b] | >100 (37)[a][b] |
| 26c | 68 | >100 |
| 26d | >100 | 35 |
| 26e | >100 | 22 |
| 26f | >100 (20)[a][b] | 29[b] |
| 26g | 9.9 | 21[b] |

[a]The actual $IC_{50}$ should be higher than 100 μM since less than 50% cells were killed even at the highest concentration. The values inside parenthesis were calculated by Prism 4 using sigmoidal curve fitting.,
[b]$R^2$ < 0.8 for non-linear regression in sigmoidal model fitting.

Figures 8A, 8B:
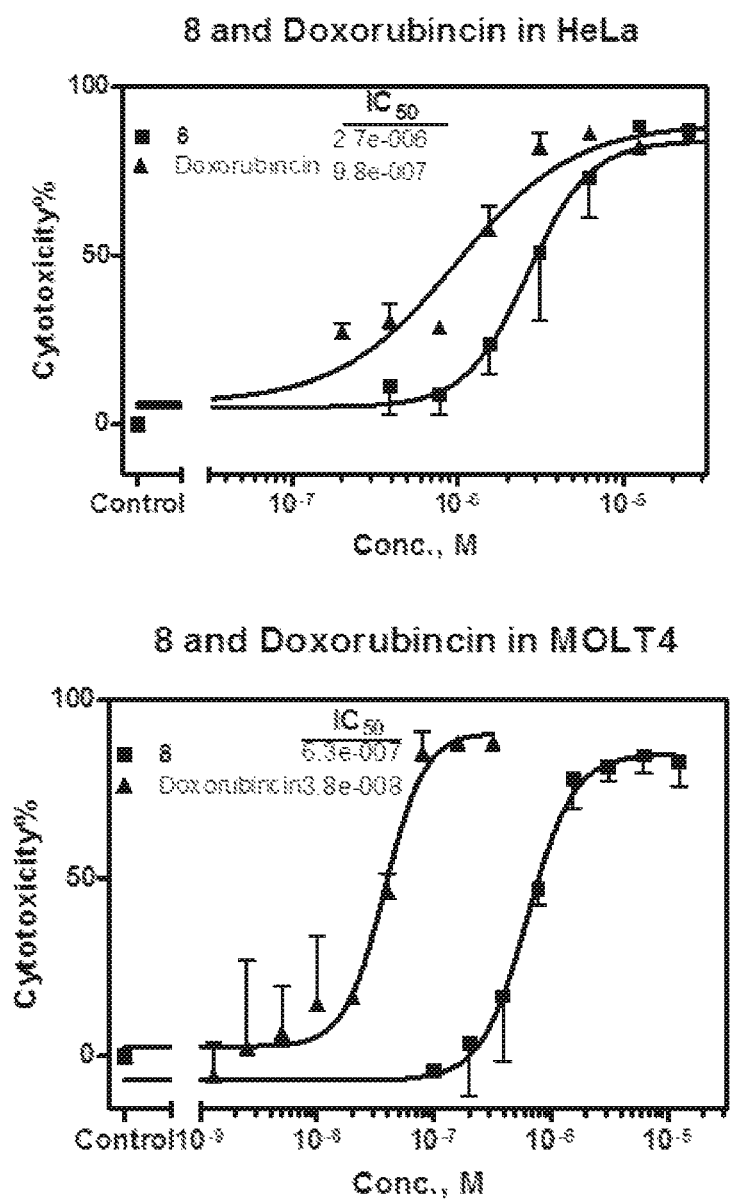
FIGS. 8a and 8b are graphs showing the percent toxicity as a function of concentration of compound 8 against HeLa cells (FIG. 8a) and MOLT4 cells (FIG. 8b).

With respect to the compounds in Table 3, compound 8 showed the best activity (Table 3). The $IC_{50}$ of 8 against HeLa approaches that of the positive control, doxorubicin, and 8 is the only compound among all the analogues having submicromolar $IC_{50}$ against the MOLT4 cell line. The potent activity of 8 may be due to its unique structural feature of combining an alkylating agent with an intercalation moiety. Besides 8, compound 7 also showed higher potency than most compounds in Table 4 except 4a. These observations suggest that the amine/amide modification have an improved chance of success than aryl derivertization at the 3-position. Previous reports by others suggest that the ring structure side chains are not critical for high cytotoxicity of these anthraquinone compounds and the dicationic side chain gave better activity than the monocationic ones. A comparison of the cytotoxicity of compound 8 compared to doxorubicin against HeLa and MOLT4 cells in shown in FIGS. 8a and 8b.

In the second series, it was found that 9b showed better activity than 9c and 9d, but similar activity as 9a. Compared with mitoxanthrone, 9b shared similar structural features but having a cyclic instead of a linear diaminoalkyl side chain.

Figure 9A:
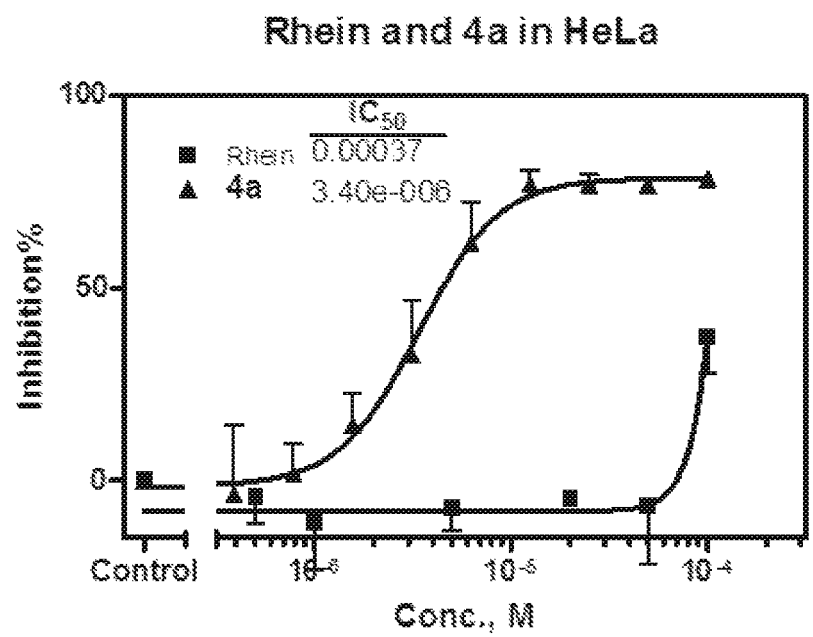
FIGS. 9a and 9b are graphs showing the percent toxicity as a function of concentration of compound 4a against HeLa cells (FIG. 9a) and MOLT4 cells (FIG. 9b).
Figure 9B:
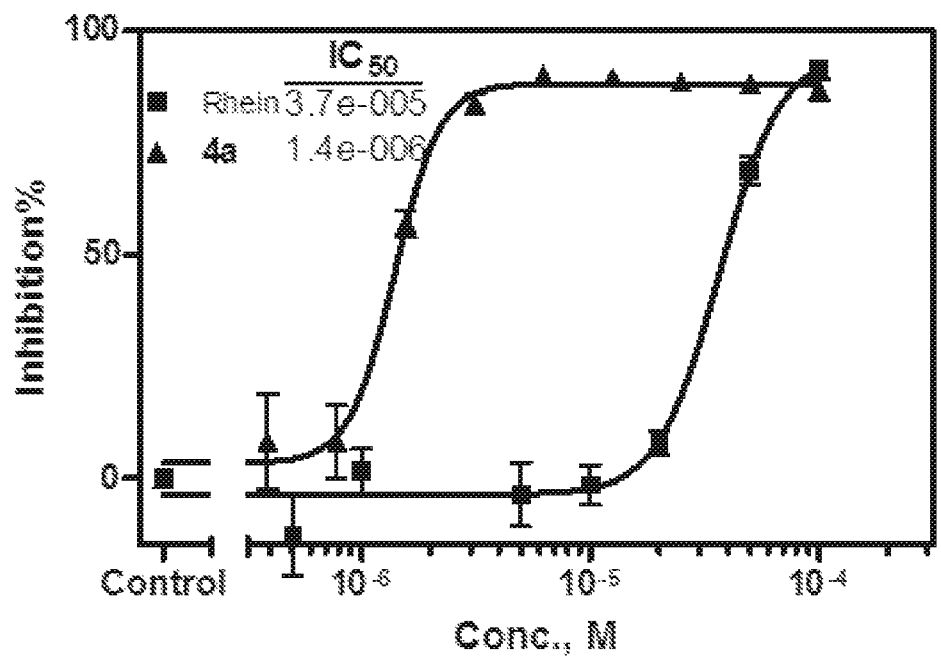

With respect to the compounds in Table 4, the in vitro cytotoxicity tests showed that the most potent compound 24a has an $IC_{50}$ at the single digit µM level against both HeLa and MOLT4 cell lines (Table 4). Compared with rhein, the potency increased by at least 30-fold in both cancer cell lines after the introduction of a phenylthio group at the 3-position. Analogues 6b and 6c showed decreased cytotoxicity against MOLT4 compared with rhein. In HeLa cells, 6a, 6c and 6g showed moderate improvement in potency. In general, for this series of analogues, directly attaching an aromatic ring to the anthraquinone at the 3-position did not significant increase potency. This may result because the planar structure of anthraquinone is compromised by the steric strain around the biaryl C—C bond, leading to decreased DNA intercalation properties. Spacing the aromatic ring away from anthraquinone by one atom such as sulfur, appeared to alleviate this strain and increased potency. A comparison of the cytotoxicity of compound 24a compared to doxorubicin against HeLa and MOLT4 cells in shown in FIGS. 9a and 9b.

Example 4. Synthesis of Additional Rhein Analogs

As described in the literature, a number of Rhein analogues have been synthesized and tested against a variety of cancer cell lines. Although some of the compounds showed potency, there exists a need for compounds with improved solubility. In order to improve the solubility of the flat anthraquinone rhein analogues, longer side chains at positions 1 and 8 of the core Rhein structure were introduced. The introduction of long alkyl chains at these positions disrupts the pi-pi stacking of the flat polycyclic aromatic systems and improves solubility. This was observed experimentally.

In addition to the modifications to the 1 and 8-hydroxyl positions, a number of alterations were made to position 3 of the core Rhein structure. Specifically, analogs lacking a highly reactive alkylating moiety were prepared. Highly reactive alkylating moieties can interact with any nucleophile present in a biological system, includes targets not intended for reaction. There are number of nucleophilic agents, such as amino acids, present and available to interact with electrophilic compounds containing good leaving groups, such as halogens. The general presence of active halogens in drug candidates is undesirable as it not only reduces bioavailability, but also increases the chance for nonspecific/unintended interactions.

The strategy that was employed in the design of the below-described compounds relies on the addition of other less reactive functional groups that will not be able to undergo alkylation reactions and yet exhibit the general activity and low toxicity of previously synthesized Rhein analogues. The synthesized compounds have been grouped into eight major groups based on the modifications made to the 1 and 8 positions of the core anthraquinone structure; compounds containing methyl, ethyl, propyl, benzyl, allyl, azido-alkyl, isopropyl, and isobutyl functional groups protecting the 1 and 8-hydroxyl positions (FIGS. 10-17).

The synthetic strategy for preparing the compounds of FIGS. 10-17 involves four steps. Seven of the synthetic routes (Schemes 2-6, 8, and 9 shown above) utilize a similar strategy with slight variations. The aniline compounds synthesized through each of the four step routes were used as a building blocks for the final products tested against a number of cancer cell lines. The first step of each of these five routes involves protection through alkylation of the 1- and 8-hydroxyl groups and formation of an ester at position 3 through reaction with methyl iodide, 1-bromoethane, 1-bromopropane, benzyl chloride, allyl bromide, 1-bromo-2-methyl propane, and 1-bromo-3-methyl butane to give compounds 2, 6, 10, 14, 18, 27, and 31 respectively in 63% to quantitative yields. Sodium iodide was added in order to improve the alkylation efficiency and the base used was potassium carbonate (Scheme 2-6, 8 and 9).

The second step of the designed routes was hydrolysis using sodium hydroxide in water/ethanol mixture. The reaction mixtures were heated to 50° C.-70° C. and stirred for 2 hours. Desired carboxylic acids 3, 7, 11, 15, 19, 28 and 32 were collected upon filtration of the precipitate formed after cooling and acidification of the reaction mixtures respectively. The yields obtained range from 89% to quantitative yield (Scheme 2-6, 8, and 9). Acids 3, 7, 11, 15, 19, 28, 32 were then reacted with diphenyphosphoryl azide (DPPA) at room temperature in the presence of triethyl amine (TEA). The reaction mixtures were suspended in ice water and the yellow/brown precipitates formed were isolated as the acyl azides 4, 8, 12, 16, 20, 29, 33 (Scheme 2-6, 8, and 9). The acyl azides undergo Curtis rearrangement in the fourth step, giving a 1,8-hydroxy protected anilines 5, 9, 13, 17, 21, 30, 34 respectively (Scheme 2-6, 8, and 9).

Figure 10:
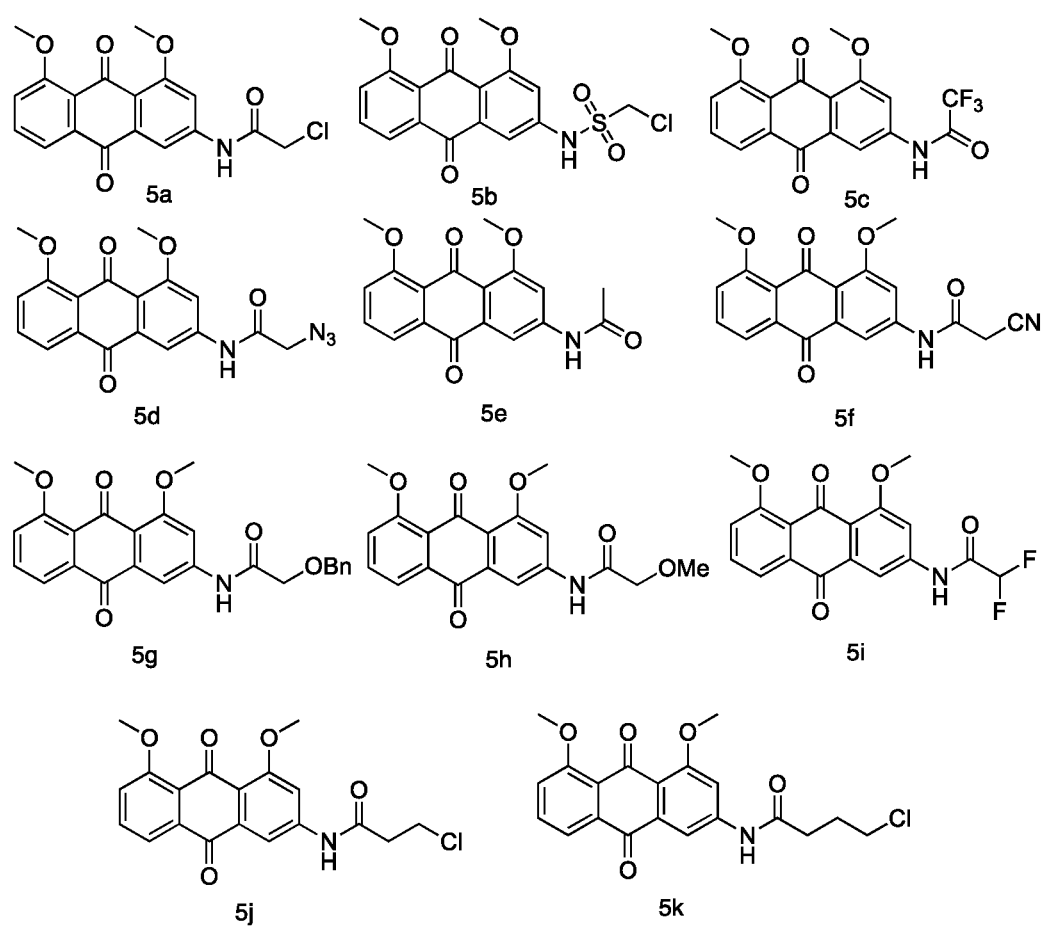
FIGS. 10-17 are examples of Rhein analogs functionalized at the $R_1$, $R_8$, and/or $R_3$ positions.
Figure 11:
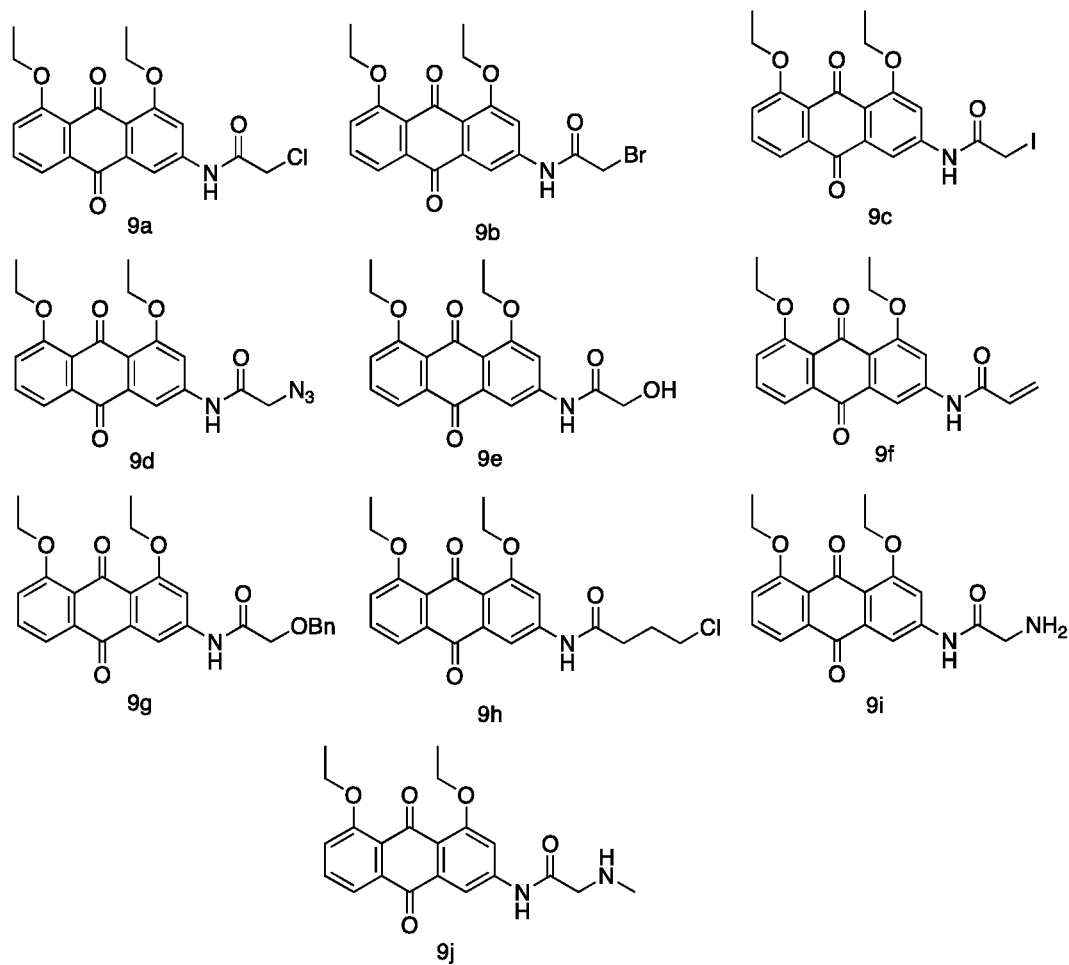
Figure 12:
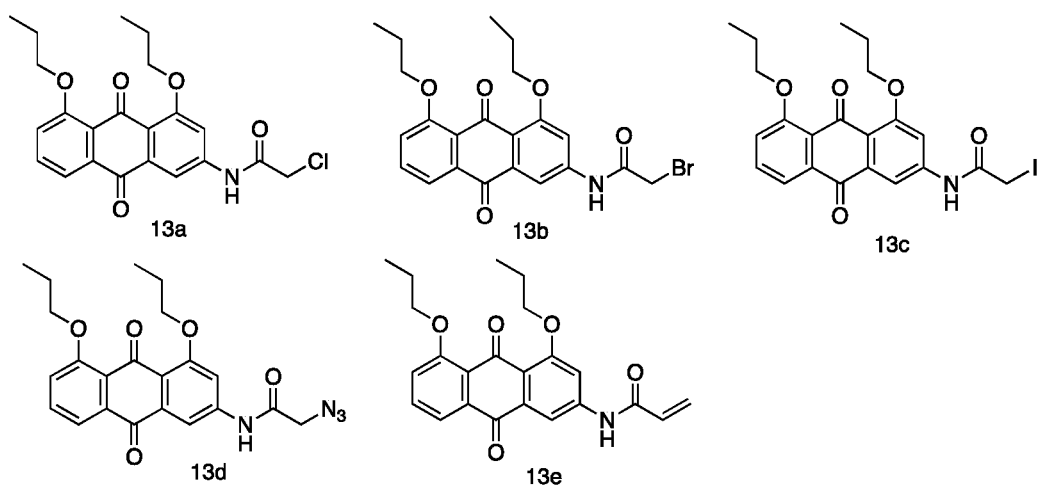
Figure 13:
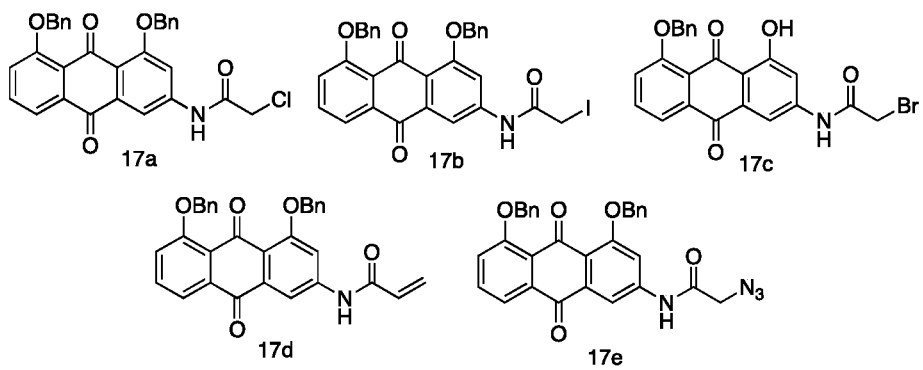
Figure 14:
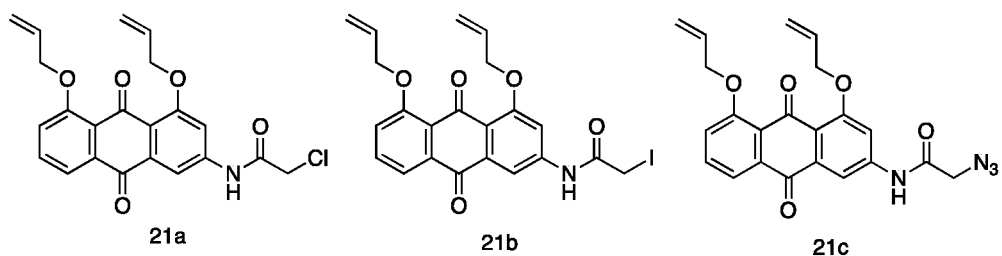

Aniline 5 was used as a building block for five rhein analogues 5a, 5b, 5c, 5d, and 5e (FIG. 10). Aniline 5 was reacted with chloroacetyl chloride in dioxane to yield the desired compound 5a with a 30% yield. Compound 5a was then reacted with sodium azide in acetone to give compound 5d in quantitative yield. Compound 5b was synthesized in 92% yield through the reaction of compound 5 with chloromethanesulfonyl chloride in the presence of pyridine at room temperature and overnight stirring. Compound 5b is very different from any other compounds that belong to this group because it does not have the common amide structural feature, but rather a sulfonamide linking the anthraquinone core to the alkylating group. The reaction of trifluoroacetic anhydride (TFAA) with aniline 5 in the presence of TEA resulted in the formation of amide 5c in 90% yield. Amide 5e was obtained through the reaction of 5 with acetyl chloride in the presence of TEA with a yield of 70% (FIG. 10).

Compounds 9a-9b were synthesized by addition elimination reactions of aniline 9 with chloroacetyl chloride and bromoacetyl bromide respectively. No addition of base was necessary and the desired 9a and 9b were obtained in 50% yield. Reacting 9a with sodium iodide in acetone resulted in the formation of 9c in quantitative yield. Similar strategy was used in the synthesis of 9d, which was obtained in quantitative yield after reaction of 9a with sodium azide in acetone at room temperature. Alcohol 9e was synthesized by stirring compound 9b in sodium hydroxide solution in water/ethanol mixture; the yield observed was 20%. Compound 9f, was synthesized through addition elimination reaction between acryloyl chloride and compound 9, 97% yield was observed. Compounds 9g and 9h were synthesized by a using similar reaction by reacting aniline 9 with benzoxyacetyl chloride and 4-chlorobutyryl chloride respectively; compound 9g was obtained in 50% yield and compound 9h was obtained in 30% yield. Hydrogenation reaction of 9d with hydrogen gas in the presence of catalytic amounts of palladium on activated carbon gave compound 9i in 92% yield. The synthesis of compound 9j involved a substitution reaction between compound 9a and methylamine (aqueous solution), 9j was isolated with 20% yield.

Compounds 13a, 13b, and 13e were obtained through addition elimination reactions of aniline 13 with chloroacetyl chloride, bomoacetyl bromide, and acryloyl chloride, respectively. No addition of base was necessary and the yields obtained were 62%, 20%, and 26% respectively.

Compounds 13c and 13d were synthesized by reacting amide 13a with sodium iodide and sodium azide. The yields obtained for 13c and 13d were 82% and 50% respectively.

Compounds 17a, 17c, and 17d were synthesized via the reaction of aniline 17 and chloroacetyl chloride, bromoacetyl bromide, and acryloyl chloride without the addition of base. The deprotection of the benzyl group at position 1 was observed as the only identified product by the addition elimination reaction between 17 and bromoacetyl bromide. Compound 17c was obtained in 31% yield; compounds 17a and 17d were obtained in 60% and 77% respectively. Compound 17b was synthesized after the reaction of 17a with sodium iodide and compound 17e was obtained after reaction of 17a with sodium azide; both products were isolated in quantitative yield.

One compound derived directly from 21 has been synthesized (21a) (FIG. 14) and two compounds were developed via substitution reaction of 21a with sodium azide and sodium iodide respectively. The substitution reactions gave compound 21b and 21c in quantitative yield. Compounds 21a was synthesized through addition elimination reaction between 21 and chloroacetyl chloride giving the desired product in 73% yield. Compounds 18 to 21 (21a, 21b, 21c) have been tested against number of cancer cells and the results are described below. All of the compounds containing an allyl group protecting the 1,8-hydroxyl positions of the anthraquinone building block have extremely poor water solubility therefore further analogues in this class have not been synthesized.

The compounds described herein were separated into eight major groups based on the substituents attached to the 1 and 8 hydroxyl positions on the core Rhein structure. The synthesis of five of these groups of compounds is described above. Scheme 6 shows the synthesis of the aniline (26) used as core structure for the development of the sixth group of Rhein analogues.

Figure 15:
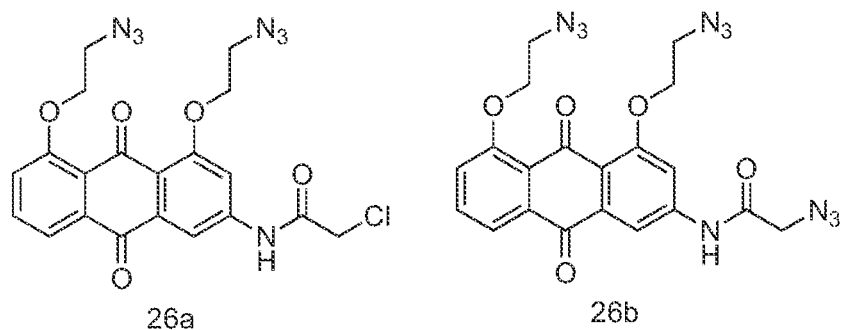

The synthesis of compound 26 involves selective methylation with Rhein (1) and formation of ester 22 utilizing iodomethane and sodium bicarbonate. Compound 22 was obtained in 93% yield and used as a starting material for the next step, which involved the alkylation of hydroxyl positions 1 and 8 with 2-azidoethyl 4-methylbenzenesulfonate in the presence of cesium carbonate. The fully alkylated compound 23 was obtained in 83% yield. The next step of the synthetic route was to hydrolyze the methyl ester at position 3 using sodium hydroxide in water/ethanol mixture. The hydrolysis gave compound 24 in nearly quantitative yield. The last two steps of the synthetic route towards the core compound 26 were similar to what was previously described in this paper. The formation of acyl azide 25 was achieved by reaction of acid 24 with DPPA in the presence of TEA in 75% yield. The final step towards 26 was Curtis rearrangement reaction in dioxane and sodium hydroxide solution. Aniline 26 was isolated in 83% yield and used for the synthesis of the sixth group of rhein analogues tested against number cancer cell lines (FIG. 15).

Compound 26a was synthesized in familiar fashion, by reacting aniline 26 with chloroacetyl chloride in the absence of organic or inorganic base. Amide 26a was obtained in 83% yield and used for the synthesis of azide 26b. Compound 26a was reacted with sodium azide at room temperature giving 26b in quantitative yield.

Figure 16:
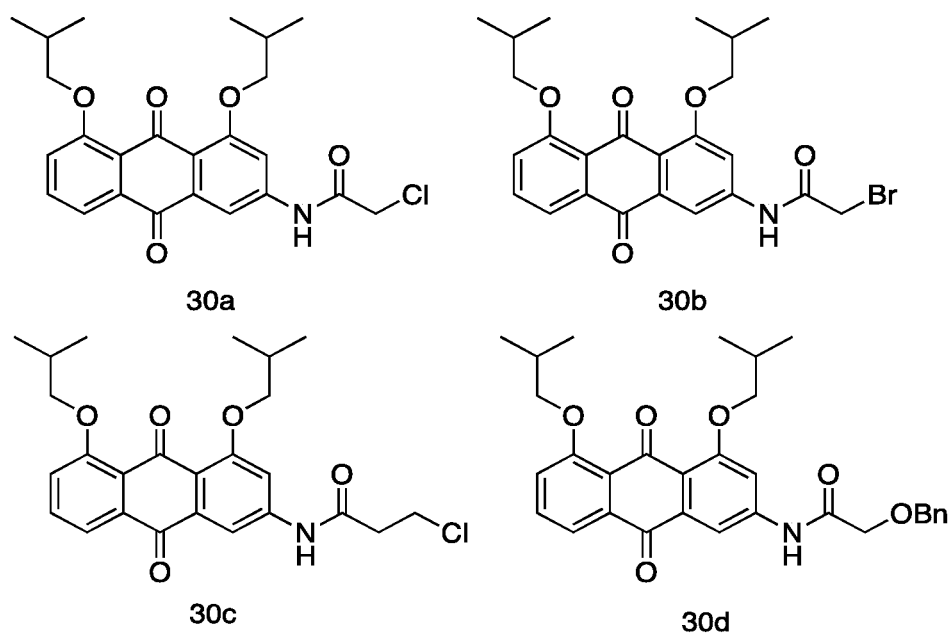
Figure 17:
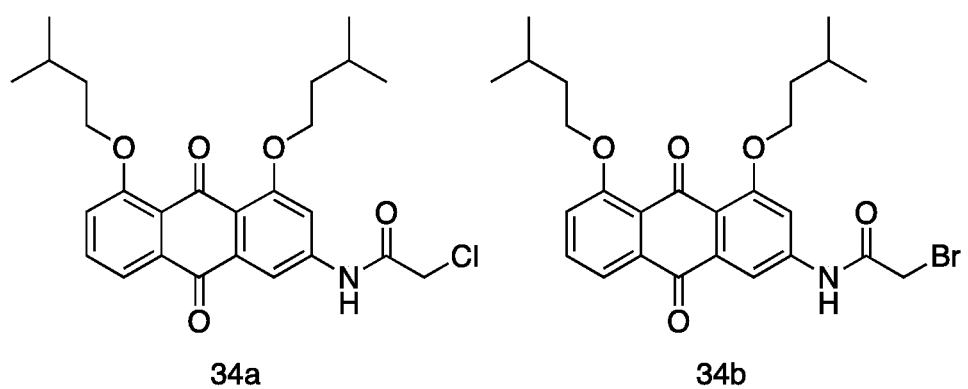

The two classes of compounds described next introduce branched alkyl chains to the 1,8 positions of the anthraquinone. The reasoning behind this is that the branched chains may improve solubility by disrupting the pi-pi stacking of the aromatic polycyclic system in solution. The branched chains as described below have significantly different structures compared to previously disclosed Rhein analogues and provide basis for structure activity relationship studies (FIGS. 16 and 17). The synthetic approach towards the aniline building blocks for the two classes of compounds containing branched chains is very similar to the synthesis of the first 5 classes of compounds herein described (Schemes 7 and 8).

Four compounds containing isopropyl groups protecting the 1- and 8-hydroxyl positions we synthesized form aniline 30. Compounds 30a, 30b, 30c, and 30d were synthesized in similar fashion via addition elimination reaction between the aniline and chloroacetyl chloride, bromoacetyl bromide, 3-chlorobutyryl chloride, and benzoxyacetyl chloride respectively. Full conversion of the starting material to product was observed, however exact yield was not reported, because crude starting material was used for the reactions.

Two compounds containing isobutyl groups on the 1- and 8-hydroxyl positions have been synthesized and tested for biological activity. Compounds 34a and 34b were synthesized by reacting aniline 34 with chloroacetyl chloride and bromoacetyl bromide respectively. Full conversion of the starting material to product was observed, however exact yield was not reported, because crude starting material was used for the reactions.

The final group of compounds herein discussed was synthesized by utilizing previously reported rhein analogues, or other anthraquinones such as aloe emodin (Scheme 7). Even though the structures of these compounds are not similar to each other they are separated into a unique group based on the synthetic approach and reasoning behind their development. For example compound 36, 42, 44, and 46 do not have the typical amide structural feature common to many of the compounds described herein; the former three compounds also do not have the 1- and 8-hydroxyl positions protected. Compound 46 has the 1 and 8 positions protected with a methyl groups, however, it is lacking of an amide bond at position 3. Compound 39 on the other hand possesses an amide bond, but is lacking substituents at positions 1 and 8. These compounds were designed to generally probe the activity of the rhein analogues when important structural features are being absent.

Example 5. Biological Activity of Rhein Analogs

All of the compounds synthesized were tested against a number of cancer cell lines: Hela KB, Cos7, Molt4, K562, EU1, and T98G. The cancer cell lines vary from leukemia cell lines (Molt4, EU, K562) to solid-state tumor cell lines (Hela, KB, Cos7) and the drug resistant cell lines (T98G). The data obtained is shown in the tables below.

TABLE 5

| Cytotoxicity of compounds containing methyl ester groups at positions 1 and 8. | | | | | | | | |
|---|---|---|---|---|---|---|---|---|
| Compound ID | Compound # | Hela | KB | Cos7 | T98G | Molt4 | K562 | EU1 |
| BW-AQ-145 | 5 | >50 | >50 | >50 | >50 | >25 | >25 | >25 |
| BW-AQ-112 | 5a | 3.3 ± 1.2 | 4.3 ± 0.71 | 1.2 ± 0.08 | 2-12.5 | 0.137 ± 0.053 | 0.79 ± 0.26 | ND |
| BW-AQ-138 | 5b | >50 | >50 | >50 | >50 | >1.6 | >6.25 | ND |
| BW-AQ-132 | 5c | >50 | >50 | >50 | >12.5 | >1.6 | >6.25 | ND |

TABLE 5-continued

Cytotoxicity of compounds containing methyl ester groups at positions 1 and 8.

| Compound ID | Compound # | Hela | KB | Cos7 | T98G | Molt4 | K562 | EU1 |
|---|---|---|---|---|---|---|---|---|
| BW-AQ-137 | 5d | 24.6 | 23.6 | >50 | >50 | >1.6 | >6.25 | ND |
| BW-AQ-134 | 5e | >50 | >50 | >50 | >50 | >1.6 | >6.25 | ND |
| BW-AQ-172 | 5f | >50 | <6.25 | ND | >50 | >25 | >25 | >25 |
| BW-AQ-175 | 5g | >50 | 33.6 | ND | >50 | 25 | >25 | 20.5 |
| BW-AQ-170 | 5h | >50 | >50 | ND | >50 | >25 | >25 | >25 |
| BW-AQ-171 | 5i | >50 | 50 | ND | >50 | >25 | >25 | >25 |
| BW-AQ-173 | 5j | 50 | 50 | ND | >50 | >25 | >25 | 25 |
| BW-AQ-174 | 5k | >50 | >50 | ND | >50 | >25 | >25 | >25 |

All $IC_{50}$ values reported in the μM range;
ND = Not Determined

TABLE 6

Cytotoxicity of compounds containing ethyl ester groups at positions 1 and 8.

| Compound ID | Compound # | Hela | KB | Cos7 | T98G | Molt4 | K562 | EU1 |
|---|---|---|---|---|---|---|---|---|
| BW-AQ-113 | 9a | 2.1 ± 0.5 | 5.5 ± 3.2 | 1.1 ± 0.15 | 5.2 ± 0.36 | 0.122 ± 0.050 | 0.74 ± 0.18 | ND |
| BW-AQ-114 | 9b | 3.9 ± 1.0 | 10.2 ± 2.26 | 2.0 ± 0.6 | >12.5 | 0.284 ± 0.021 | 0.84 ± 0.36 | ND |
| BW-AQ-115 | 9c | 3.9 ± 1.2 | 6.6 ± 1 | .6 ± 0.33 | 10.4 ± 1.2 | 0.180 ± 0.077 | 0.83 ± 0.31 | ND |
| BW-AQ-159 | 9d | <6.25 | <6.25 | 23.4 | 35.7 | 12.5-25 | 11.8 | 15.9 |
| BW-AQ-157 | 9e | 6.35 | 9.5 | 5 | 15.4 | 0.42 | 1.8 | 0.358 |
| BW-AQ-158 | 9f | 19.7 | 20.3 | 8.42 | 21 | <3.2 | 10.7 | 6 |
| BW-AQ-182 | 9g | 47.3 | >50 | ND | >50 | 16.8 | >25 | 16.8 |
| BW-AQ-179 | 9h | 6.25 | <6.25 | ND | 50 | 15.3 | 10.7 | 17.6 |
| BW-AQ-166 | 9i | 11 | 18.8 | 50 | 37.3 | >25 | >25 | >25 |
| BW-AQ-167 | 9j | 0.753 | 1.54 | 5.51 | 11.2 | 21.5 | 2.05 | 13.6 |

All $IC_{50}$ values reported in the μM range;
ND = Not Determined

TABLE 7

Cytotoxicity of compounds containing propyl ester groups at positions 1 and 8.

| Compound ID | Compound # | Hela | KB | Cos7 | T98G | Molt4 | K562 | EU1 |
|---|---|---|---|---|---|---|---|---|
| BW-AQ-147 | 10 | >50 | >50 | 50 | >50 | >25 | >25 | >25 |
| BW-AQ-116 | 13a | 2.5 ± 0.2 | 6.6 ± 0.6 | 1.2 ± 0.25 | 8 | 0.119 ± 0.024 | 1.1 ± 0.32 | ND |
| BW-AQ-117 | 13b | 2.5 ± 1.2 | 8.5 ± 0.64 | 2.1 ± 0.4 | 12.5 | 0.164 ± 0.052 | 1.6 ± 1.1 | ND |
| BW-AQ-118 | 13c | 3.4 ± 0.2 | 11.6 ± 4.6 | 1.8 ± 0.4 | 14.5 ± 3.9 | 0.138 ± 0.010 | 1.3 ± 0.6 | ND |
| BW-AQ-156 | 13d | 1.54 | 3 | 3 | 17.8 | 0.492 | 2.8 | 1.09 |
| BW-AQ-160 | 13e | 14.8 | 16.2 | 8.12 | 25 | 3.99 | 6.93 | 4.84 |

All $IC_{50}$ values reported in the μM range;
ND = Not Determined

TABLE 8

Cytotoxicity of compounds containing benzyl ester groups at positions 1 and 8

| Compound ID | Compound # | Hela | KB | Cos7 | T98G | Molt4 | K562 | EU1 |
|---|---|---|---|---|---|---|---|---|
| BW-AQ-148 | 14 | 18.6 | >50 | >50 | >50 | >25 | >25 | >25 |
| BW-AQ-151 | 15 | >50 | 38.4 | 50 | >50 | >25 | >25 | >25 |
| BW-AQ-149 | 16 | >50 | >50 | >50 | >50 | >25 | >25 | >25 |
| BW-AQ-150 | 17 | ~50 | >50 | 17 | >50 | >25 | >25 | >25 |
| BW-AQ-126 | 17a | 6.1 ± 1.2 | 9 ± 3.7 | 2.5 ± 0.25 | >12.5 | 0.237 ± 0.105 | 3.3 ± 1.14 | 1.072 ± 0.262 |
| BW-AQ-129 | 17b | >50 | >50 | >50 | >12.5 | 1.6 | >6.25 | ND |
| BW-AQ-127 | 17c | 5.6 ± 0.63 | 5.4 ± 2.5 | 1.7 ± 0.43 | 13.8 ± 2.5 | 0.028 ± 0.006 | 1.95 ± 0.58 | 0.084 ± 0.058 |
| BW-AQ-128 | 17d | 8.6 ± 0.22 | 5.7 ± 2.1 | 5.5 ± 0.24 | 9.8 ± 0.2 | 0.981 ± 0.508 | >6.25 | >1.6 |
| BW-AQ-162 | 17e | 1.59 | 0.59 | 10.88 | 25.5 | >25 | >20 | 18.3 |

All $IC_{50}$ values reported in the μM range;
ND = Not Determined

TABLE 9

Cytotoxicity of compounds containing allyl ester groups at positions 1 and 8.

| Compound ID | Compound # | Hela | KB | Cos7 | T98G | Molt4 | K562 | EU1 |
|---|---|---|---|---|---|---|---|---|
| BW-AQ-152 | 18 | 27.6 | 22.5 | 12.5 | 29.3 | >25 | >25 | >25 |
| BW-AQ-153 | 19 | >50 | >50 | >50 | >50 | >25 | >25 | >25 |
| BW-AQ-154 | 20 | 24.3 | >50 | 19.4 | >50 | 6.66 | 19.5 | 3 |
| BW-AQ-155 | 21 | ~50 | 12.5 | >50 | >50 | >25 | >25 | >25 |
| BW-AQ-161 | 21a | >20 | >20 | >20 | >50 | >10 | >10 | >10 |
| BW-AQ-163 | 21b | >50 | 14.7 | >50 | >50 | >25 | >25 | >25 |
| BW-AQ-164 | 21c | >50 | >50 | >50 | >50 | >25 | >25 | >25 |

All IC$_{50}$ values reported in the μM range;
ND = Not Determined

TABLE 10

Cytotoxicity of compounds containing alkyl-azide ester groups at positions 1 and 8.

| Compound ID | Compound # | Hela | KB | Cos7 | T98G | Molt4 | K562 | EU1 |
|---|---|---|---|---|---|---|---|---|
| BW-AQ-120 | 23 | >12.5 | >50 | ~50 | >12.5 | >1.6 | >6.25 | ND |
| BW-AQ-121 | 24 | >12.5 | >50 | >50 | >12.5 | >1.6 | >6.25 | ND |
| BW-AQ-122 | 25 | >12.5 | >50 | >50 | >12.5 | >1.6 | >6.25 | ND |
| BW-AQ-123 | 26 | >50 | 20.5 | 50 | >12.5 | >1.6 | >6.25 | ND |
| BW-AQ-124 | 26a | 2.42 ± 0.6 | 3.6 ± 0.92 | 0.85 ± 0.27 | 4.8 | 0.077 ± 0.033 | 1.05 ± 0.33 | 0.283 ± 0.046 |
| BW-AQ-140 | 26b | 3.1 ± 0.68 | 3.4 ± 1.02 | 2.2 ± 0.41 | 13.8 ± 4. | 0.209 ± 0.044 | 3.2 ± 1.5 | 0.69 ± 0.152 |

All IC$_{50}$ values reported in the μM range;
ND = Not Determined

TABLE 11

Cytotoxicity of compounds containing isopropyl ester groups at positions 1 and 8.

| Compound ID | Compound # | Hela | KB | Cos7 | T98G | Molt4 | K562 | EU1 |
|---|---|---|---|---|---|---|---|---|
| BW-AQ-177 | 30a | <6.25 | <6.25 | ND | <12.5 | <0.2 | 2.81 | 0.522 |
| BW-AQ-183 | 30b | <6.25 | <6.25 | ND | <6.25 | 0.61 | 3.84 | 1.29 |
| BW-AQ-176 | 30c | <6.25 | <6.25 | ND | 10.5 | 8.02 | ND | 17.7 |
| BW-AQ-178 | 30d | >50 | >50 | ND | >50 | >25 | >25 | >25 |

All IC$_{50}$ values reported in the μM range;
ND = Not Determined

TABLE 12

Cytotoxicity of compounds containing isobutyl ester groups at positions 1 and 8.

| Compound ID | Compound # | Hela | KB | Cos7 | T98G | Molt4 | K562 | EU1 |
|---|---|---|---|---|---|---|---|---|
| BW-AQ-181 | 34a | <6.25 | <6.25 | ND | >50 | <0.2 | >25 | 0.70 |
| BW-AQ-180 | 34b | <6.25 | <6.25 | ND | 10.7 | 0.49 | 7.30 | 0.68 |

All IC$_{50}$ values reported in the μM range;
ND = Not Determined

Most of the compounds tested show a great potential against leukemia cell lines. One of the compounds exhibited an IC$_{50}$ value of about 30 nm against Molt4 leukemia cell line (Table 8). Another compound containing the alkyl-azido functionality at position 1 and 8 of the core structure, and an azide group at position 3 shows activity with IC$_{50}$ below 100 nm in two cell lines (Table 10). One can easily see that each group of compounds described above has a member that carries activity with IC$_{50}$ in the low or mid nanomolar range for at least one of the tested cell lines. For example one of the most active compounds having IC$_{50}$ value of 28 nM (17c) has benzyl groups at the 1 and 8 positions and an iodo at the amide position 3. These structural features permit for modifications that can further improve the activity. Possible modifications at halogen position consist of replacement of the halogen with an azido or an alcohol group. The benzyl groups can be substituted with other aromatic systems and potentially improve activity. More analogues following the mentioned structural changes are currently being synthesized.

We claim:
1. A compound having formula:

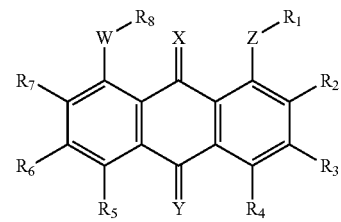

wherein
X and Y are independently O or S;
W and Z are independently O or S;
R$_1$ and R$_8$ are independently substituted or unsubstituted C$_1$-C$_{30}$ alkyl, substituted or unsubstituted C$_2$-C$_{30}$ alkenyl, substituted or unsubstituted C$_5$-C$_7$ aryl or arylalkyl;

$R_3$ is $NR_9$—CO—$(CH_2)_n(CH_2CH_2O)_mR_{10}$, $NR_9$—CO—$(CH_2)_nR_{10}$, or $NR_9$—$SO_2$—$(CH_2)_nR_{10}$, wherein m, n, and o are independently an integer from 0-10 and each occurrence of $R_9$ is independently hydrogen, $C_1$-$C_{30}$ alkyl, or $C_5$-$C_7$ aryl, and $R_{10}$ is halogen, azide, cyano, $C_1$-$C_{30}$ alkoxy, aroxy, benzyloxy, trifluoromethyl, vinyl group, hydroxy, amino, primary amine, or secondary amine;

$R_2$ and $R_4$-$R_7$ are independently hydrogen, —OH, —SH, ether, thioether, primary amine, secondary amine, tertiary amine, ester, carboxylic acid, primary amide, secondary amide, tertiary amide, sulfonyl group, phosphate, nitro, halogen, nitrile, trifluoromethyl, or substituted or unsubstituted $C_1$-$C_{30}$ alkyl, $C_1$-$C_{30}$ heteroalkyl, $C_2$-$C_{30}$ alkenyl, or $C_2$-$C_{30}$ alkynyl; and wherein substituents for the substituted groups are independently halogen, hydroxyl, $C_1$-$C_{30}$ alkyl, $C_2$-$C_{30}$ alkenyl, $C_2$-$C_{30}$ alkynyl, phenyl, $C_5$-$C_7$ aryl, $C_5$-$C_7$ heteroaryl, $C_3$-$C_{10}$ cycloalkyl, $C_3$-$C_{10}$ heterocycloalkyl, alkoxy, phenoxy, aroxy, alkylthio, phenylthio, cyano, isocyano, carbonyl, carboxyl, amino, amido, sulfonyl, sulfonic acid, phosphoryl, or phosphonyl.

2. The compound of claim 1, wherein X, Y, W, and Z are oxygen.

3. The compound of claim 1, wherein $R_1$, $R_8$, or both are methyl, ethyl, propyl, isopropyl, butyl, isobutyl, sec-butyl, t-butyl, propenyl, benzyl, or $(CH_2)_3N_3$.

4. The compound of claim 1, wherein $R_2$ and $R_4$-$R_7$ are hydrogen.

5. The compound of claim 1, wherein $R_3$ is $NHCO(CH_2)_nR_{10}$.

6. The compound of claim 1, wherein $R_3$ is NH—$SO_2$—$(CH_2)_nR_{10}$.

7. The compound of claim 1, wherein $R_3$ is NH—CO—$(CH_2)_n(CH_2CH_2O)_mR_{10}$.

8. The compound of claim 1, wherein $R_{10}$ is $(CH_2)_p$NHCO$(CH_2)_q$halogen or $(CH_2)_p$NHCO$(CH_2)_q$NH$_2$, wherein p and q are independently integers from about 1-6.

9. A pharmaceutical composition comprising one or more compounds of claim 1 and one or more pharmaceutically acceptable carriers.

10. A method of treating leukemia comprising administering to a patient in need thereof a pharmaceutical composition comprising an effective amount of one or more compounds of claim 1.

11. The compound of claim 1, wherein the compound is:

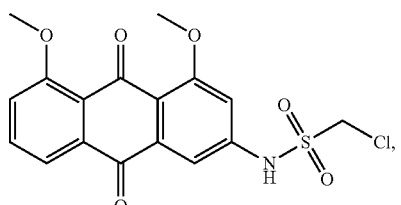

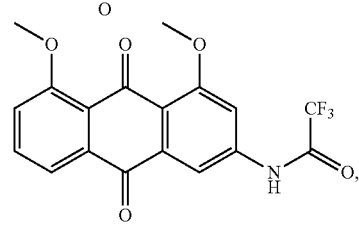

-continued

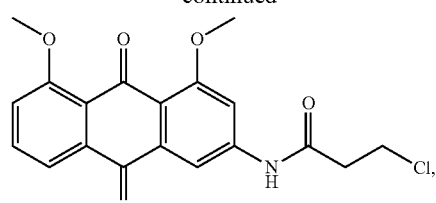

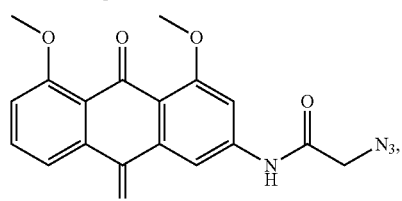

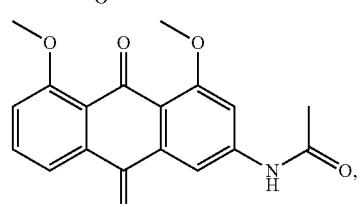

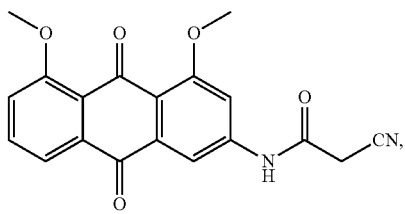

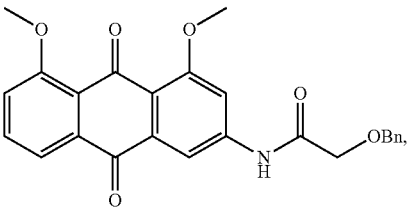

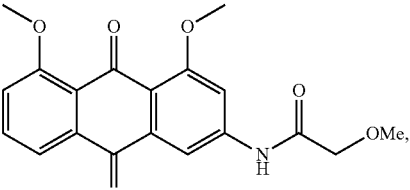

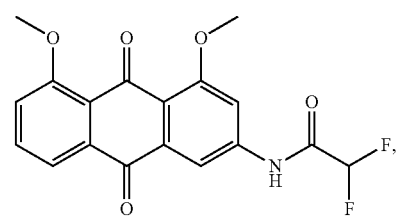

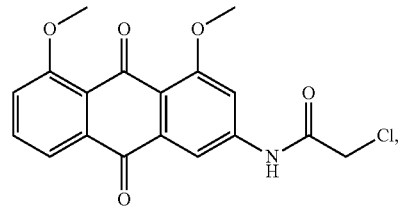

-continued

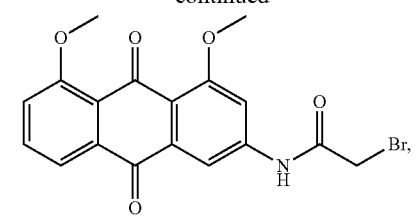

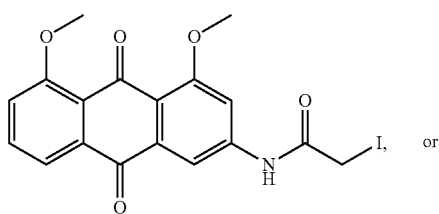

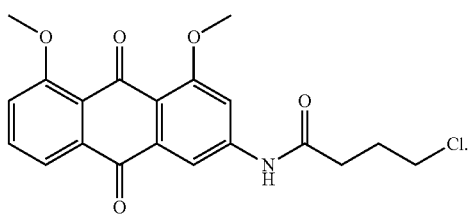

12. The compound of claim 1, wherein X and Y are O, and wherein $R_2$ and $R_4$-$R_7$ are independently hydrogen, —OH, —SH, ether, thioether, primary amine, secondary amine, tertiary amine, ester, carboxylic acid, primary amide, secondary amide, tertiary amide, sulfonyl group, phosphate, nitro, halogen, nitrile, trifluoromethyl, or substituted or unsubstituted $C_1$-$C_{30}$ alkyl or $C_1$-$C_{30}$ heteroalkyl.

13. The compound of claim 12, wherein $R_2$ and $R_4$-$R_7$ are independently hydrogen, —OH, —SH, ether, thioether, primary amine, secondary amine, tertiary amine, ester, carboxylic acid, primary amide, secondary amide, tertiary amide, sulfonyl group, phosphate, nitro, halogen, nitrile, trifluoromethyl, $C_1$-$C_{10}$ alkyl, or $C_1$-$C_{10}$ heteroalkyl.

14. The compound of claim 1, wherein $R_2$ and $R_4$-$R_7$ are independently hydrogen, —OH, —SH, ether, thioether, primary amine, secondary amine, tertiary amine, ester, carboxylic acid, primary amide, secondary amide, tertiary amide, sulfonyl group, phosphate, nitro, halogen, nitrile, trifluoromethyl, $C_1$-$C_{10}$ alkyl, or $C_1$-$C_{10}$ heteroalkyl.

15. The compound of claim 1, wherein $R_2$ and $R_4$-$R_7$ are lower alkyl.

16. The compound of claim 1, wherein $R_{10}$ is halogen or azide.

17. The compound of claim 1, wherein the compound is:

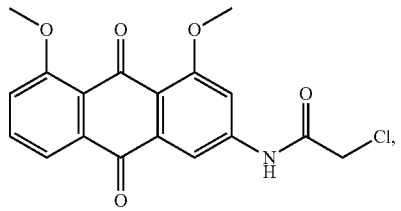

-continued

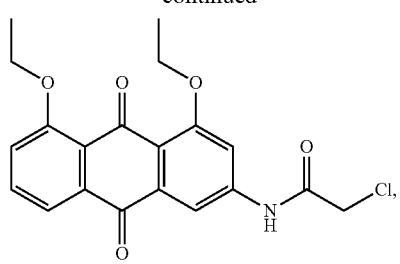

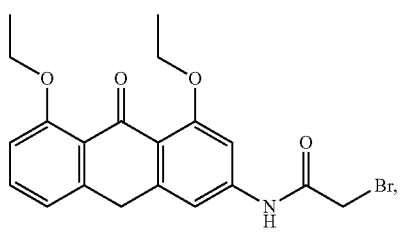

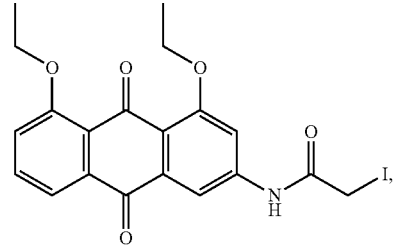

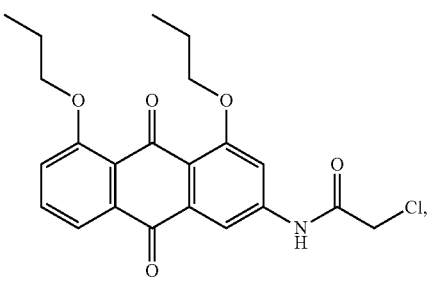

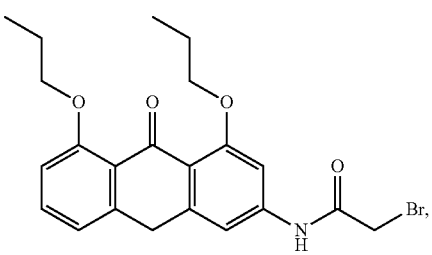

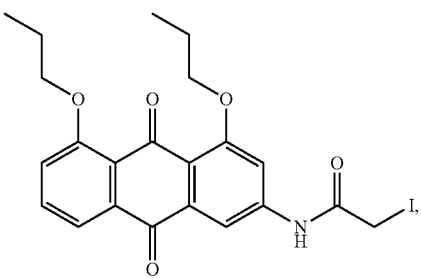

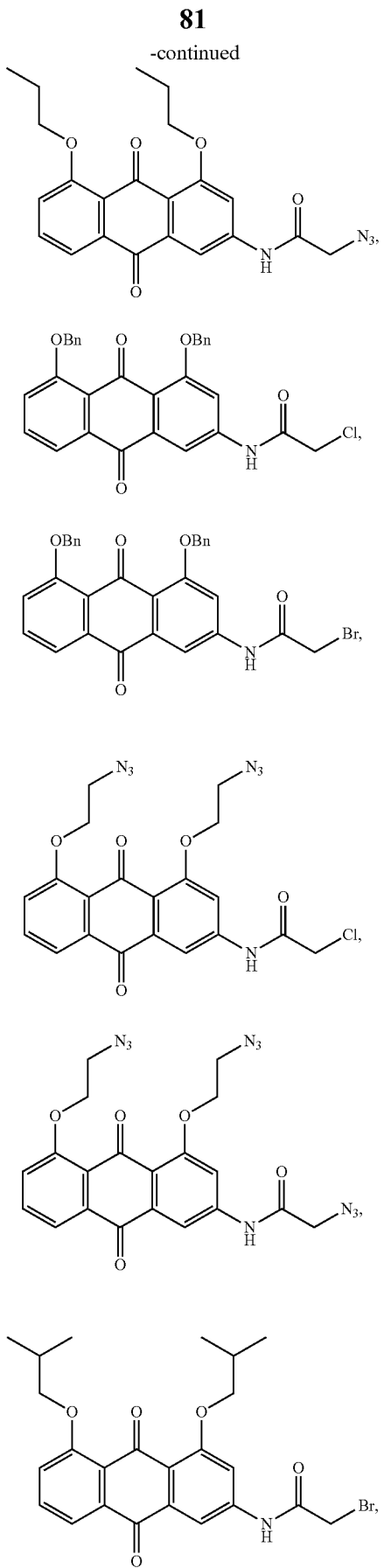

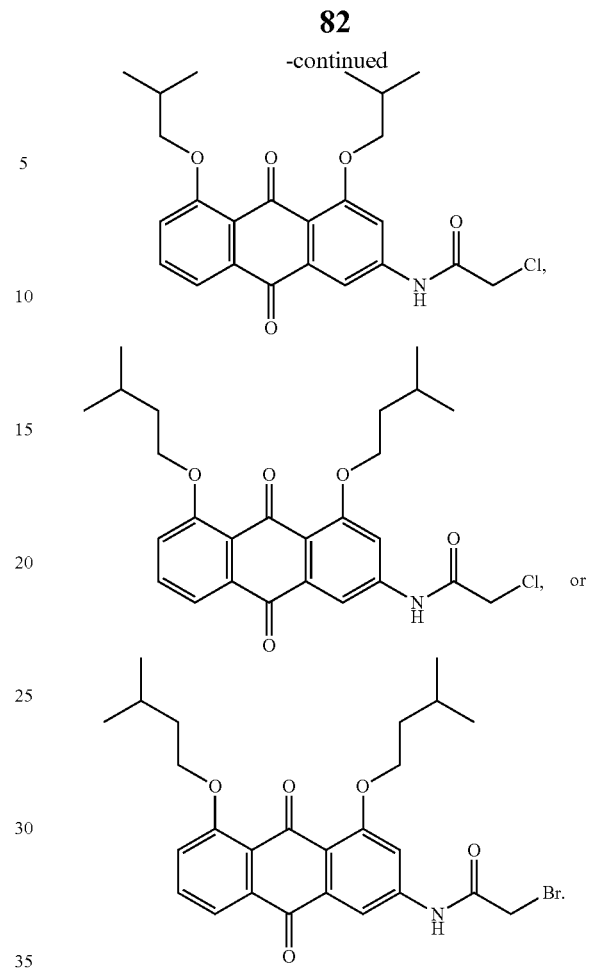

18. A method of treating leukemia comprising administering to a patient in need thereof a pharmaceutical composition comprising an effective amount of one or more compounds having formula:

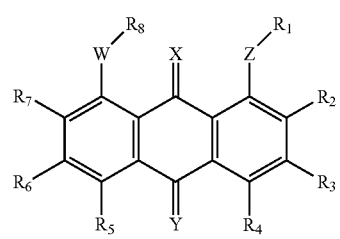

wherein

X, Y, W, and Z are independently O;

$R_1$ and $R_8$ are independently substituted or unsubstituted $C_1$-$C_{30}$ alkyl, or substituted or unsubstituted arylalkyl;

$R_3$ is $NR_9$—CO—$(CH_2)_n R_{10}$, wherein n is independently an integer from 0-10 and each occurrence of $R_9$ is independently hydrogen, $C_1$-$C_{30}$ alkyl, or $C_5$-$C_7$ aryl, and $R_{10}$ is halogen, azide, cyano, $C_1$-$C_{30}$ alkoxy, aroxy, benzyloxy, trifluoromethyl, vinyl group, hydroxy, amino, primary amine, or secondary amine;

$R_2$ and $R_4$-$R_7$ are independently hydrogen, —OH, —SH, ether, thioether, primary amine, secondary amine, tertiary amine, ester, carboxylic acid, primary amide, secondary amide, tertiary amide, sulfonyl group, phosphate, nitro, halogen, nitrile, trifluoromethyl, or substituted or unsubstituted $C_1$-$C_{30}$ alkyl, $C_1$-$C_{30}$ heteroalkyl, $C_2$-$C_{30}$ alkenyl, or $C_2$-$C_{30}$ alkynyl; and wherein substituents for the substituted groups are independently halogen, hydroxyl, $C_1$-$C_{30}$ alkyl, $C_2$-$C_{30}$ alkenyl, $C_2$-$C_{30}$ alkynyl, phenyl, $C_5$-$C_7$ aryl, $C_5$-$C_7$ heteroaryl, $C_3$-$C_{10}$ cycloalkyl, $C_3$-$C_{10}$ heterocycloalkyl, alkoxy, phenoxy, aroxy, alkylthio, phenylthio, cyano, isocyano, carbonyl, carboxyl, amino, amido, sulfonyl, sulfonic acid, phosphoryl, or phosphonyl.

19. The method of claim 18, wherein $R_1$, $R_8$, or both, are methyl, ethyl, propyl, isopropyl, butyl, isobutyl, sec-butyl, propenyl, benzyl, or $(CH_2)_3N_3$.

20. The method of claim 18, wherein $R_2$ and $R_4$-$R_7$ are independently hydrogen, $C_1$-$C_{10}$ alkyl, or $C_1$-$C_{10}$ heteroalkyl.

21. The method of claim 18, wherein $R_2$ and $R_4$-$R_7$ are hydrogen.

22. The method of claim 18, wherein n is independently an integer from 1-10.

23. The method of claim 18, wherein $R_3$ is NH—CO—$(CH_2)_n R_{10}$, wherein n is independently an integer from 1-10, and $R_{10}$ is halogen, azide, cyano, $C_1$-$C_{30}$ alkoxy, aroxy, benzyloxy, trifluoromethyl, vinyl group, hydroxy, amino, primary amine, or secondary amine.

24. The method of claim 18, wherein $R_9$ is hydrogen.

25. The method of claim 18, wherein $R_{10}$ is halogen or azide.

\* \* \* \* \*